United States Patent [19]
Bridges

[11] Patent Number: 6,153,617
[45] Date of Patent: Nov. 28, 2000

[54] IRREVERSIBLE BICYCLIC INHIBITORS OF TYROSINE KINASES

[75] Inventor: Alexander James Bridges, Saline, Mich.

[73] Assignee: Warner-Lambert Company, Morris Plains, N.J.

[21] Appl. No.: 09/269,647

[22] PCT Filed: Jul. 29, 1998

[86] PCT No.: PCT/US98/15592

§ 371 Date: Mar. 25, 1999

§ 102(e) Date: Mar. 25, 1999

[87] PCT Pub. No.: WO99/06396

PCT Pub. Date: Feb. 11, 1999

Related U.S. Application Data

[60] Provisional application No. 60/054,061, Jul. 29, 1997.
[51] Int. Cl.$^7$ ...................... A61K 31/489; C07D 239/72
[52] U.S. Cl. .......................... 514/259; 544/283; 544/284; 544/293
[58] Field of Search .................................. 514/259, 257; 546/293, 283, 284

[56] References Cited

U.S. PATENT DOCUMENTS 5,457,105 10/1995 Barker ...................... 514/234
5,475,001 12/1995 Barker ...................... 514/258

FOREIGN PATENT DOCUMENTS

| | | |
|---|---|---|
| 607439 | 4/1993 | European Pat. Off. . |
| 0 837 063 | 4/1998 | European Pat. Off. . |
| 9523141 | 4/1993 | WIPO . |
| 0 602 851 | 6/1994 | WIPO . |
| 95/15758 | 6/1995 | WIPO . |
| 95/19774 | 7/1995 | WIPO . |
| 95/23141 | 8/1995 | WIPO . |
| 96/09294 | 3/1996 | WIPO . |
| 97/22596 | 6/1997 | WIPO . |
| 97/38983 | 10/1997 | WIPO . |

*Primary Examiner*—Mukund J. Shah
*Assistant Examiner*—Sudhaker B. Patel
*Attorney, Agent, or Firm*—Francis J. Tinney

[57] ABSTRACT

The invention provides compounds of Formula I

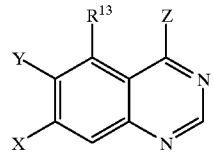

that are irreversible inhibitors of tyrosine kinases. Also provided is a method of treating cancer, restenosis, atherosclerosis, endometriosis, and psoriasis and a pharmaceutical composition that comprises a compound that is an irreversible inhibitor of tyrosine kinases.

22 Claims, No Drawings

IRREVERSIBLE BICYCLIC INHIBITORS OF TYROSINE KINASES

This application is a 371 of PCT/US98/15592 filed on Jul. 29, 1998. This application claims the benefit of U.S. Provisional Application Ser. No. 60/054,061 filed Jul. 29, 1997.

FIELD OF THE INVENTION

This invention relates to compounds that are irreversible inhibitors of tyrosine kinases. This invention also relates to a method of treating cancer, atherosclerosis, restenosis, endometriosis, and psoriasis, and to a pharmaceutical composition that comprises a compound that is an irreversible inhibitor of tyrosine kinases.

BACKGROUND OF THE INVENTION

Cancer has been viewed as a disease of the intracellular signalling system, or signal transduction mechanism. Cells receive instructions from many extracellular sources, instructing them to either proliferate or not to proliferate. The purpose of the signal transduction system is to receive these and other signals at the cell surface, get them into the cell, and then pass the signals on to the nucleus, the cytoskeleton, and transport and protein synthesis machinery.

The most common cause of cancer is a series of defects, either in these proteins, when they are mutated, or in the regulation of the quantity of the protein in the cell such that it is over or under produced. Most often, there are key lesions in the cell which lead to a constitutive state whereby the cell nucleus receives a signal to proliferate, when this signal is not actually present. This can occur through a variety of mechanisms. Sometimes the cell may start to produce an authentic growth factor for its own receptors when it should not, the so-called autocrine loop mechanism. Mutations to the cell surface receptors, which usually signal into the cell by means of tyrosine kinases, can lead to activation of the kinase in the absence of ligand, and passing of a signal which is not really there. Alternatively, many surface kinases can be overexpressed on the cell surface leading to an inappropriately strong response to a weak signal. There are many levels inside the cell at which mutation or overexpression can lead to the same spurious signal arising in the cell, and there are many other kinds of signalling defects involved in cancer. This invention touches upon cancers which are driven by the three mechanisms just described, and which involve cell surface receptors of the epidermal growth factor receptor tyrosine kinase family (EGFR). This family consists of the EGF receptor (also known as Erb-B1), the Erb-B2 receptor, and its constitutively active oncoprotein mutant Neu, the Erb-B3 receptor and the Erb-B4 receptor. Additionally, other biological processes driven through members of the EGF family of receptors can also be treated by compounds of the invention described below.

The EGFR has as its two most important ligands Epidermal Growth Factor (EGF) and Transforming Growth Factor alpha (TGF alpha). The receptors appear to have only minor functions in adult humans, but are apparently implicated in the disease process of a large portion of all cancers, especially colon and breast cancer. The closely related Erb-B2, Erb-B3, and Erb-B4 receptors have a family of Heregulins as their major ligands, and receptor overexpression and mutation have been unequivocally demonstrated as the major risk factor in poor prognosis breast cancer. Additionally, it has been demonstrated that all four of the members of this family of receptors can form heterodimeric signalling complexes with other members of the family, and that this can lead to synergistic transforming capacity if more than one member of the family is overexpressed in a malignancy. Overexpression of more than one family member has been shown to be relatively common in human malignancies.

In addition to cancer, restenosis is also a disease in which undesired cellular proliferation occurs. Restenosis involves the proliferation of vascular smooth muscle cells. Restenosis is a major clinical problem associated with coronary angioplasty and other medical procedures. Restenosis generally occurs within about 0 to 6 months in about 30% to 50% of patients who undergo balloon angioplasty to clear clogged coronary arteries in an effort to treat heart disease due to occluded arteries. The resulting restenosis causes substantial patient morbidity and health care expense.

The process of restenosis is initiated by injury of the blood vessel, including arteries and veins, with the subsequent release of thrombogenic, vasoactive, and mitogenic factors. Endothelial and deep vessel injury leads to platelet aggregation, thrombus formation, inflammation, and activation of macrophages and smooth muscle cells. These events induce the production of and release of growth factors and cytokines, which in turn may promote their own synthesis and release from target cells. Thus, a self-perpetuating process involving growth factors such as EGF, platelet derived growth factor (PDGF) or fibroblast growth factor (FGFs) is initiated. Thus, it would be usefull to have irreversible inhibitors of signal transduction pathways, particularly of tyrosine kinases like EGF, PDGF, FGF, or src tyrosine kinases.

The proliferative skin disease psoriasis has no good cure at present. It is often treated by anticancer agents such as methotrexate, which have very serious side effects, and which are not very effective at the toxicity limited doses which have to be used. It is believed that TGF alpha is the major growth factor overproduced in psoriasis, since 50% of transgenic mice which over express TGF alpha develop psoriasis. This suggests that a good inhibitor of EGFR signalling could be used as antipsoriatic agent, preferably, but not necessarily, by topical dosing.

It is especially advantageous to have irreversible tyrosine kinase inhibitors when compared to reversible inhibitors, because irreversible inhibitors can be used in prolonged suppression of the tyrosine kinase, limited only by the normal rate of receptor resynthesis, also called turnover.

Additional information on the role of src tyrosine kinases in biological processes relating to cancer and restenosis can be found in the following documents, which are all hereby incorporated by reference.

Benjamin C. W. and Jones D. A., Platelet-Derived Growth Factor Stimulates Growth Factor Receptor Binding Protein-2 Association With Src In Vascular Smooth Muscle Cells, *JBC*, 1994;269:30911–30916.

Kovalenko M., et al., Selective Platelet-Derived Growth Factor Receptor Kinase Blockers Reverse Cis-transformation, *Cancer Res*, 1994;54:6106–6114.

Schwartz R. S., et al., The Restenosis Paradigm Revisted: An Alternative Proposal for Cellular Mechanisms, *J Am Coll Cardiol*, 1992;20:1284–1293.

Libby P., et al., Cascade Model for Restenosis—A Special Case of Atherosclerosis Progression, *Circulation*, 1992;86:47–52.

Additional information on the role of EGF tyrosine kinases in biological processes relating to cancer and restenosis can be found in the following document which is hereby incorporated by reference.

Jonathan Blay and Morley D. Hollenberg, Heterologous Regulation Of EGF Receptor Function In Cultured Aortic Smooth Muscle Cells, *Eur J Pharmacol, Mol Pharmacol Sect*, 1989; 172(1):1–7.

Information that shows that antibodies to EGF or EGFR show in vivo antitumor activity can be found in the following documents which are hereby incorporated by reference.

Modjtahedi H., Eccles S., Box G., Styles J., Dean C., Immunotherapy Of Human Tumour Xenografts Overexpressing The EGF Receptor With Rat Antibodies That Block Growth Factor-Receptor Interaction, *Br J Cancer*, 1993;67:254–261.

Kurachi H., Morishige K. I., Amemiya K., Adachi H., Hirota K., Miyake A., Tanizawa O., Importance Of Transforming Growth Factor Alpha/Epidermal Growth Factor Receptor Autocrine Growth Mechanism In An Ovarian Cancer Cell Line In Vivo, *Cancer Res*, 1991;51:5956–5959.

Masui H., Moroyama T., Mendelsohn J., Mechanism Of Antitumor Activity In Mice For Anti-Epidermal Growth Factor Receptor Monoclonal Antibodies With Different Isotypes, *Cancer Res*, 1986;46:5592–5598.

Rodeck U., Herlyn M., Herlyn D., Molthoff C., Atkinson B., Varello M., Steplewski Z., Koprowski H., Tumor Growth Modulation By A Monoclonal Antibody To The Epidermal Growth Factor Receptor: Immunologically Mediated And Effector Cell-Independent Effects, *Cancer Res*, 1987;47:3692–3696.

Guan E., Zhou T., Wang J., Huang P., Tang W., Zhao M., Chen Y., Sun Y., Growth Inhibition Of Human Nasopharyngeal Carcinoma In Athymic Mice By Anti-Epidermal Growth Factor Receptor Monoclonal Antibodies, *Internat J Cell Clon*, 1989;7:242–256.

Masui H., Kawamoto T., Sato J. D., Wolf B., Sato G., Mendelsohn J., Growth Inhibition Of Human Tumor Cells in Athymic Mice By Anti-Epidermal Growth Factor Receptor Monoclonal Antibodies, *Cancer Res*, 1984;44:1002–1007.

In addition, the following documents show the antitumor activity of protein tyrosine kinase inhibitors. The documents are hereby incorporated by reference.

Buchdunger E., Trinks U., Mett H., Regenass U., Muller M., Meyer T., McGlynn E., Pinna L. A., Traxler P., Lydon N. B., 4,5-Dianilinophthalimide: A Protein Tyrosine Kinase Inhibitor With Selectivity For The Epidermal Growth Factor Receptor Signal Transduction Pathway And Potent In Vivo Antitumor Activity, *Proc Natl Acad Sci USA*, 1994;91:2334–2338.

Buchdunger E., Mett H., Trinks U., Regenass U., Muller M., Meyer T., Beilstein P., Wirz B., Schneider P., Traxler P., Lydon N., 4,5-Bis (4-Fluoroanilino)Phthalimide: A Selective Inhibitor Of The Epidermal Growth Factor Receptor Signal Transduction Pathway With Potent In Vivo Mdd Antitumor Activity, *Clinical Cancer Research*, 1995;1:813–821.

Compounds that are reversible inhibitors of tyrosine kinases have been described in U.S. Pat. Nos. 5,457,105, 5,475,001, and 5,409,930 and in PCT publication Numbers WO 9519774, WO 9519970, WO 9609294, and WO 9523141. The presently disclosed compounds, which are structurally different from the tyrosine kinase inhibitors described in the above-identified documents, are irreversible inhibitors of tyrosine kinases.

SUMMARY OF THE INVENTION

The present invention provides compounds having the Formula I

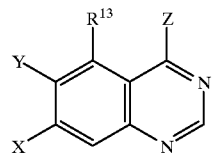

wherein X is —D—E—F and Y is —$SR^4$, halogen, —$OR^4$, —$NHR^3$, or hydrogen, or X is —$SR^4$, halogen, —$OR^4$, —$NHR^3$, or hydrogen, and Y is —D—E—F;

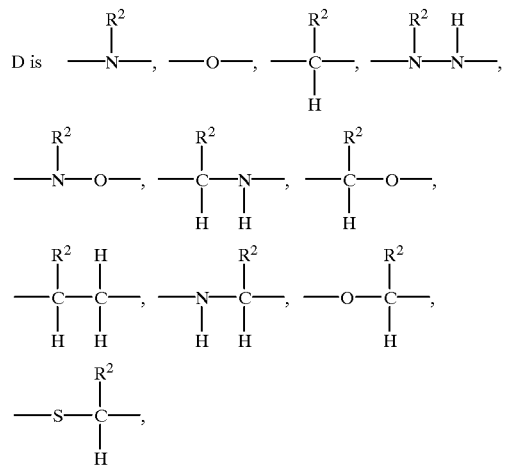

or absent;

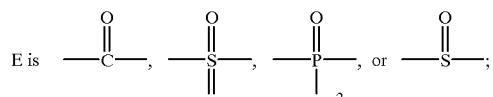

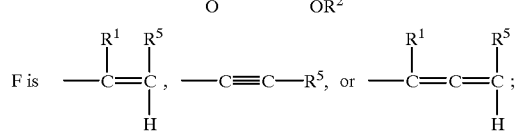

provided that when E is

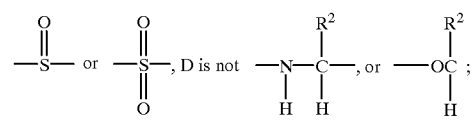

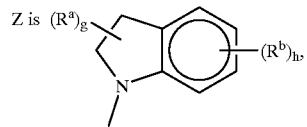

-continued

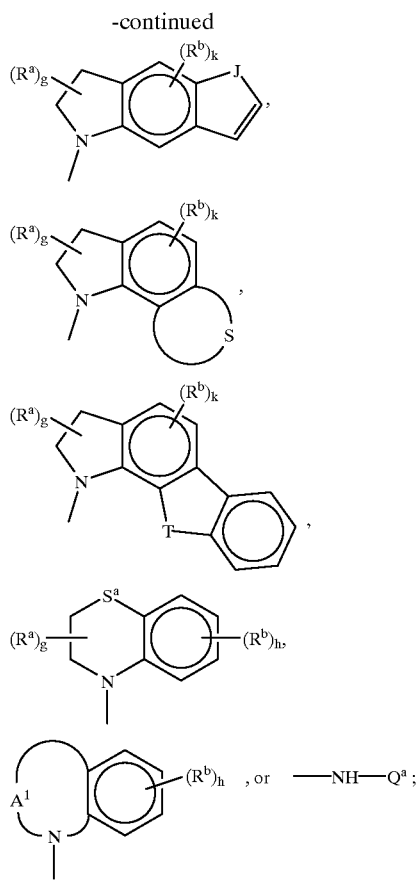

each $R^a$ is independently hydroxy, amino, N-mono- or N,N-di-($C_1$–$C_4$) alkylamino, sulfo, or ($C_1$–$C_4$)alkoxy (provided that such groups are not attached to a ring carbon which is adjacent to an oxy, thio, or —N—), or $R^a$ is independently carboxy, hydroxy($C_1$–$C_4$)alkyl, ($C_1$–$C_4$) alkoxy($C_1$–$C_4$) alkyl, amino($C_1$–$C_4$)alkyl, mono-N- or di-N,N-($C_1$–$C_4$)alkylamino($C_1$–$C_4$)alkyl, morpholino ($C_1$–$C_4$)alkyl, 4-($C_1$–$C_4$)alkyl-piperazin-1-yl($C_1$–$C_4$) alkyl, carboxy($C_1$–$C_4$)alkyl, ($C_1$–$C_4$)alkoxycarbonyl, sulfo($C_1$–$C_4$)alkyl, or ($C_1$–$C_4$)alkyl;

each $R^b$ is independently mono-, di-, or trifluoromethyl, halo, nitro, hydroxy, amino, axido, isothiocyano, ($C_1$–$C_4$) alkyl, phenyl, thienyl, ($C_1$–$C_4$)alkoxy, benzyloxy, phenoxy, ($C_2$–$C_6$)alkenyl, ($C_2$–$C_6$)alkynyl, ($C_1$–$C_4$) alkylenedioxy, cyano, benzoylamino, trifluoromethylcarbonylamino, ($C_1$–$C_4$)alkanoylamino, ($C_1$–$C_4$)alkanoyl, N-mono- or N,N-di-($C_1$–$C_4$) alkylamino, ($C_1$–$C_4$)alkylsulfonylamino, trifluoromethylsulfonylamino, ($C_1$–$C_4$)alkylthio, ($C_1$–$C_4$) alkylsulfinyl or ($C_1$–$C_4$)alkylsulfonyl, pyrrol-1-yl, piperidin-1-yl or pyrrolidin-1-yl, said phenyl, benzyloxy, phenoxy, and benzoylamino optionally mono-substituted with halo, nitro, trifluoromethyl, hydroxy, or ($C_1$–$C_4$) alkyl and said ($C_{hd\ 1}$–$C_4$)alkylenedioxy is linked at both ends to adjacent carbons on the benzene moiety, or $R^b$ is —$Z^a R^{77}$;

J is —$CH_2$—, thio, —N(H)—, or oxy;
g is 0, 1, or 2;
h is 0 to 4;
k is 0, 1, or 2;
S completes a 5- or 6-membered aromatic or partially saturated ring that can contain an oxygen or sulfur atom;
T is —$CH_2$—, —N(H)—, thio, or oxy;
$S^a$ is —$CH_2$—, oxy, or thio;

$A^1$ completes a 7- to 9-membered mono-unsaturated mono-aza ring;
$R^1$ is hydrogen, halogen, or $C_1$–$C_6$ alkyl;
$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, ($C_1$–$C_4$) alkyl, ($C_1$–$C_4$)alkoxy, ($C_1$–$C_4$)alkylamino, di-[($C_1$–$C_4$) alkyl]amino, and ($C_2$–$C_4$)alkanoylamino;
$R^2$, $R^3$, and $R^4$ are independently hydrogen, $C_1$–$C_6$ alkyl, —$(CH_2)_n$—N-piperidinyl, —$(CH_2)_n$—N-piperazinyl, —$(CH_2)_n$—$N_1$-piperazinyl[$N_4$-($C_1$–$C_6$)alkyl], —$(CH_2)_n$—N-pyrrolidyl, —$(CH_2)_n$-pyridinyl, —$(CH_2)_n$—N-imidazoyl, —$(CH_2)_n$—imidazoyl, —$(CH_2)_n$—N-morpholino, —$(CH_2)_n$—N-thiomorpholino, —$(CH_2)_n$—N-hexahydroazepine or substituted $C_1$–$C_6$ alkyl, wherein the substituents are selected from —OH, —$NH_2$, or $$-\underset{|}{\overset{A}{N}}-B,$$

A and B are independently hydrogen, $C_1$–$C_6$ alkyl, —$(CH_2)_n$ OH, —$(CH_2)_n$—N-piperidinyl, —$(CH_2)_n$—N-piperazinyl, —$(CH_2)_n$—$N_1$-piperazinyl [$N_4$-($C_1$–$C_6$)alkyl], —$(CH_2)_n$—N-pyrrolidyl, —$(CH_2)_n$—N-pyridyl, —$(CH_2)_n$-imidazoyl, or —$(CH_2)_n$—N-imidazoyl;
$Z^1$, $Z^2$, or $Z^3$ are independently hydrogen, halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;
$Z^a$ is a bond, —$CH_2$—, —S—, $SO_2$, —NH—, —O—, —$OCH_2$—, —S—$CH_2$—, —$SO_2 CH_2$—, or —$CH_2 CH_2$—;
$R^5$ is hydrogen, halogen, $C_1$–$C_6$ perfluoroalkyl, 1,1-difluoro ($C_1$–$C_6$)alkyl, $C_1$–$C_6$ alkyl, —$(CH_2)_n$—N-piperidinyl, —$(CH_2)_n$-piperazinyl, —$(CH_2)_n$-piperazinyl[$N_4$-($C_1$–$C_6$) alkyl], —$(CH_2)_n$—N-pyrrolidyl, —$(CH_2)_n$-pyridinyl, —$(CH_2)_n$—N-imidazoyl, —$(CH_2)_n$—N-morpholino, —$(CH_2)_n$—N-thiomorpholino

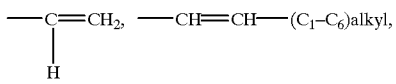

—$(CH_2)_n$—N-hexahydroazepine, —$(CH_2)_n NH_2$, —$(CH_2)_n NH(C_1$–$C_6$alkyl), —$(CH_2)_n N(C_1$–$C_6$alkyl)$_2$, -1-oxo($C_1$–$C_6$)alkyl, carboxy, ($C_1$–$C_6$)alkyloxycarbonyl, N-($C_1$–$C_6$)alkylcarbamoyl, phenyl or substituted phenyl, wherein the substituted phenyl can have from one to three substituents independently selected from $Z^1$, $Z^2$, $Z^3$ or a monocyclic heteroaryl group, and each $C_1$–$C_6$ alkyl group above in $R^5$ can be substituted with —OH, —$NH_2$ or —NAB, where A and B are as defined above;

$R^{77}$ is phenyl, substituted phenyl, or a 5- to 10-membered optionally substituted heterocyclic aromatic ring;
$R^{13}$ is hydrogen or halogen; and
n is 1 to 4, and the pharmaceutically acceptable salts, esters, amides, and prodrugs thereof.

In a preferred embodiment of the compounds of Formula I,

X is 
$$-\underset{\underset{R^2}{|}}{N}-\underset{\underset{O}{\|}}{C}-\underset{\underset{CHR^5}{|}}{C}-R^1,$$

and Y is hydrogen, or
X is hydrogen, and Y is $$-\underset{\underset{R^2}{|}}{N}-\underset{\underset{O}{\|}}{C}-\underset{\underset{CHR^5}{|}}{C}-R^1.$$

In another preferred embodiment of the compounds of Formula I, Y is —D—E—F, and —D—E—F is $$-\underset{\underset{R^2}{|}}{N}-\underset{\underset{O}{\|}}{C}-\underset{\underset{R^1}{|}}{C}-\underset{\underset{R^5}{|}}{CH}, \quad -\underset{\underset{R^2}{|}}{N}-\underset{\underset{\underset{O}{\|}}{\overset{O}{\|}}{S}}{}-\underset{\underset{R^1}{|}}{C}-\underset{\underset{R^5}{|}}{CH}, \text{ or}$$

$$-\underset{\underset{R^2}{|}}{N}-\underset{\underset{\underset{OR^2}{|}}{\overset{O}{\|}}{P}}{}-\underset{\underset{R^1}{|}}{C}-\underset{\underset{R^5}{|}}{CH}.$$

In another preferred embodiment of the compounds of Formula I, X is —D—E—F, and —D—E—F is $$-\underset{\underset{R^2}{|}}{N}-\underset{\underset{O}{\|}}{C}-\underset{\underset{R^1}{|}}{C}-\underset{\underset{R^5}{|}}{CH}, \quad -\underset{\underset{R^2}{|}}{N}-\underset{\underset{\underset{O}{\|}}{\overset{O}{\|}}{S}}{}-\underset{\underset{R^1}{|}}{C}-\underset{\underset{R^5}{|}}{CH}, \text{ or}$$

$$-\underset{\underset{R^2}{|}}{N}-\underset{\underset{\underset{OR^2}{|}}{\overset{O}{\|}}{P}}{}-\underset{\underset{R^1}{|}}{C}-\underset{\underset{R^5}{|}}{CH}.$$

In another preferred embodiment of the compounds of Formula I, $R^2$ is hydrogen.

In another preferred embodiment of the compounds of Formula I, Y is —D—E—F and X is —O($CH_2$)$_n$-morpholino.

In another preferred embodiment of the compounds of Formula I, $R^5$ is carboxy, ($C_1$–$C_6$ alkyl)oxycarbonyl or $C_1$–$C_6$ alkyl.

In another preferred embodiment of the compounds of Formula I, Y is —D—E—F and X is —O($CH_2$)$_n$morpholino.

In another preferred embodiment of the compounds of Formula I, Y is —D—E—F and X is —O—($CH_2$)$_n$—$N_1$-piperazinyl[$N_4$-($C_1$–$C_6$)alkyl].

In another preferred embodiment of the compounds of Formula I, Y is —D—E—F and X is —O—($CH_2$)$_n$-imidazoyl.

In another embodiment, the present invention provides compounds having the Formula II

Q—Z      II wherein Q is

[four fused bicyclic pyrido-pyrimidine/naphthyridine structures with X and Y substituents]

p is 0 or 1;
X is —D—E—F and Y is —$SR^4$, —$OR^4$, —$NHR^3$ or hydrogen, or X is —$SR^4$, —$OR^4$, —$NHR^3$ or hydrogen, and Y is —D—E—F;

D is 
$$-\underset{\underset{R^2}{|}}{N}-, \quad -O-, \quad -\underset{\underset{H}{|}}{\overset{R^2}{|}}{C}-, \quad -\underset{\underset{R^2}{|}}{N}-\underset{\underset{H}{|}}{N}-,$$

$$-\underset{\underset{R^2}{|}}{N}-O-, \quad -\underset{\underset{H}{|}}{\overset{R^2}{|}}{C}-\underset{\underset{H}{|}}{N}-, \quad -\underset{\underset{H}{|}}{\overset{R^2}{|}}{C}-O-,$$

$$-\underset{\underset{H}{|}}{\overset{R^2}{|}}{C}-\underset{\underset{H}{|}}{\overset{H}{|}}{C}-, \quad -\underset{\underset{H}{|}}{N}-\underset{\underset{H}{|}}{\overset{R^2}{|}}{C}-, \quad -O-\underset{\underset{H}{|}}{\overset{R^2}{|}}{C}-,$$

$$-S-\underset{\underset{H}{|}}{\overset{R^2}{|}}{C}-,$$

or absent;

E is 
$$-\underset{\underset{O}{\|}}{C}-, \quad -\underset{\underset{\underset{O}{\|}}{\overset{O}{\|}}{S}}{}-, \quad -\underset{\underset{\underset{OR^2}{|}}{\overset{O}{\|}}{P}}{}-, \text{ or } -\underset{\underset{O}{\|}}{S}-;$$

F is 
$$-\underset{\underset{H}{|}}{\overset{R^1}{|}}{C}=\underset{\underset{H}{|}}{\overset{R^5}{|}}{C}, \quad -C{\equiv}C-R^5, \quad -\underset{\underset{H}{|}}{\overset{R^1}{|}}{C}=\underset{\underset{H}{|}}{\overset{R^5}{|}}{C};$$

provided that when E is $$-\underset{\underset{O}{\|}}{S}- \text{ or } -\underset{\underset{\underset{O}{\|}}{\overset{O}{\|}}{S}}{}-, \text{ D is not } -\underset{\underset{H}{|}}{N}-\underset{\underset{H}{|}}{\overset{R^2}{|}}{C}-, \text{ or } -O-\underset{\underset{H}{|}}{\overset{R^2}{|}}{C};$$

Z is $(R^a)_g$—[indoline ring with $(R^b)_h$]

-continued

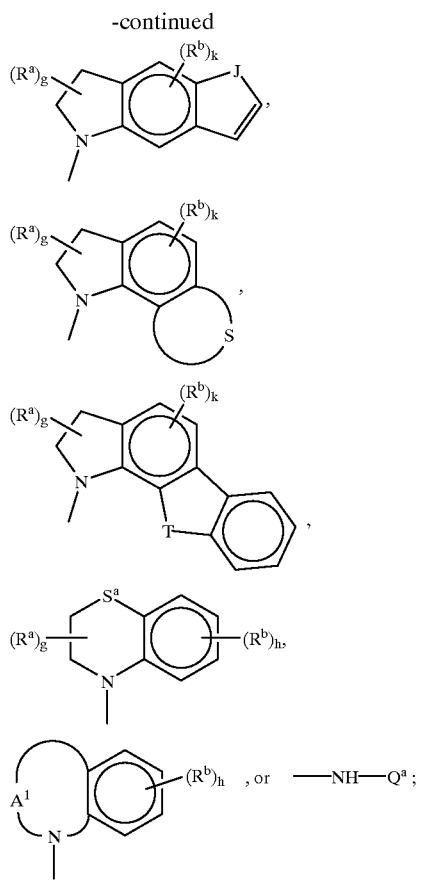

each $R^a$ is independently hydroxy, amino, N-mono- or N,N-di-($C_1$–$C_4$) alkylamino, sulfo, or ($C_1$–$C_4$)alkoxy (provided that such groups are not attached to a ring carbon which is adjacent to an oxy, thio, or —N—), or $R^a$ is independently carboxy, hydroxy($C_1$–$C_4$)alkyl, ($C_1$–$C_4$) alkoxy($C_1$–$C_4$) alkyl, amino($C_1$–$C_4$)alkyl, mono-N- or di-N,N-($C_1$–$C_4$)alkylamino($C_1$–$C_4$)alkyl, morpholino ($C_1$–$C_4$)alkyl, 4-($C_1$–$C_4$)alkyl-piperazin-1-yl($C_1$–$C_4$) alkyl, carboxy($C_1$–$C_4$)alkyl, ($C_1$–$C_4$)alkoxycarbonyl, sulfo($C_1$–$C_4$)alkyl, or ($C_1$–$C_4$)alkyl;

each $R^b$ is independently mono-, di-, or trifluoromethyl, halo, nitro, hydroxy, amino, axido, isothiocyano, ($C_1$–$C_4$) alkyl, phenyl, thienyl, ($C_1$–$C_4$)alkoxy, benzyloxy, phenoxy, ($C_2$–$C_6$)alkenyl, ($C_2$–$C_6$)alkynyl, ($C_1$–$C_4$) alkylenedioxy, cyano, benzoylamino, trifluoromethylcarbonylamino, ($C_1$–$C_4$)alkanoylamino, ($C_1$–$C_4$)alkanoyl, N-mono- or N,N-di-($C_1$–$C_4$) alkylamino, ($C_1$–$C_4$)alkylsulfonylamino, trifluoromethylsulfonylamino, ($C_1$–$C_4$)alkylthio, ($C_1$–$C_4$) alkylsulfinyl or ($C_1$–$C_4$)alkylsulfonyl, pyrrol-1-yl, piperidin-1-yl or pyrrolidin-1-yl, said phenyl, benzyloxy, phenoxy, and benzoylamino optionally mono-substituted with halo, nitro, trifluoromethyl, hydroxy, or ($C_1$–$C_4$) alkyl and said ($C_1$–$C_4$)alkylenedioxy is linked at both ends to adjacent carbons on the benzene moiety, or $R^b$ is —$Z^a R^{77}$;

J is —$CH_2$—, thio, —N(H)—, or oxy;
g is 0, 1, or 2;
h is 0 to 4;
k is 0, 1, or 2;
S completes a 5- or 6-membered aromatic or partially saturated ring that can contain an oxygen or sulfur atom;
T is —$CH_2$—, —N(H)—, thio, or oxy;
$S^a$ is —$CH_2$—, oxy, or thio;

$A^1$ completes a 7- to 9-membered mono-unsaturated mono-aza ring;
$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, ($C_1$–$C_4$) alkyl, ($C_1$–$C_4$)alkoxy, ($C_1$–$C_4$)alkylamino, di-[($C_1$–$C_4$) alkyl]amino, and ($C_2$–$C_4$)alkanoylamino;
$R^1$ is hydrogen, halogen, or $C_1$–$C_6$ alkyl;
$R^2$, $R^3$, and $R^4$ are independently hydrogen, $C_1$–$C_6$ alkyl, —$(CH_2)_n$—N-pipendinyl, —$(CH_2)_n$—N-piperazinyl, —$(CH_2)_n$—$N_1$-piperazinyl[$N_4$-($C_1$–$C_6$)alkyl], —$(CH_2)_n$—N-pyrrolidyl, —$(CH_2)_n$-pyridinyl, —$(CH_2)_n$—N-imidazoyl, —$(CH_2)_n$-imidazoyl, —$(CH_2)_n$—N-morpholino, —$(CH_2)_n$—N-thiomorpholino, —$(CH_2)_n$—N-hexahydroazepine or substituted $C_1$–$C_6$ alkyl, wherein the substituents are selected from —OH, —$NH_2$, or

A and B are
independently hydrogen, $C_1$–$C_6$ alkyl, —$(C_2CH_2)_n$OH, —$(CH_2)_n$—N-piperidinyl, —$(CH_2)_n$—N-piperazinyl, —$(CH_2)_n$—$N_1$-piperazinyl[$N_4$—($C_1$–$C_6$)alkyl], —$(CH_2)_n$—N-pyrrolidyl, —$(CH_2)_n$—N-pyridyl, —$(CH_2)_n$-imidazoyl, or —$(CH_2)_n$—N-imidazoyl;
$E^1$, $E^2$, or $E^3$ are independently hydrogen, halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;
$Z^a$ is a bond, —$CH_2$—, —S—, $SO_2$, —NH—, —O—, —$OCH_2$—, —S—$CH_2$—, —$SO_2$—, or —$CH_2CH_2$—;
$R^{77}$ is phenyl, substituted phenyl, or a 5- to 10-membered optionally substituted heterocyclic aromatic ring;
$R^5$ is hydrogen, halogen, $C_1$–$C_6$ perfluoroalkyl, 1,1-difluoro ($C_1$–$C_6$)alkyl, $C_1$–$C_6$ alkyl, —$(CH_2)_n$—N-piperidinyl, —$(CH_2)_n$-piperazinyl, —$(CH_2)_n$-piperazinyl[$N_4$—($C_1$–$C_6$)alkyl], —$(CH_2)_n$—N-pyrrolidyl, —$(CH_2)_n$-pyridinyl, —$(CH_2)_n$—N-imidazoyl, —$(CH_2)_n$—N-morpholino, —$(CH_2)_n$—N-thiomorpholino,

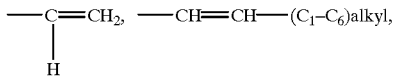

—$(CH_2)_n$—N-hexahydroazepine, —$(CH_2)_n NH_2$, —$(CH_2)_n$ NH($C_1$–$C_6$alkyl), —$(CH_2)_n$N($C_1$–$C_6$alkyl)$_2$, -1-oxo($C_1$–$C_6$)alkyl, carboxy, ($C_1$–$C_6$)alkyloxycarbonyl, N-($C_1$–$C_6$)alkylcarbamoyl, phenyl or substituted phenyl, wherein the substituted phenyl can have from one to three substituents independently selected from $E^1$, $E^2$, $E^3$ or a monocyclic heteroaryl group, and each $C_1$–$C_6$ alkyl group can be substituted with —OH, —NH₂ or —NAB, where A and B are as defined above; and n is 1 to 4, and the pharmaceutically acceptable salts, esters, amides, and prodrugs thereof.

In another preferred embodiment of the compounds of Formula II, Q is

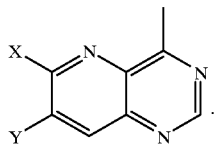

In another preferred embodiment of the compounds of Formula II, Q is

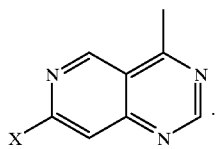

In another preferred embodiment of the compounds of Formula II, Q is

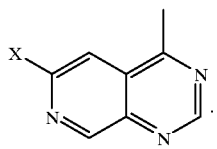

In another preferred embodiment of the compounds of Formula II, Q is

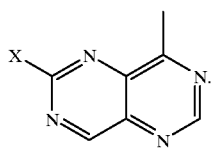

In another preferred embodiment of the compounds of Formula II, X is

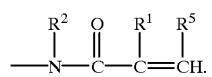

In another preferred embodiment of the compounds of Formula II, X is

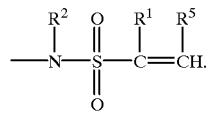

In another embodiment, the present invention provides compounds having the Formula II

Q—Z    II wherein Q is

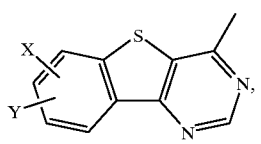

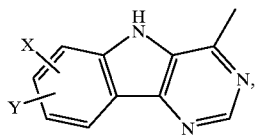

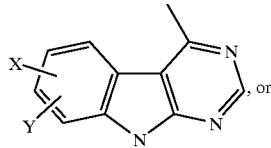

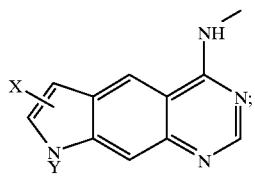

p is 0 or 1;

X is —D—E—F, and Y is —SR⁴, —OR⁴, —NHR³ or hydrogen, or X is —SR⁴, —OR⁴, —NHR³ or hydrogen, and Y is —D—E—F;

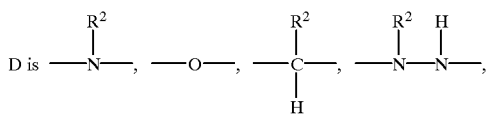

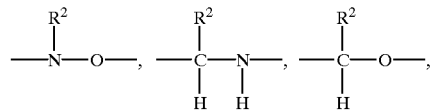

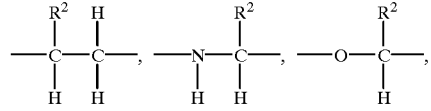

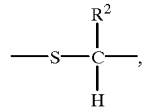

or absent;

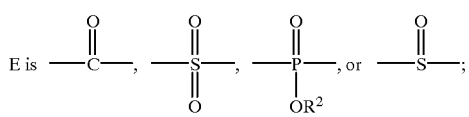

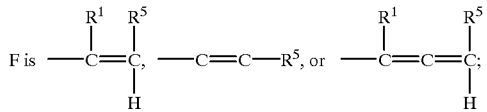

provided that when E is

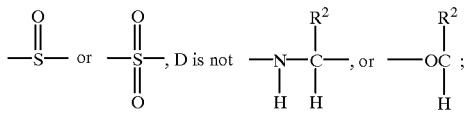

, D is not

Z is

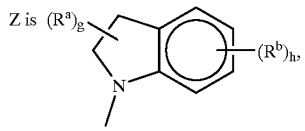

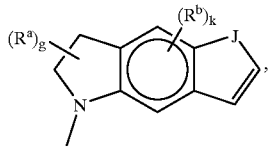

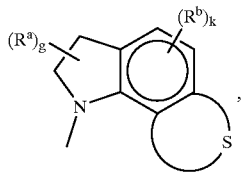

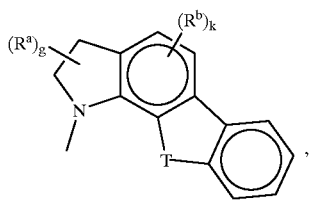

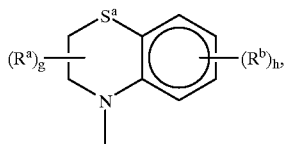

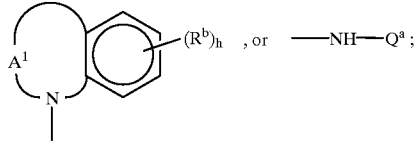, or —NH—$Q^a$ ;

each $R^a$ is independently hydroxy, amino, N-mono- or N,N-di-$(C_1-C_4)$ alkylamino, sulfo, or $(C_1-C_4)$alkoxy (provided that such groups are not attached to a ring carbon which is adjacent to an oxy, thio, or —N—), or $R^a$ is independently carboxy, hydroxy$(C_1-C_4)$alkyl, $(C_1-C_4)$ alkoxy$(C_1-C_4)$ alkyl, amino$(C_1-C_4)$alkyl, mono-N- or di-N,N-$(C_1-C_4)$alkylamino$(C_1-C_4)$alkyl, morpholino $(C_1-C_4)$alkyl, 4-$(C_1-C_4)$alkyl-piperazin-1-yl$(C_1-C_4)$ alkyl, carboxy$(C_1-C_4)$alkyl, $(C_1-C_4)$alkoxycarbonyl, sulfo$(C_1-C_4)$alkyl, or $(C_1-C_4)$alkyl;

each $R^b$ is independently mono-, di-, or trifluoromethyl, halo, nitro, hydroxy, amino, axido, isothiocyano, $(C_1-C_4)$ alkyl, phenyl, thienyl, $(C_1-C_4)$alkoxy, benzyloxy, phenoxy, $(C_2-C_6)$alkenyl, $(C_2-C_6)$alkynyl, $(C_1-C_4)$ alkylenedioxy, cyano, benzoylamino, trifluoromethylcarbonylamino, $(C_1-C_4)$alkanoylamino, $(C_1-C_4)$alkanoyl, N-mono- or N,N-di-$(C_1-C_4)$ alkylamino, $(C_1-C_4)$alkylsulfonylamino, trifluoromethylsulfonylamino, $(C_1-C_4)$alkylthio, $(C_1-C_4)$ alkylsulfinyl or $(C_1-C_4)$alkylsulfonyl, pyrrol-1-yl, piperidin-1-yl or pyrrolidin-1-yl, said phenyl, benzyloxy, phenoxy, and benzoylamino optionally mono-substituted with halo, nitro, trifluoromethyl, hydroxy, or $(C_1-C_4)$ alkyl and said $(C_1-C_4)$alkylenedioxy is linked at both ends to adjacent carbons on the benzene moiety, or $R^b$ is —$Z^a R^{77}$;

J is —$CH_2$—, thio, —N(H)—, or oxy;

g is 0, 1, or 2;

h is 0 to 4;

k is 0, 1, or 2;

S completes a 5- or 6-membered aromatic or partially saturated ring that can contain an oxygen or sulftur atom;

T is —$CH_2$, —N(H)—, thio, or oxy;

$S^a$ is —$CH_2$—, oxy, or thio;

$A^1$ completes a 7- to 9-membered mono-unsaturated mono-aza ring;

$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, $(C_1-C_4)$ alkyl, $(C_1-C_4)$alkoxy, $(C_1-C_4)$alkylamino, di-[$(C_1-C_4)$ alkyl]amino, and $(C_2-C_4)$alkanoylamino;

$R^1$ is hydrogen, halogen, or $C_1-C_6$ alkyl;

$R^2$, $R^3$, and $R^4$ are independently hydrogen, $C_1-C_6$ alkyl, —$(CH_2)_n$—N-piperidinyl, —$(CH_2)_n$—N-piperazinyl, —$(CH_2)_n$—$N_1$-piperazinyl[$N_4$-$(C_1-C_6)$alkyl], —$(CH_2)_n$ —N-pyrrolidyl, —$(CH_2)_n$-pyridinyl, —$(CH_2)_n$—N-imidazoyl, —$(CH_2)_n$-imidazoyl, —$(CH_2)_n$—N-morpholino, —$(CH_2)_n$—N-thiomorpholino, —$(CH_2)_n$—N-hexahydroazepine or substituted $C_1-C_6$ alkyl, wherein the substituents are selected from —OH, —$NH_2$, or $$—\overset{A}{\underset{|}{N}}—B,$$

A and B are independently hydrogen, $C_1-C_6$ alkyl, —$(CH_2)_n$OH, —$(CH_2)_n$—N-piperidinyl, —$(CH_2)_n$—N-piperazinyl, —$(CH_2)_n$—$N_1$-piperazinyl[$N_4$-$(C_1-C_6)$alkyl], —$(CH_2)_n$ —N-pyrrolidyl, —$(CH_2)_n$—N-pyridyl, —$(CH_2)_n$-imidazoyl, or —$(CH_2)_n$—N-imidazoyl;

$E^1$, $E^2$, or $E^3$ are independently hydrogen, halogen, $C_1-C_6$ alkyl, $C_3-C_8$ cycloalkyl, $C_1-C_6$ alkoxy, $C_3-C_8$ cycloalkoxy, nitro, $C_1-C_6$ perfluoroalkyl, hydroxy, $C_1-C_6$ acyloxy, —$NH_2$, —NH($C_1-C_6$ alkyl), —N($C_1-C_6$ alkyl)$_2$, —NH($C_3-C_8$ cycloalkyl), —N($C_3-C_8$ cycloalkyl)$_2$, hydroxymethyl, $C_1-C_6$ acyl, cyano, azido, $C_1-C_6$ thioalkyl, $C_1-C_6$ sulfinylalkyl, $C_1-C_6$ sulfonylalkyl, $C_3-C_8$ thiocycloalkyl, $C_3-C_8$ sulfinylcycloalkyl, $C_3-C_8$ sulfonylcycloalkyl, mercapto, $C_1-C_6$ alkoxycarbonyl, $C_3-C_8$ cycloalkoxycarbonyl, $C_2-C_4$ alkenyl, $C_4-C_8$ cycloalkenyl, or $C_2-C_4$ alkynyl;

$Z^a$ is a bond, —$CH_2$—, —S—, $SO_2$, —NH—, —O—, —$OCH_2$—, —S—$CH_2$—, —$SO_2$—, or —$CH_2CH_2$—;

$R^{77}$ is phenyl, substituted phenyl, or a 5- to 10-membered optionally substituted heterocyclic aromatic ring;

$R^5$ is hydrogen, halogen, $C_1$–$C_6$ perfluoroalkyl, 1,1-difluoro ($C_1$–$C_6$)alkyl, $C_1$–$C_6$ alkyl, —$(CH_2)_n$—N-piperidinyl, —$(CH_2)_n$-piperazinyl, —$(CH_2)_n$-piperazinyl[$N_4$-($C_1$–$C_6$) alkyl], —$(CH_2)_n$—N-pyrrolidyl, —$(CH_2)_n$-pyridinyl, —$(CH_2)_n$—N-imidazoyl, —$(CH_2)_n$—N-morpholino, —$(CH_2)_n$—N-thiomorpholino

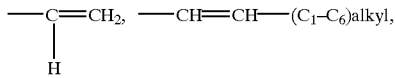

—$(CH_2)_n$—N-hexahydroazepine, —$(CH_2)_n NH_2$, —$(CH_2)_n$ $NH(C_1$–$C_6$alkyl), —$(CH_2)_n N(C_1$–$C_6$alkyl)$_2$, -1-oxo($C_1$–$C_6$)alkyl, carboxy, ($C_1$–$C_6$)alkyloxycarbonyl, N-($C_1$–$C_6$)alkylcarbamoyl, phenyl or substituted phenyl, wherein the substituted phenyl can have from one to three substituents independently selected from $E^1$, $E^2$, $E^3$ or a monocyclic heteroaryl group, and each $C_1$–$C_6$ alkyl group can be substituted with —OH, —$NH_2$ or —NAB, where A and B are as defined above; and n is 1 to 4, and the pharmaceutically acceptable salts, esters, amides, and prodrugs thereof.

In another preferred embodiment of the compounds of Formula III, Q is

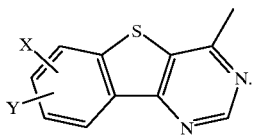

In another preferred embodiment of the compounds of Formula III, Q is

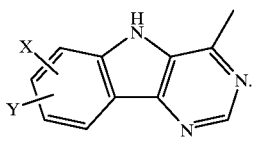

In another preferred embodiment of the compounds of Formula III, X is

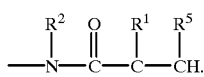

In another preferred embodiment of the compounds of Formula III, X is

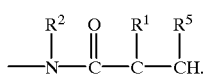

In another preferred embodiment, Q is a 6-substituted benzothieno[3,2-d]pyrmid-4-yl.

The present invention also provides a pharmaceutically acceptable composition that comprises a compound of Formula I or II.

The present invention also provides a method of treating cancer, the method comprising administering to a patient having cancer a therapeutically effective amount of a compound of Formula I or II.

The present invention also provides a method of treating or preventing restenosis, the method comprising administering to a patient having restenosis or at risk of having restenosis, a therapeutically effective amount of a compound of Formula I or II.

The present invention also provides a method of treating psoriasis, the method comprising administering to a patient having psoriasis a therapeutically effective amount of a compound of Formula I or II.

The present invention also provides a method of treating atherosclerosis, the method comprising administering to a patient having atherosclerosis a therapeutically effective amount of a compound of Formula I or II.

The present invention also provides a method of treating endometriosis, the method comprising administering to a patient having endometriosis a therapeutically effective amount of a compound of Formula I or II.

The present invention also provides a method of irreversibly inhibiting tyrosine kinases, the method comprising administering to a patient in need of tyrosine kinase inhibition a tyrosine kinase inhibiting amount of a compound of Formula I or II.

In a most preferred embodiment the present invention provides the following compounds:

N-[4-(6-Bromo-2,3-dihydroindol-1-yl)quinazolin-6-yl]acrylamide;

N-[4-(6-Chloro-2,3-dihydroindol-1-yl)quinazolin-6-yl]acrylamide;

N-[4-(7-Chloro-3,4-dihydro-2H-quinolin-1-yl)quinazolin-6-yl]acrylamide;

N-[4-(6-Chloro-2,3-dihydroindol-1-yl)quinazolin-7-yl]acrylamide;

N-[4-(7-Chloro-3,4-dihydro-2H-quinolin-1-yl)quinazolin-7-yl]acrylamide;

N-[4-(6-Chloro-2,3-dihydroindol-1-yl)quinazolin-6-yl]propynamide;

N-[4-(7-Trifluoromethyl-3,4-dihydro-2H-quinolin-1-yl)quinazolin-6-yl]propynamide;

N-[4-(6-Chloro-2,3-dihydroindol-1-yl)quinazolin-7-yl]propynamide;

N-[4-(7-Trifluoromethyl-3,4-dihydro-2H-quinolin-1-yl)quinazolin-7-yl]propynamide;

N-[4-(4-6-Chloro-2,3-dihydroindol-1-yl)quinazolin-6-yl]but-2-ynamide;

N-[4-(6-Bromo-5-fluoro-2,3-dihydroindol-1-yl)quinazolin-6-yl]but-2-ynamide;

N-[4-(6-Chloro-2,3-dihydroindol-1-yl)quinazolin-6-yl]buta-2,3-dienamide;

N-[4-(6-Bromo-5-fluoro-2,3-dihydroindol-1-yl)quinazolin-6-yl]buta-2,3-dienamide;

N-[4-(6-Chloro-2,3-dihydroindol-1-yl)quinazolin-6-yl]but-2-enamide;

N-[4-(6-Ethynyl-2,3-dihydroindol-1-yl)quinazolin-6-yl]but-2-enamide;

N-[4-(6-Chloro-2,3-dihydroindol-1-yl)quinazolin-6-yl]-4,4,4-trifluorobut-2-enamide;

N-[4-(6-Nitro-2,3-dihydroindol-1-yl)quinazolin-6-yl]-4,4,4-trifluorobut-2-enamide;

N-[4-(6-Chloro-2,3-dihydroindol-1-yl)quinazolin-6-yl]-3-chloroacryl-amide;

N-[4-(6-Nitro-2,3-dihydroindol-1-yl)quinazolin-6-yl]-3-chloroacrylamide;

6-(S-Vinylsulfonamido)-4-(6-chloro-2,3-dihydroindol-1-yl)quinazoline;

6-(S-Vinylsulfonamido)-4-(6-pyrrol-1-yl-2,3-dihydroindol-1-yl)quinazoline;

N-[7-[3-(4-Morpholino)propoxy]-4-(6-chloro-2,3-dihydroindol-1-yl)quinazolin-6-yl]acrylamide;
N-[4-(6-Pyrrol-1-yl-2,3-dihydroindol-1-yl)-7-[4-(N,N-dimethylamino)butoxy]quinazolin-6-yl]acrylamide
N-[7-[4-(N,N-dimethylamino)butoxy]-4-(6-chloro-2,3-dihydroindol-1-yl)quinazolin-6-yl]acrylamide;
N-[4-(Octahydroindol-1-yl)-7-[3-(4-morpholino)propoxy]quinazolin-6-yl]acrylamide;
N-[4-(6-Chloro-2,3-dihydroindol-1-yl)quinazolin-6-yl]-4-oxopent-2-enamide;
N-[4-(Octahydroindol-1-yl)quinazolin-6-yl]-4-oxopent-2-enamide;
N-[4-(6-Chloro-2,3-dihydroindol-1-yl)quinazolin-6-yl]-4-hydroxy-4-oxobut-2-enamide;
N-[4-(6,7-Dihydro-5H-[1,3]dioxolo[4,5-f]indol-5-yl)quinazolin-6-yl]-4-hydroxy-4-oxobut-2-enamide;
N-[4-(6-Chloro-2,3-dihydroindol-1-yl)quinazolin-6-yl]-4-ethoxy-4-oxobut-2-enamide;
N-[4-(6,7-Dihydro-5H-[1,3]dioxolo[4,5-f]indol-5-yl)quinazolin-6-yl]-4-ethoxy-4-oxobut-2-enamide;
N-[4-(6-Chloro-2,3-dihydroindol-1-yl)quinazolin-6-yl]-4-(3-(N,N-dimethylamino)propoxy)-4-oxobut-2-enamide;
N-[4-(6-Methyl-2,3-dihydroindol-1-yl)quinazolin-6-yl]-4-(3-(N,N-dimethylamino)propoxy)-4-oxobut-2-enamide;
N-[4-(6-Chloro-2,3-dihydroindol-1-yl)quinazolin-6-yl]-4-(3-(N,N-dimethylamino)propylamino)-4-oxobut-2-enamide;
N-[4-(6-Methyl-2,3-dihydroindol-1-yl)quinazolin-6-yl]-4-(3-(N,N-dimethylamino)propylamino)-4-oxobut-2-enamide;
N-[4-(6-Chloro-2,3-dihydroindol-1-yl)quinazolin-6-yl]-4-(3-(4-morpholino)propoxy)-4-oxobut-2-enamide;
N-[4-(6-Azido-2,3-dihydroindol-1-yl)quinazolin-6-yl]-4-(3-(4-morpholino)propoxy)-4-oxobut-2-enamide;
N-[4-(6-Chloro-2,3-dihydroindol-1-yl)quinazolin-6-yl]4-(3-(4-morpholino)propylamino)4-oxobut-2-enamide;
N-[4-(6-Azido-2,3-dihydroindol-1-yl)quinazolin-6-yl]-4-(3-(4-morpholino)propylamino)-4-oxobut-2-enamide;
4,4-Difluoro-8-(morpholin-4-yl)oct-2-enoic acid [4-(6-chloro-2,3-dihydroindol-1-yl)quinazolin-6-yl]amide;
4,4-Difluoro-8-(morpholin-4-yl)oct-2-enoic acid [4-(5-benzyloxy-2,3-dihydroindol-1-yl)quinazolin-6-yl]amide;
Pent-2-enedioic acid 1{[4-(5-benzyloxy-2,3-dihydroindol-1-yl)quinazolin-6-yl]amide}5-[(3-morpholin-4-ylpropyl)amide];
Pent-2-enedioic acid 1 {[4-(6-chloro-2,3-dihydroindol-1-yl)quinazolin-6-yl]amide}5-[(3-morpholin-4-ylpropyl)amide];
N-[4-(6-Chloro-2,3-dihydroindol-1-yl)quinazolin-6-yl]4-(3-(morpholin-4-yl)propylthio)but-2-enamide;
N-[4-(5-Methoxy-2,3-dihydroindol-1-yl)quinazolin-6-yl]-4,-(3-(morpholin-4-yl)propylthio)but-2-enamide;
7-Morpholin-4-ylhept-2-ynoic acid [4-(6-chloro-2,3-dihydroindol-1-yl)quinazolin-6-yl]amide;
7-Morpholin-4-ylhept-2-ynoic acid [4-(5-methoxy-2,3-dihydroindol-1-yl)quinazolin-6-yl]amide;
4-Morpholin-4-ylbut-2-ynoic acid [4-(6-chloro-2,3-dihydroindol-1-yl)quinazolin-6-yl]amide;
4-Morpholin-4-ylbut-2-ynoic acid [4-(2,3,4,5-tetrahydro-1H-benzoazepin-1-yl)quinazolin-6-yl]amide;
N-[4-(6-Chloro-2,3-dihydroindol-1-yl)pyrido[3,4-d]pyrimid-6-yl]acrylamide;
N-[4-(2,3,4,5-Tetrahydro-1H-benzoazepin-1-yl)pyrido[3,4-d]pyrimid-6-yl]acrylamide;
N-[4-(6-Chloro-2,3-dihydroindol-1-yl)pyrido[4,3-d]pyrimid-7-yl]acrylamide;
N-[4-(5-Hydroxy-2,3-dihydroindol-1-yl)pyrido[4,3-d]pyrimid-7-yl]propynamide;
N-[4-(6-Chloro-2,3-dihydroindol-1-yl)pyrido[3,4-d]pyrimid-6-yl]propynamide;
N-[4-(5-Hydroxy-2,3-dihydroindol-1-yl)pyrido[3,4-d]pyrimid-6-yl]propynamide;
N-[4-(6-Chloro-2,3-dihydroindol-1-yl)pyrido[4,3-d]pyrimid-7-yl]propynamide;
N-[4-(5-Amino-2,3-dihydroindol-1-yl)pyrido[4,3-d]pyrimid-7-yl]propynamide;
N-[4-(6-Chloro-2,3-dihydroindol-1-yl)pyrido[3,4-d]pyrimid-6-yl]but-2-ynamide;
N-[4-(5-Amino-2,3-dihydroindol-1-yl)pyrido[3,4-d]pyrimid-6-yl]but-2-ynamide;
N-[4-(6-Chloro-2,3-dihydroindol-1-yl)pyrido[3,4-d]pyrimid-6-yl]buta-2,3-dienamide;
N-[4-(1,2,3,4,5,6-Hexahydrobenzo[b]azocin-1-yl)pyrido[3,4-d]pyrimid-6-yl]buta-2,3-dienamide;
N-[4-(6-Chloro-2,3-dihydroindol-1-yl)pyrido[3,4-d]pyrimid-6-yl]but-2-enamide;
N-[4-(1,2,3,4,5,6-Hexahydrobenzo[b]azocin-1-yl)pyrido[3,4-d]pyrimid-6-yl]but-2-enamide;
N-[4-(6-Chloro-2,3-dihydroindol-1-yl)pyrido[3,4-d]pyrimid-6-yl]-4,4,4-trifluorobut-2-enamide;
N-[4-(6-Fluoro-7-methyl-2,3-dihydroindol-1-yl)pyrido[3,4-d]pyrimid-6-yl]-4,4,4-trifluorobut-2-enamide;
N-[4-(6-Chloro-2,3-dihydroindol-1-yl)pyrido[3,4-d]pyrimid-6-yl]-3-chloroacrylamide;
N-[4-(6-Fluoro-7-methyl-2,3-dihydroindol-1-yl)pyrido[3,4-d]pyrimid-6-yl]-3-chloroacrylamide;
6-(S-Vinylsulfonamido)-4-(6-chloro-2,3-dihydroindol-1-yl)pyrido[3,4-d]pyrimidine;
6-(S-Vinylsulfonamido)4-(2,3,6,7,8,9-hexahydro-1H-benzo[g]indol 1-yl)pyrido[3,4-d]pyrimidine;
N-[4-(6-Chloro-2,3-dihydroindol-1-yl)pyrido[3,4-d]pyrimid-6-yl]-4-oxopent-2-enamide;
N-[4-(2,3,6,7,8,9-Hexahydro-1H-benzo[g]indol-1-yl)pyrido[3,4-d]pyrimid-6-yl]-4-oxopent-2-enamide;
N-[4-(6-Chloro-2,3-dihydroindol-1-yl)pyrido[3,4-d]pyrimid-6-yl]-4-hydroxy-4-oxobut-2-enamide;
N-[4-(6-Ethynyl-2,3-dihydroindol-1-yl)pyrido[3,4-d]pyrimid-6-yl]-4-hydroxy-4-oxobut-2-enamide;
N-[4-(6-Chloro-2,3-dihydroindol-1-yl)pyrido[3,4-d]pyrimid-6-yl]-4-ethoxy-4-oxobut-2-enamide;
N-[4-(6-Ethynyl-2,3-dihydroindol-1-yl)pyrido[3,4-d]pyrimid-6-yl]-4-ethoxy-4-oxobut-2-enamide;
N-[4-(6-Chloro-2,3-dihydroindol-1-yl)pyrido[3,4-d]pyrimid-6-yl]-4-(3-(N,N-dimethylamino)propoxy)-4-oxobut-2-enamide;
N-[4-(6-Ethynyl-2,3-dihydroindol-1-yl)pyrido[3,4-d]pyrimid-6-yl]-4-(3-(N,N-dimethylamino)propoxy)-4-oxobut-2-enamide;
N-[4-(6-Chloro-2,3-dihydroindol-1-yl)pyrido[3,4-d]pyrimid-6-yl]-4-(3-(N,N-dimethylainino)propylamino)-4-oxobut-2-enamide;
N-[4-(6-Ethynyl-2,3-dihydroindol-1-yl)pyrido[3,4-d]pyrimid-6-yl]-4-(3-(N,N-dimethylamino)propylamino)-4-oxobut-2-enamide;

N-[4-(6-Chloro-2,3-dihydroindol-1-yl)pyrido[3,4-d]
pyrimid-6-yl]-4-(3-(4-morpholino)propoxy)4-oxobut-
2-enamide;

N-[4-(6-Ethynyl-2,3-dihydroindol-1-yl)pyrido[3,4-d]
pyrimid-6-yl]-4-(3-(4-morpholino)propoxy)-4-oxobut-
2-enamide;

N-[4-(6-Chloro-2,3-dihydroindol-1-yl)pyrido[3,4-d]
pyrimid-6-yl]-4-(3-(4-morpholino)propylamino)-4-
oxobut-2-enamide;

N-[4-(6-Ethynyl-2,3-dihydroindol-1-yl)pyrido[3,4-d]
pyrimid-6-yl]-4-(3-(4-morpholino)propylamino)-4-
oxobut-2-enamide;

4,4-Difluoro-8-(morpholin-4-yl)oct-2-enoic acid [4-(6-
chloro-2,3-dihydroindol-1-yl)pyrido[3,4-d]pyrimid-6-
yl]amide;

4,4-Difluoro-8-(morpholin-4-yl)oct-2-enoic acid [4-(6-
Ethynyl-2,3-dihydroindol-1-yl)pyrido[3,4-d]pyrimid-
6-yl]amide;

Pent-2-enedioic acid 1{[4-(2,3-dihydroindol[2,3-f]indol-
7-yl)pyrido[3,4-d]pyrimid-6-yl]amide}5-[(3-
morpholin-4-ylpropyl)amide];

Pent-2-enedioic acid 1{[4-(6-chloro-2,3-dihydroindol-1-
yl)pyrido[3,4-d]pyrimid-6-yl]amide}5-[(3-morpholin-
4-ylpropyl)amide];

N-[4-(6-Chloro-2,3-dihydroindol-1-yl)pyrido[3,4-d]
pyrimid-6-yl]-4-(3-(morpholin-4-yl)propylthio)but-2-
enamide;

N-[4-(2,3-Dihydropyrrolo[2,3-f]indol-7-yl)pyrido[3,4-d]
pyrimid-6-yl]-4-(3-(morpholin-4-yl)propylthio)but-2-
enamide;

7-Morpholin-4-ylhept-2-ynoic acid [4-(6-chloro-2,3-
dihydroindol-1-yl)pyrido[3,4-d]pyrimid-6-yl]amide;

7-Morpholin-4-ylhept-2-ynoic acid [4-(2,3,5,6-
tetrahydropyrrolo[2,3-f]indol-1-yl)pyrido[3,4-d]
pyrimid-6-yl]amide;

4-Morpholin-4-ylbut-2-ynoic acid [4-(6-chloro-2,3-
dihydroindol-1-yl)pyrido[3,4-d]pyrimid-6-yl]amide;

4-Morpholin-4-ylbut-2-ynoic acid [4-(2,3,5,6-
tetrahydropyrrolo[2,3-f]indol-1-yl)pyrido[3,4-d]
pyrimid-6-yl]amide;

N-[4-(6-Chloro-2,3-dihydroindol-1-yl)benzo[b]thieno[3,
2-d]pyrimid-6-yl]acrylamide;

N-[4-(6-Ethynyl-2,3-dihydroindol-1-yl)benzo[b]thieno
[3,2-d]pyrimid-6-yl]acrylamide;

[4-(6-Chloro-2,3-dihydroindol-1-yl)quinazolin-6-yl]
acrylate;

[4-(2,3,5,6-Tetrahydropyrrolo[2,3-f]indol-1-yl)
quinazolin-6-yl]acrylate;

[4-(6-Chloro-2,3-dihydroindol-1-yl)quinazolin-7-yl]
acrylate;

[4-(6-Ethynyl-2,3-dihydroindol-1-yl)quinazolin-7-yl]
acrylate;

[7-[3-(4-Morpholino)propoxy]-4-(6-chloro-2,3-
dihydroindol-1-yl)quinazolin-6-yl]acrylate;

[4-(-(2,3-Dihydropyrrolo[2,3-f]indol-7-yl)-7-[4-(N,N-
dimethylamino)butoxy]quinazolin-6-yl]acrylate;

[7-[4-(N,N-dimethylamino)butoxy]-4-(6-chloro-2,3-
dihydroindol-1-yl)quinazolin-6-yl]acrylate;

[4-(6-Ethynyl-2,3-dihydroindol-1-yl)-7-[3-(4-
morpholino)propoxy]quinazolin-6-yl]acrylate;

N-(3-(4-Morpholino)propylamino)-4,O-[4-(6-chloro-2,3-
dihydroindol-1-yl)quinazolin-6-yl]-4-oxobut-2-
enamide;

N-(3-(4-Morpholino)propylamino)-4,O-[4-(2,3,4,5-
tetrahydro-1H-benzoazepin-1-yl)quinazolin-6-yl]4-
oxobut-2-enamide;

4,4-Difluoro-8-(morpholin-4-yl)oct-2-enoic acid [4-(6-
chloro-2,3-dihydroindol-1-yl)quinazolin-6-yl]ester;

4,4-Difluoro-8-(morpholin-4-yl)oct-2-enoic acid [4-(6-
bromo-2,3-dihydroindol-1-yl)quinazolin-6-yl]ester;

Pent-2-enedioic acid 1{[4-(6-methyl-2,3-dihydroindol-1-
yl)quinazolin-6-yl]ester}5-[(3-morpholin-4-ylpropyl)
amide];

Pent-2-enedioic acid 1{[4-(6-chloro-2,3-dihydroindol-1-
yl)quinazolin-6-yl]ester}5-[(3-morpholin-4-ylpropyl)
amide];

[4-(6-Chloro-2,3-dihydroindol-1-yl)quinazolin-6-yl]-4-
(3-(morpholin-4-yl)propylthio)but-2-enoate;

[4-(6-Fluoro-2,3-dihydroindol-1-yl)quinazolin-6-yl]-4-
(3-(morpholin-4-yl)propylthio)but-2-enoate;

7-Morpholin-4-ylhept-2-ynoic acid [4-(6-chloro-2,3-
dihydroindol-1-yl)quinazolin-6-yl]ester;

7-Morpholin-4-ylhept-2-ynoic acid [4-(6-chloro-7-
fluoro-2,3-dihydroindol-1-yl)quinazolin-6-yl]ester;

4-Morpholin-4-ylbut-2-ynoic acid [4-(6-chloro-2,3-
dihydroindol-1-yl)quinazolin-6-yl]ester;

4-Morpholin-4-ylbut-2-ynoic acid [4-(6-ethynyl-2,3-
dihydroindol-1-yl)quinazolin-6-yl]ester;

N-[4-(Quinol-2-ylamino)quinazolin-6-yl]acrylamide;

N-[4-(Indol-5-ylamino)quinazolin-6-yl]acrylamide;

N-[4-(Quinol-2-ylamino)quinazolin-7-yl]acrylamide;

N-[4-(Indol-5-ylamino)quinazolin-7-yl]acrylamide;

N-[4-(Quinol-3-ylamino)quinazolin-6-yl]propynamide;

N-[4-(Indol-5-ylamino)quinazolin-6-yl]propynamide;

N-[4-(Quinol-3-ylamino)quinazolin-7-yl]propynamide;

N-[4-(Indol-5-ylamino)quinazolin-7-yl]propynamide;

N-[4-(Quinol-5-ylamino)quinazolin-6-yl]but-2-ynamide;

N-[4-(Indol-5-ylamino)quinazolin-6-yl]but-2-ynamide;

N-[4-(Quinol-5-ylamino)quinazolin-6-yl]buta-2,3-
dienamide;

N-[4-(Indol-5-ylamino)quinazolin-6-yl]buta-2,3-
dienamide;

N-[4-(Quinol-6-ylamino)quinazolin-6-yl]but-2-enamide;

N-[4-(Indol-5-ylamino)quinazolin-6-yl]but-2-enamide;

N-[4-(Quinol-6-ylamino)quinazolin-6-yl]-4,4,4-
trifluorobut-2-enamide;

N-[4-(Indol-5-ylamino)quinazolin-6-yl]-4,4,4-
trifluorobut-2-enamide;

N-[4-(Quinol-7-ylamino)quinazolin-6-yl]-3-
chloroacrylamide;

N-[4-(Indol-5-ylamino)quinazolin-6-yl]-3-
chloroacrylamide;

6-(S-Vinylsulfonamido)-4-(quinol-7-ylamino)
quinazoline;

6-(S-Vinylsulfonamido)-4-(indol-5-ylamino)quinazoline;

N-[7-[3-(4-Morpholino)propoxy]-4-(quinol-8-ylamino)
quinazolin-6-yl]acrylamide;

N-[4-(Indol-5-ylamino)-7-[4-(N,N-dimethylamino)
butoxy]quinazolin-6-yl]acrylamide;

N-[7-[4-(N,N-dimethylamino)butoxy]-4-(quinol-8-
ylamino)quinazolin-6-yl]acrylamide;

N-[4-(Indol-5-ylamino)-7-[3-(4-morpholino)propoxy]
quinazolin-6-yl]acrylamide;

N-[4-(Isoquinol-1-ylamino)quinazolin-6-yl]-4-oxopent-
2-enamide;

N-[4-(Indol-5-ylamino)quinazolin-6-yl]-4-oxopent-2-enamide;
N-[4-(Isoquinol-1-ylamino)quinazolin-6-yl]4-hydroxy-4-oxobut-2-enainide;
N-[4-(Indol-5-ylamino)quinazolin-6-yl]-4-hydroxy-4-oxobut-2-enamide;
N-[4-(Isoquinol-5-ylamino)quinazolin-6-yl]-4-ethoxy-4-oxobut-2-enamide;
N-[4-(Indol-5-ylamino)quinazolin-6-yl]-4-ethoxy-4-oxobut-2-enamide;
N-[4-(Isoquinol-5-ylamino)quinazolin-6-yl]-4-(3-(N,N-dimethylamino)propoxy)-4-oxobut-2-enamide;
N-[4-(Indol-5-ylamino)quinazolin-6-yl]-4-(3-(N,N-dimethylamino)propoxy)-4-oxobut-2-enamide;
N-[4-(Indol4-ylamino)quinazolin-6-yl]-4-(3-(N,N-dimethylamino)propylamino)4-oxobut-2-enamide;
N-[4-(Indol-5-ylamino)quinazolin-6-yl]-4-(3-(N,N-dimethylamino)propylamino)-4-oxobut-2-enamide;
N-[4-(Indol-4-ylamino)quinazolin-6-yl]-4-(3-(4-morpholino)propoxy)-4-oxobut-2-enamide;
N-[4-(Indol-5-ylamino)quinazolin-6-yl]-4-(3-(4-morpholino)propoxy)-4-oxobut-2-enamide;
N-[4-(Indol-6-ylamino)quinazolin-6-yl]-4-(3-(4-morpholino)propylamino)-4-oxobut-2-enamide;
N-[4-(Indol-5-ylamino)quinazolin-6-yl]-4-(3-(4-morpholino)propylamino)-4-oxobut-2-enamide;
4,4-Difluoro-8-(morpholin-4-yl)oct-2-enoic acid [4-(indol-6-ylamino)quinazolin-6-yl]amide;
4,4-Difluoro-8-(morpholin-4-yl)oct-2-enoic acid [4-(indol-5-ylamino)quinazolin-6-yl]amide;
Pent-2-enedioic acid 1{[4-(indol-5-ylamino)quinazolin-6-yl]amide}5-[(3-morpholin-4-ylpropyl)amide];
Pent-2-enedioic acid 1{[4-(1H-indazol-6-ylamino)quinazolin-6-yl]amide}5-[(3-morpholin-4-ylpropyl)amide];
N-[4-(1H-Indazol-6-ylamino)quinazolin-6-yl]-4-(3-(morpholin-4-yl)propylthio)but-2-enamide;
N-[4-(Indol-5-ylamino)quinazolin-6-yl]-4-(3-(morpholin-4-yl)propylthio)but-2-enamide;
7-Morpholin-4-ylhept-2-ynoic acid [4-(1H-indazol-5-ylamino)quinazolin-6-yl]amide;
7-Morpholin-4-ylhept-2-ynoic acid [4-(indol-5-ylamino)quinazolin-6-yl]amide;
4-Morpholin-4-ylbut-2-ynoic acid [4-(1H-indazol-5-ylamino)quinazolin-6-yl]amide;
4-Morpholin-4-ylbut-2-ynoic acid [4-(4-benzyloxyphenylamino)quinazolin-6-yl]amide;
N-[4-(1H-Indazol-4-ylamino)pyrido[3,4-d]pyrimid-6-yl]acrylamide;
N-[4-(Indol-5-ylamino)pyrido [3,4-d]pyrimid-6-yl]acylamide;
N-[4-(1H-Indazol -4-ylamino)pyrido[4,3-d]pyrimid-7-yl]acrylamide;
N-[4-(Indol-5-ylamino)pyrido[4,3-d]pyrimid-7-yl]propynamide;
N-[4-(1H-Indazol-4-ylamino)pyrido[3,4-d]pyrimid-6-yl]propynamide;
N-[4-(Indol-5-ylamino)pyrido[3,4-d]pyrimid-6-yl]propynamide;
N-[4-(1H-Benzotriazol-5-ylamino)pyrido[4,3-d]pyrimid-7-yl]propynamide;
N-[4-(Indol-5-ylamino)pyrido[4,3-d]pyrimid-7-yl]propynamide;
N-[4-(1H-Benzotriazol-5-ylamino)pyrido[3,4-d]pyrimid-6-yl]but-2-ynamide;
N-[4-(Indol-5-ylamino)pyrido[3,4-d]pyrimid -6-yl]but-2-ynamide;
N-[4-(1H-Benzotriazol-5-ylamino)pyrido[3,4-d]pyrimid-6-yl]buta-2,3-dienamide;
N-[4-(Indol-5-ylamino)pyrido[3,4-d]pyrimid-6-yl]buta-2,3-dienamide;
N-[4-(1H-Benzotriazol-7-ylamino)pyrido[3,4-d]pyrimid-6-yl]but-2-enamide;
N-[4-(Indol-5-ylamino)pyrido[3,4-d]pyrimid -6-yl]but-2-enamide;
N-[4-(1H-Benzotriazol-7-ylamino)pyrido[3,4-d]pyrimid-6-yl]-4,4,4-trifluorobut-2-enamide;
N-[4-(Indol-5-ylamino)pyrido[3,4-d]pyrimid-6-yl]-4,4,4-trifluorobut-2-enamide;
N-[4-(1H-Benzotriazol-7-ylamino)pyrido[3,4-d]pyrimid-6-yl]-3-chloroacrylamide;
N-[4-(Indol-5-ylamino)pyrido[3,4-d]pyrimid-6-yl]-3-chloroacrylamide;
6-(S-Vinylsulfonamido)-4-(benzothiazol-5-ylamino)pyrido[3,4-d]-pyrimidine;
6-(S-Vinylsulfonamido)-4-(indol-5-ylamino)pyrido[3,4-d]pyrimidine;
N-[4-(Benzothiazol-5-ylamino)pyrido[3,4-d]pyrimid-6-yl]-4-oxopent-2-enamide;
N-[4-(Indol-5-ylamino)pyrido[3,4-d]pyrimid-6-yl]-4-oxopent-2-enamide;
N-[4-(Benzothiazol-6-ylamino)pyrido[3,4-d]pyrimid-6-yl]-4-hydroxy-4-oxobut-2-enamide;
N-[4-(Indol-5-ylamino)pyrido[3,4-d]pyrimid-6-yl]-4-hydroxy-4-oxobut-2-enamide;
N-[4-(Benzothiazol-6-ylamino)pyrido[3,4-d]pyrimid-6-yl]-4-ethoxy-4-oxobut-2-enamide;
N-[4-(Indol-5-ylamino)pyrido[3,4-d]pyrimid-6-yl]-4-ethoxy-4-oxobut-2-enamide;
N-[4-(Indan-4-ylamino)pyrido[3,4-d]pyrimid-6-yl]-4-(3-(N,N-dimethylamino)propoxy)-4-oxobut-2-enamide;
N-[4-(Indol-5-ylamino)pyrido[3,4-d]pyrimid-6-yl]-4-(3-(N,N-dimethylamino)propoxy)-4-oxobut-2-enamide;
N-[4-(Indan-4-ylamino)pyrido[3,4-d]pyrimid-6-yl]-4-(3-(N,N-dimethylamino)propylamino)-4-oxobut-2-enamide;
N-[4-(Indol-5-ylamino)pyrido[3,4-d]pyrimid-6-yl]-4-(3-(N,N-dimethylamino)propylamino)-4-oxobut-2-enamide;
N-[4-(Indan-5-ylamino)pyrido[3,4-d]pyrimid-6-yl]-4-(3-(4-morpholino)propoxy)-4-oxobut-2-enamide;
N-[4-(Indol-5-ylamino)pyrido[3,4-d]pyrimid-6-yl]-4-(3-(4-morpholino)propoxy)-4-oxobut-2-enamide;
N-[4-(Indan-5-ylamino)pyrido[3,4-d]pyrimid-6-yl]-4-(3-(4-morpholino)propylamino)-4-oxobut-2-enamide;
N-[4-(Indol-5-ylamino)pyrido[3,4-d]pyrimid-6-yl]-4-(3-(4-morpholino)propylamino)-4-oxobut-2-enamide;
4,4-Difluoro-8-(morpholin-4-yl)oct-2-enoic acid [4-(1,2,3,4-tetrahydronaphth-1-ylamino)pyrido[3,4-d]pyrimid-6-yl]amide;
4,4-Difluoro-8-(morpholin-4-yl)oct-2-enoic acid [4-(indol-5-ylamino)pyrido[3,4-d]pyrimid-6-yl]amide;
Pent-2-enedioic acid 1{[4-(indol-5-ylamino)pyrido[3,4-d]pyrimid-6-yl]amide}5-[(3-morpholin-4-ylpropyl)amide];

Pent-2-enedioic acid 1{[4-(1,2,3,4-tetrahydronaphth-1-ylamino)pyrido[3,4-d]pyrimid-6-yl]amide}5-[(3-morpholin-4-ylpropyl)amide];

N-[4-(1,2,3,4-Tetrahydronaphth-2-ylamino)pyrido[3,4-d]pyrimid-6-yl]-4-(3-(morpholin-4-yl)propylthio)but-2-enamide;

N-[4-(Indol-5-ylamino)pyrido[3,4-d]pyrimid-6-yl]-4-(3-(morpholin-4-yl)propylthio)but-2-enamide;

7-Morpholin-4-ylhept-2-ynoic acid [4-(1,2,3,4-tetrahydronaphth-2-ylamino)pyrido[3,4-d]pyrimid-6-yl]amide;

7-Morpholin-4-ylhept-2-ynoic acid [4-(indol-5-ylamino)pyrido[3,4-d]pyrimid-6-yl]amide;

4-Morpholin-4-ylbut-2-ynoic acid [4-(benzo[c][2,1,3]thiadiazol-4-ylamino)pyrido[3,4-d]pyrimid-6-yl]amide;

4-Morpholin-4-ylbut-2-ynoic acid [4-(indol-5-ylamino)pyrido[3,4-d]pyrimid-6-yl]amide;

N-[4-(Benzo[c][2,1,3]thiadiazol-4-ylamino)benzo[b]thieno[3,2-d]pyrimid-6-yl]acrylamide;

N-[4-(Indol-5-ylamino)benzo[b]thieno[3,2-d]pyrimid-6-yl]acrylamide;

[4-(Benzimidazol-5-ylamino)quinazolin-6-yl]acrylate;

[4-(Indol-5-ylamino)quinazolin-6-yl]acrylate;

[4-(Benzimidazol-5-ylamino)quinazolin-7-yl]acrylate;

[4-(Indol-5-ylamino)quinazolin-7-yl]acrylate;

[7-[3-(4-Morpholino)propoxy]-4-(benzimidazol-5-ylamino)quinazolin-6-yl]acrylate;

[4-(Indol-5-ylamino)-7-[4-(N,N-dimethylamino)butoxy]quinazolin-6-yl]acrylate;

[7-[4-(N,N-dimethylamino)butoxy]-4-(6-methoxyquinol-8-ylamino)quinazolin-6-yl]acrylate;

[4-(Indol-5-ylamino)-7-[3-(4-morpholino)propoxy]quinazolin-6-yl]acrylate;

N-(3-(4-Morpholino)propylamino)-4,O-[4-(6-methoxyquinol-8-ylamino)quinazolin-6-yl]-4-oxobut-2-enamide;

N-(3-(4-Morpholino)propylamino)-4,O-[4-(indol-5-ylamino)quinazolin-6-yl]-4-oxobut-2-enamide;

4,4-Difluoro-8-(morpholin-4-yl)oct-2-enoic acid [4-(1-methylindol-5-ylamino)quinazolin-6-yl]ester;

4,4-Difluoro-8-(morpholin-4-yl)oct-2-enoic acid [4-(indol-5-ylamino)quinazolin-6-yl]ester;

Pent-2-enedioic acid 1{[4-(indol-5-ylamino)quinazolin-6-yl]ester}5-[(3-morpholin-4-ylpropyl)amide];

Pent-2-enedioic acid 1{[4-(1-methylindol-5-ylamino)quinazolin-6-yl]ester}5-[(3-morpholin-4-ylpropyl)amide];

[4-(2-Methylindol-5-ylamino)quinazolin-6-yl]-4-(3-(morpholin-4-yl)propylthio)but-2-enoate;

[4-(Indol-5-ylamino)quinazolin-6-yl]-4-(3-(morpholin-4-yl)propylthio)but-2-enoate;

7-Morpholin-4-ylhept-2-ynoic acid [4-(3-cyanoindol-5-ylamino)quinazolin-6-yl]ester;

7-Morpholin-4-ylhept-2-ynoic acid [4-(indol-5-ylamino)quinazolin-6-yl]ester;

4-Morpholin-4-ylbut-2-ynoic acid [4-(benzothien-5-ylamino)quinazolin-6-yl]ester;

4-Morpholin-4-ylbut-2-ynoic acid [4-(indol-5-ylamino)quinazolin-6-yl]ester;

N-[4-(1-Benzylindol-5-ylamino)quinazolin-6-yl]acrylamide;

N-[4-(2-Benzylbenzimidazol-5-ylamino)quinazolin-6-yl]acrylamide;

N-[4-(1-Benzylindol-5-ylamino)quinazolin-7-yl]acrylamide;

N-[4-(2-Benzylbenzimidazol-5-ylamino)quinazolin-7-yl]acrylamide;

N-[4-(2-Benzylbenzindazol-5-ylamino)quinazolin-6-yl]propynamide;

N-[4-(1-Benzylbenzindazol-5-ylamino)quinazolin-6-yl]propynamide;

N-[4-(2-Benzylbenzindazol-5-ylamino)quinazolin-7-yl]propynamide;

N-[4-(2-Benzylbenzindazol-5-ylamino)quinazolin-7-yl]propynamide;

N-[4-(1-Phenylsulfonylindol-5-ylamino)quinazolin-6-yl]but-2-ynamide;

N-[4-(1-Phenylsulfonylindol-5-ylamino)quinazolin-6-yl]buta-2,3-dienamide;

N-[4-(1-Benzylindol-5-ylamino)quinazolin-6-yl]but-2-enamide;

N-[4-(2-Benzylbenzindazol-5-ylamino)quinazolin-6-yl]-4,4,4-trifluorobut-2-enamide;

N-[4-(1-Benzylindol-5-ylamino)quinazolin-6-yl]-4,4,4-trifluorobut-2-enamide;

N-[4-(1-Benzylindol-6-ylamino)quinazolin-6-yl]-3-chloroacrylamide;

6-(S-Vinylsulfonamido)-4-(2-benzylbenzindazol-5-ylamino)quinazoline;

N-[7-[3-(4-Morpholino)propoxy]-4-(2-benzylbenzindazol-5-ylamino)quinazolin-6-yl]acrylaide;

N-[4-(1-Benzylindol-6-ylamino)-7-[4-(N,N-dimethylamino)butoxy]-quinazolin-6-yl]acrylamide;

N-[4-(2-Phenylbenzimidazol-5-ylamino)-7-[3-(4-morpholino)propoxy]-quinazolin-6-yl]acrylamide;

N-[4-(2-Phenylbenzimidazol-5-ylamino)quinazolin-6-yl]-4-oxopent-2-enamide;

N-[4-(3-Benzylbenzimidazol-5-ylamino)quinazolin-6-yl]-4-hydroxy-4-oxobut-2-enamide;

N-[4-(3-Benzylbenzimidazol-5-ylamino)quinazolin-6-yl]-4-ethoxy-4-oxobut-2-enamide;

N-[4-(2-Benzylbenzindazol-5-ylamino)quinazolin-6-yl]-4-(3-(N,N-dimethylamino)propoxy)-4-oxobut-2-enamide;

N-[4-(2-Benzylbenzindazol-5-ylamino)quinazolin-6-yl]-4-(3-(N,N-dimethylamino)propylamino)-4-oxobut-2-enamide;

N-[4-(1-Benzylbenzimidazol-5-ylamino)quinazolin-6-yl]-4-(3-(N,N-dimethylamino)propylamino)-4-oxobut-2-enamide;

N-[4-(1-Benzylbenzimidazol-5-ylamino)quinazolin-6-yl]-4-(3-(4-morpholino)propoxy)-4-oxobut-2-enamide;

N-[4-(2-Benzylbenzindazol-5-ylamino)quinazolin-6-yl]-4-(3-(4-morpholino)propoxy)4-oxobut-2-enamide;

N-[4-(42-Benzylbenzindazol-5-ylamino)quinazolin-6-yl]-4-(3-(4-morpholino)propylamino)-4-oxobut-2-enainide;

N-[4-(2-Benzylbenzotriazol-5-ylamino)quinazolin-6-yl]-4-(3-(4-morpholino)propylamino)-4-oxobut-2-enamide;

4,4-Difluoro-8-(morpholin-4-yl)oct-2-enoic acid [4-(2-benzylbenzotriazol-5-ylamino)quinazolin-6-yl]amide;

4,4-Difluoro-8-(morpholin-4-yl)oct-2-enoic acid [4-(2-benzylbenzindazol-5-ylamino)quinazolin-6-yl]amide;

Pent-2-enedioic acid 1{[4-(2-benzylbenzindazol-5-ylamino)quinazolin-6-yl]amide}5-[(3-morpholin-4-ylpropyl)amide];

Pent-2-enedioic acid 1{[4-(2-benzylbenzindazol-5-ylamino)quinazolin-6-yl]amide}5-[(3-morpholin-4-ylpropyl)amide];

N-[4-(1-Benzylbenzotriazol-5-ylamino)quinazolin-6-yl]-4-(3-(morpholin-4-yl)propylthio)but-2-enamide;

N-[4-(2-Benzylbenzindazol-5-ylamino)quinazolin-6-yl]-4-(3-(morpholin-4-yl)propylthio)but-2-enamide;

7-Morpholin-4-ylhept-2-ynoic acid [4-(1-Benzylbenzotriazol-5-ylamino)quinazolin-6-yl]amide;

4-Morpholin-4-ylbut-2-ynoic acid [4-(3-benzylbenzotriazol-5-ylamino)quinazolin-6-yl]amide;

4-Morpholin-4-ylbut-2-ynoic acid [4-(2-benzylbenzindazol-5-ylamino)quinazolin-6-yl]amide;

N-[4-(2-Benzylbenzindazol-5-ylamino)pyrido[3,4-d]pyrimid-6-yl]acrylamide;

N-[4-(3-Benzylbenzotriazol-5-ylamino)pyrido[3,4-d]pyrimid-6-yl]acrylamide;

N-[4-(2-{Pyrid-2-yl}benzotriazol-5-ylamino)pyrido[3,4-d]pyrimid-6-yl]propynamide;

N-[4-(2-Benzylbenzindazol-5-ylamino)pyrido[3,4-d]pyrimid-6-yl]propynamide;

N-[4-(2-{Pyrid-2-yl}benzotriazol-5-ylamino)pyrido[3,4-d]pyrimid-6-yl]but-2-ynamide;

N-[4-(2-Benzylbenzindazol-5-ylamino)pyrido[3,4-d]pyrimid-6-yl]buta-2,3-dienamide;

N-[4-(2-Phenethylbenzindazol-5-ylamino)pyrido[3,4-d]pyrimid-6-yl]but-2-enamide;

N-[4-(2-Phenethylbenzindazol-5-ylamino)pyrido[3,4-d]pyrimid-6-yl]-4,4,4-trifluorobut-2-enamide;

N-[4-(2-Benzylbenzindazol-5-ylamino)pyrido[3,4-d]pyrimid-6-yl]-4,4,4-trifluorobut-2-enamide;

N-[4-(1-Phenethylbenzindazol-5-ylamino)pyrido[3,4-d]pyrimid-6-yl]-3-chloroacrylamide;

6-(S-Vinylsulfonamido)-4-(1-phenethylbenzindazol-5-ylamino)-pyrido[3,4-d]pyrimidine;

6-(S-Vinylsulfonamido)-4-(2-benzylbenzindazol-5-ylamino)-pyrido[3,4-d]pyrimidine;

N-[4-(2-Benzylbenzindazol-5-ylamino)pyrido[3,4-d]pyrimid-6-yl]-4-hydroxy-4-oxobut-2-enamide;

N-[4-(2-Benzylbenzindazol-5-ylamino)pyrido[3,4-d]pyrimid-6-yl]-4-(3-(N,N-dimethylamino)propylamino)-4-oxobut-2-enamide;

N-[4-(2-Benzyloxyindol-5-ylamino)pyrido[3,4-d]pyrimid-6-yl]-4-(3-(4-morpholino)propoxy)-4-oxobut-2-enamide;

N-[4-(2-Benzylbenzindazol-5-ylamino)pyrido[3,4-d]pyrimid-6-yl]-4-(3-(4-morpholino)propoxy)-4-oxobut-2-enamide;

N-[4-(2-Benzylbenzindazol-5-ylamino)pyrido[3,4-d]pyrimid-6-yl]4-(3-(4-morpholino)propylamino)-4-oxobut-2-enamide;

N-[4-(2-Benzyloxyindol-5-ylamino)pyrido[3,4-d]pyrimid-6-yl]-4-(3-(4-morpholino)propylamino)-4-oxobut-2-enamide;

4,4-Difluoro-8-(morpholin-4-yl)oct-2-enoic acid [4-(2-benzyloxybenzimidazol-5-ylamino)pyrido[3,4-d]pyrimid-6-yl]amide;

4,4-Difluoro-8-(morpholin-4-yl)oct-2-enoic acid [4-(2-benzylbenzindazol-5-ylamino)pyrido[3,4-d]pyrimid-6-yl]amide;

Pent-2-enedioic acid 1{[4-(2-benzylbenzindazol-5-ylamino)pyrido[3,4-d]-pyrimid-6-yl]amide}5-[(3-morpholin-4-ylpropyl)amide];

Pent-2-enedioic acid 1{[4-(2-benzylsulfonylbenzimidazol-5-ylamino)-pyrido[3,4-d]pyrimid-6-yl]amide}5-[(3-morpholin-4-ylpropyl)amide];

N-[4-(4-benzyloxybenzimidazol-5-ylamino)pyrido[3,4-d]pyrimid-6-yl]-4-(3-(morpholin-4-yl)propylthio)but-2-enamide;

N-[4-(2-Benzylbenzindazol-5-ylamino)pyrido[3,4-d]pyrimid-6-yl]-4-(3-(morpholin-4-yl)propylthio)but-2-enamide;

7-Morpholin-4-ylhept-2-ynoic acid [4-(2-benzylbenzindazol-5-ylamino)pyrido[3,4-d]pyrimid-6-yl]amide;

7-Morpholin-4-ylhept-2-ynoic acid [4-(2-benzylsulfonylbenzimidazol-5-ylamino)pyrido[3,4-d]pyrimid-6-yl]amide;

N-[4-(2-Benzylbenzindazol-5-ylamino)benzo[b]thieno[3,2-d]pyrimid-6-yl]acrylamide;

N-[4-(1-Benzylbenzindazol-5-ylamino)benzo[b]thieno[3,2-d]pyrimid-6-yl]acrylamide;

[4-(2-Benzylbenzindazol-5-ylamino)quinazolin-6-yl]acrylate;

N-(3-(4-Morpholino)propylamino)-4,O-[4-(2-benzylbenzindazol-5-ylamino)quinazolin-6-yl]-4-oxobut-2-enamide;

4,4-Difluoro-8-(morpholin-4-yl)oct-2-enoic acid [4-(2-benzylbenzindazol-5-ylamino)quinazolin-6-yl]ester;

Pent-2-enedioic acid 1{[4-(2-benzylbenzindazol-5-ylamino)quinazolin-6-yl]ester}5-[(3-morpholin-4-ylpropyl)amide];

[4-(2-Benzylbenzindazol-5-ylamino)quinazolin-6-yl]-4-(3-(morpholin-4-yl)propylthio)but-2-enoate; and 7-Morpholin-4-ylhept-2-ynoic acid [4-(2-benzylbenzindazol-5-ylamino)quinazolin-6-yl]ester.

DETAILED DESCRIPTION OF THE INVENTION

The present invention provides compounds having the Formula I

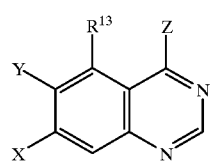

I wherein X is —D—E—F and Y is —$SR^4$, halogen, —$OR^4$, —$NHR^3$, or hydrogen, or X is —$SR^4$, halogen, —$OR^4$, —$NHR^3$, or hydrogen, and Y is —D—E—F;

D is 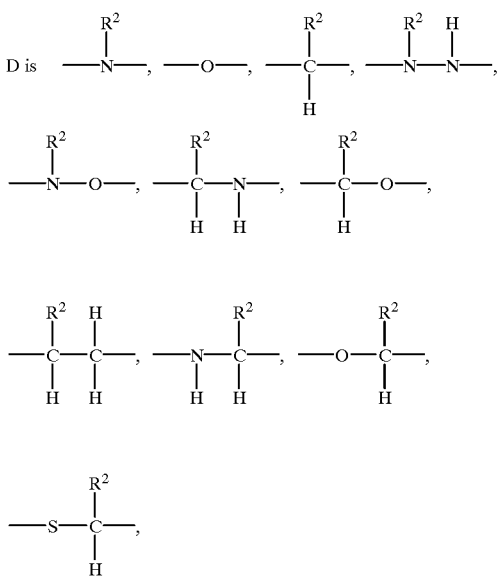

or absent;

E is 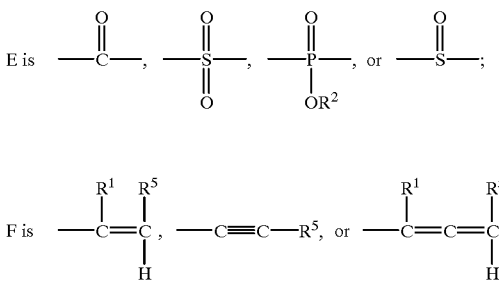

F is 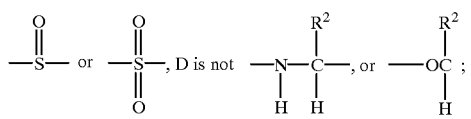

provided that when E is

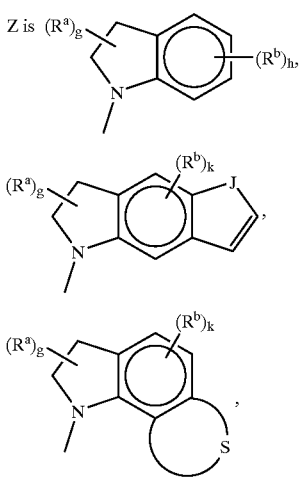

Z is 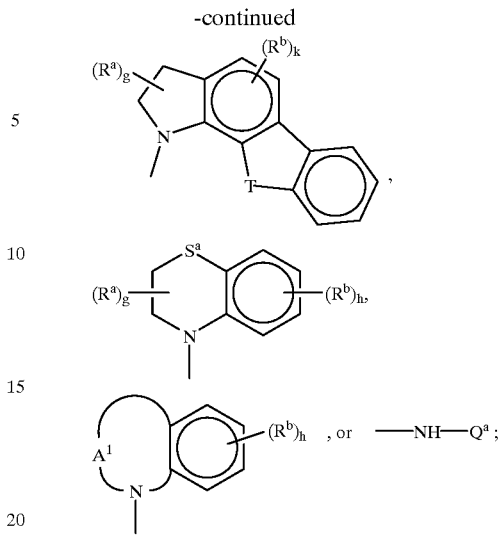

each $R^a$ is independently hydroxy, amino, N-mono- or N,N-di-$(C_1-C_4)$ alkylamino, sulfo, or $(C_1-C_4)$alkoxy (provided that such groups are not attached to a ring carbon which is adjacent to an oxy, thio, or —N—), or $R^a$ is independently carboxy, hydroxy$(C_1-C_4)$alkyl, $(C_1-C_4)$ alkoxy$(C_1-C_4)$ alkyl, amino$(C_1-C_4)$alkyl, mono-N- or di-N,N-$(C_1-C_4)$alkylamino$(C_1-C_4)$alkyl, morpholino $(C_1-C_4)$alkyl, 4-$(C_1-C_4)$alkyl-piperazin-1-yl$(C_1-C_4)$ alkyl, carboxy$(C_1-C_4)$alkyl, $(C_1-C_4)$alkoxycarbonyl, sulfo$(C_1-C_4)$alkyl, or $(C_1-C_4)$alkyl;

each $R^b$ is independently mono-, di-, or trifluoromethyl, halo, nitro, hydroxy, amino, axido, isothiocyano, $(C_1-C_4)$ alkyl, phenyl, thienyl, $(C_1-C_4)$alkoxy, benzyloxy, phenoxy, $(C_2-C_6)$alkenyl, $(C_2-C_6)$alkynyl, $(C_1-C_4)$ alkylenedioxy, cyano, benzoylamino, trifluoromethylcarbonylamino, $(C_1-C_4)$alkanoylamino, $(C_1-C_4)$alkanoyl, N-mono- or N,N-di-$(C_1-C_4)$ alkylamino, $(C_1-C_4)$alkylsulfonylamino, trifluoromethylsulfonylamino, $(C_1-C_4)$alkylthio, $(C_1-C_4)$ alkylsulfinyl or $(C_1-C_4)$alkylsulfonyl, pyrrol-1-yl, piperidin-1-yl or pyrrolidin-1-yl, said phenyl, benzyloxy, phenoxy, and benzoylamino optionally mono-substituted with halo, nitro, trifluoromethyl, hydroxy, or $(C_1-C_4)$ alkyl and said $(C_1-C_4)$alkylenedioxy is linked at both ends to adjacent carbons on the benzene moiety, or $R^b$ is —$Z^aR^{77}$;

J is —$CH_2$—, thio, —N(H)—, or oxy;

g is 0, 1, or 2;

h is 0 to 4;

k is 0, 1, or 2;

S completes a 5- or 6-membered aromatic or partially saturated ring that can contain an oxygen or sulfur atom;

T is —$CH_2$—, —N(H)—, thio, or oxy;

$S^a$ is —$CH_2$—, oxy, or thio;

$A^1$ completes a 7- to 9-membered mono-unsaturated monoaza ring;

$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, ($C_1$–$C_4$) alkyl, ($C_1$–$C_4$)alkoxy, ($C_1$–$C_4$)alkylamino, di-[($C_1$–$C_4$)alkyl]amino, and ($C_2$–$C_4$)alkanoylamino;

$R^1$ is hydrogen, halogen, or $C_1$–$C_6$ alkyl;

$R^2$, $R^3$, and $R^4$ are independently hydrogen, $C_1$–$C_6$ alkyl, —$(CH_2)_n$—N-piperidinyl, —$(CH_2)_n$—N-piperazinyl, —$(CH_2)_n$—$N_1$-piperazinyl[$N_4$-($C_1$–$C_6$)alkyl], —$(CH_2)_n$—N-pyrrolidyl, —$(CH_2)_n$-pyridinyl, —$(CH_2)_n$—N-imidazoyl, —$(CH_2)_n$-imidazoyl, —$(CH_2)_n$—N-morpholino, —$(CH_2)_n$—N-thiomorpholino, —$(CH_2)_n$—N-hexahydroazepine or substituted $C_1$–$C_6$ alkyl, wherein the substituents are selected from —OH, —$NH_2$, or

A and B are independently hydrogen, $C_1$–$C_6$ alkyl, —$(CH_2)_n$OH, —$(CH_2)_n$—N-piperidinyl, —$(CH_2)_n$—N-piperazinyl, —$(CH_2)_n$—$N_1$-piperazinyl[$N_4$-($C_1$–$C_6$)alkyl], —$(CH_2)_n$—N-pyrrolidyl, —$(CH_2)_n$—N-pyridyl, —$(CH_2)_n$-imidazoyl, or —$(CH_2)_n$—N-imidazoyl;

$Z^1$, $Z^2$, or $Z^3$ are independently hydrogen, halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;

$Z^a$ is a bond, —$CH_2$—, —S—, $SO_2$, —NH—, —O—, —$OCH_2$—, —S—$CH_2$—, —$SO_2$—, or —$CH_2CH_2$—;

$R^{77}$ is phenyl, substituted phenyl, or a 5- to 10-membered optionally substituted heterocyclic aromatic ring;

$R^5$ is hydrogen, halogen, $C_1$–$C_6$ perfluoroalkyl, 1,1-difluoro ($C_1$–$C_6$)alkyl, $C_1$–$C_6$ alkyl, —$(CH_2)_n$—N-piperidinyl, —$(CH_2)_n$-piperazinyl, —$(CH_2)_n$-piperazinyl[$N_4$-($C_1$–$C_6$) alkyl], —$(CH_2)_n$—N-pyrrolidyl, —$(CH_2)_n$-pyridinyl, —$(CH_2)_n$—N-imidazoyl, —$(CH_2)_n$—N-morpholino, —$(CH_2)_n$—N-thiomorpholino,

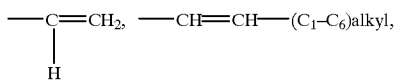

—$(CH_2)_n$—N-hexahydroazepine, —$(CH_2)_nNH_2$, —$(CH_2)_nNH(C_1$–$C_6$alkyl), —$(CH_2)_nN(C_1$–$C_6$alkyl)$_2$, -1-oxo($C_1$–$C_6$)alkyl, carboxy, ($C_1$–$C_6$)alkyloxycarbonyl, N-($C_1$–$C_6$)alkylcarbamoyl, phenyl or substituted phenyl, wherein the substituted phenyl can have from one to three substituents independently selected from $Z^1$, $Z^2$, $Z^3$ or a monocyclic heteroaryl group, and each $C_1$–$C_6$ alkyl group can be substituted with —OH, —$NH_2$ or —NAB, where A and B are as defined above, $R^6$ is hydrogen or $C_1$–$C_6$ alkyl; $R^{13}$ is hydrogen or halogen; and n is 1 to 4, p is 0 or 1, and the pharmaceutically acceptable salts, esters, amides, and prodrugs thereof.

In another preferred embodiment, present invention also provides compounds having the Formula II wherein Q is

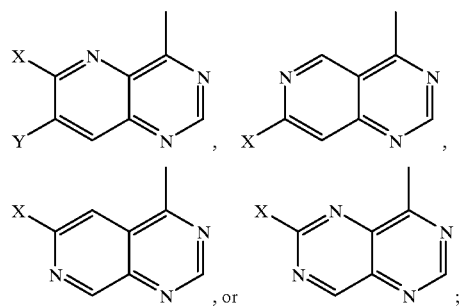

p is 0 or 1;

X is —D—E—F, and Y is —$SR^4$, —$OR^4$, —$NHR^3$ or hydrogen, or X is —$SR^4$, —$OR^4$, —$NHR^3$ or hydrogen, and Y is —D—E—F;

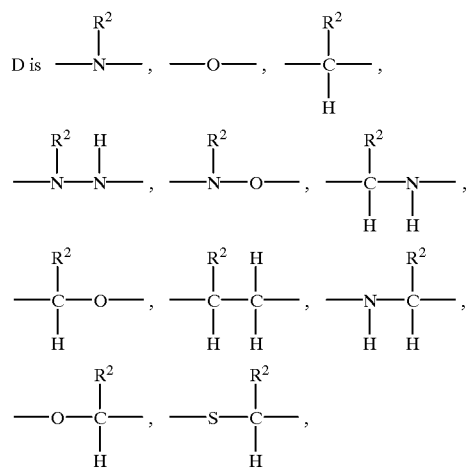

or absent;

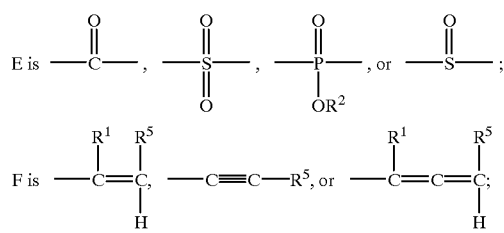

provided that when E is

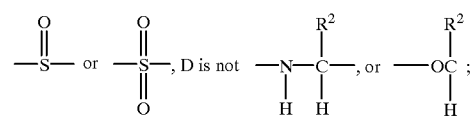

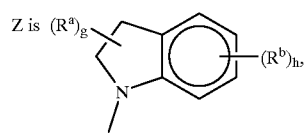

Q—Z　　　　　II

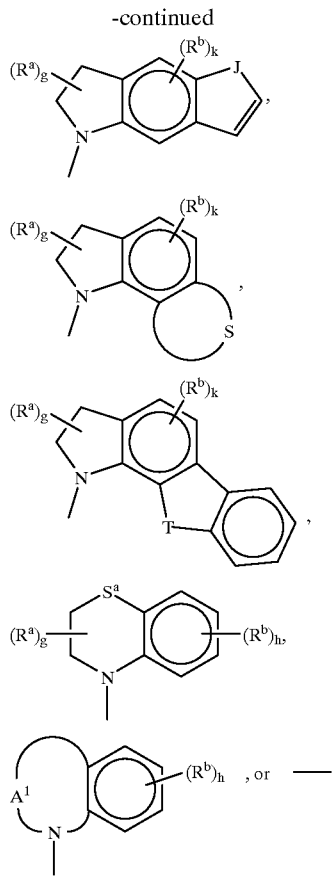

each $R^a$ is independently hydroxy, amino, N-mono- or N,N-di-($C_1$-$C_4$) alkylamino, sulfo, or ($C_1$-$C_4$)alkoxy (provided that such groups are not attached to a ring carbon which is adjacent to an oxy, thio, or —N—), or $R^a$ is independently carboxy, hydroxy($C_1$-$C_4$)alkyl, ($C_1$-$C_4$) alkoxy($C_1$-$C_4$) alkyl, amino($C_1$-$C_4$)alkyl, mono-N- or di-N,N-($C_1$-$C_4$)alkylamino($C_1$-$C_4$)alkyl, morpholino($C_1$-$C_4$)alkyl, 4-($C_1$-$C_4$)alkyl-piperazin-1-yl($C_1$-$C_4$) alkyl, carboxy($C_1$-$C_4$)alkyl, ($C_1$-$C_4$)alkoxycarbonyl, sulfo($C_1$-$C_4$)alkyl, or ($C_1$-$C_4$)alkyl;

each $R^b$ is independently mono-, di-, or trifluoromethyl, halo, nitro, hydroxy, amino, axido, isothiocyano, ($C_1$-$C_4$) alkyl, phenyl, thienyl, ($C_1$-$C_4$)alkoxy, benzyloxy, phenoxy, ($C_2$-$C_6$)alkenyl, ($C_2$-$C_6$)alkynyl, ($C_1$-$C_4$) alkylenedioxy, cyano, benzoylamino, trifluoromethylcarbonylamino, ($C_1$-$C_4$)alkanoylamino, ($C_1$-$C_4$)alkanoyl, N-mono- or N,N-di-($C_1$-$C_4$) alkylamino, ($C_1$-$C_4$)alkylsulfonylamino, trifluoromethylsulfonylamino, ($C_1$-$C_4$)alkylthio, ($C_1$-$C_4$) alkylsulfinyl or ($C_1$-$C_4$)alkylsulfonyl, pyrrol-1-yl, piperidin-1-yl or pyrrolidin-1-yl, said phenyl, benzyloxy, phenoxy, and benzoylamino optionally mono-substituted with halo, nitro, trifluoromethyl, hydroxy, or ($C_1$-$C_4$) alkyl and said ($C_1$-$C_4$)alkylenedioxy is linked at both ends to adjacent carbons on the benzene moiety, or $R^b$ is —$Z^aR^{77}$;

J is —$CH_2$—, thio, —N(H)—, or oxy;
g is 0, 1, or 2;
h is 0 to 4;
k is 0, 1, or 2;
S completes a 5- or 6-membered aromatic or partially saturated ring that can contain an oxygen or sulfur atom;
T is —$CH_2$, —N(H)—, thio, or oxy;

$S^a$ is —$CH_2$—, oxy, or thio;
$A^1$ completes a 7- to 9-membered mono-unsaturated mono-aza ring;
$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, ($C_1$-$C_4$) alkyl, ($C_1$-$C_4$)alkoxy, ($C_1$-$C_4$)alkylamino, di-[($C_1$-$C_4$) alkyl]amino, and ($C_2$-$C_4$)alkanoylamino;
$R^1$ is hydrogen, halogen, or $C_1$-$C_6$ alkyl;
$R^2$, $R^3$, and $R^4$ are independently hydrogen, $C_1$-$C_6$ alkyl, —($CH_2$)$_n$—N-piperidinyl, —($CH_2$)$_n$—N-piperazinyl, —($CH_2$)$_n$—$N_1$-piperazinyl[$N_4$-($C_1$-$C_6$)alkyl], —($CH_2$)$_n$ —N-pyrrolidyl, —($CH_2$)$_n$-pyridinyl, —($CH_2$)$_n$—N-imidazoyl, —($CH_2$)$_n$-imidazoyl, —($CH_2$)$_n$—N-morpholino, —($CH_2$)$_n$—N-thiomorpholino, —($CH_2$)$_n$— N-hexahydroazepine or substituted $C_1$-$C_6$ alkyl, wherein the substituents are selected from —OH, —$NH_2$, or $$-\underset{\underset{B,}{|}}{N}-$$

A and B are
independently hydrogen, $C_1$-$C_6$ alkyl, —($CH_2$)$_n$OH, —($CH_2$)$_n$—N-piperidinyl, —($CH_2$)$_n$—N-piperazinyl, —($CH_2$)$_n$—$N_1$-piperazinyl[$N_4$-($C_1$-$C_6$)alkyl], —($CH_2$)$_n$ —N-pyrrolidyl, —($CH_2$)$_n$—N-pyridyl, —($CH_2$)$_n$-imidazoyl, or —($CH_2$)$_n$—N-imidazoyl;

$E^1$, $E^2$, or $E^3$ are independently hydrogen, halogen, $C_1$-$C_6$ alkyl, $C_3$-$C_8$ cycloalkyl, $C_1$-$C_6$ alkoxy, $C_3$-$C_8$ cycloalkoxy, nitro, $C_1$-$C_6$ perfluoroalkyl, hydroxy, $C_1$-$C_6$ acyloxy, —$NH_2$, —NH($C_1$-$C_6$ alkyl), —N($C_1$-$C_6$ alkyl)$_2$, —NH($C_3$-$C_8$ cycloalkyl), —N($C_3$-$C_8$ cycloalkyl)$_2$, hydroxymethyl, $C_1$-$C_6$ acyl, cyano, azido, $C_1$-$C_6$ thioalkyl, $C_1$-$C_6$ sulfinylalkyl, $C_1$-$C_6$ sulfonylalkyl, $C_3$-$C_8$ thiocycloalkyl, $C_3$-$C_8$ sulfinylcycloalkyl, $C_3$-$C_8$ sulfonylcycloalkyl, mercapto, $C_1$-$C_6$ alkoxycarbonyl, $C_3$-$C_8$ cycloalkoxycarbonyl, $C_2$-$C_4$ alkenyl, $C_4$-$C_8$ cycloalkenyl, or $C_2$-$C_4$ alkynyl;

$Z^a$ is a bond, —$CH_2$—, —S—, $S_2$, —NH—, —O—, —$OCH_2$—, —S—$CH_2$—, —$SO_2$—, or —$CH_2CH_2$—;
$R^{77}$ is phenyl, substituted phenyl, or a 5- to 10-membered optionally substituted heterocyclic aromatic ring;
$R^5$ is hydrogen, halogen, $C_1$-$C_6$ perfluoroalkyl, 1,1-difluoro ($C_1$-$C_6$)alkyl, $C_1$-$C_6$ alkyl, —($CH_2$)$_n$—N-piperidinyl, —($CH_2$)$_n$-piperazinyl, —($CH_2$)$_n$-piperazinyl[$N_4$-($C_1$-$C_6$) alkyl], —($CH_2$)$_n$—N-pyrrolidyl, —($CH_2$)$_n$-pyridinyl, —($CH_2$)n—N-imidazoyl, —($CH_2$)$_n$—N-morpholino, —($CH_2$)$_n$—N-thiomorpholino, $$-\underset{\underset{H}{|}}{C}=CH_2, \quad -CH=CH-(C_1-C_6)alkyl,$$

—($CH_2$)$_n$—N-hexahydroazepine, —($CH_2$)$_n$$NH_2$, —($CH_2$)$_n$NH($C_1$-$C_6$alkyl), —($CH_2$)$_n$N($C_1$-$C_6$alkyl)$_2$, -1-oxo($C_1$-$C_6$)alkyl, carboxy, $C_1$-$C_6$)alkyloxycarbonyl, N-($C_1$-$C_6$)alkylcarbamoyl, phenyl or substituted phenyl, wherein the substituted phenyl can have from one to three substituents independently selected from $E^1$, $E^2$, $E^3$ or a monocyclic heteroaryl group, and each $C_1$-$C_6$ alkyl group can be substituted with —OH, —NH₂ or —NAB, where A and B are as defined above or C₁-C₆ alkyl; and n is 1 to 4, and the pharmaceutically acceptable salts, esters, amides, and prodrugs thereof.

In another embodiment, the present invention provides compounds having the Formula II $$Q-Z \qquad\qquad II$$

wherein Q is

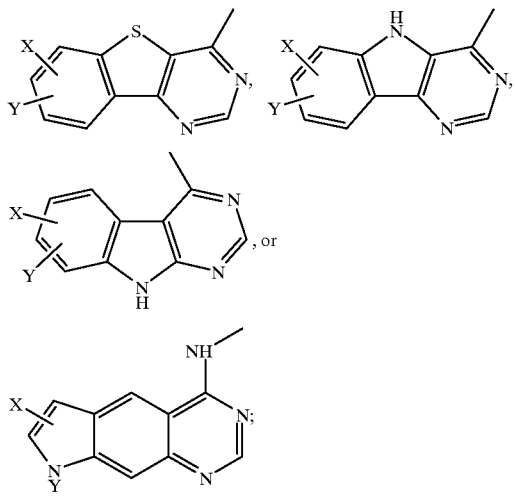

p is 0 or 1;

X is —D—E—F, and Y is —SR⁴, —OR⁴, —NHR³ or hydrogen, or X is —SR⁴, —OR⁴, —NHR³ or hydrogen, and Y is —D—E—F;

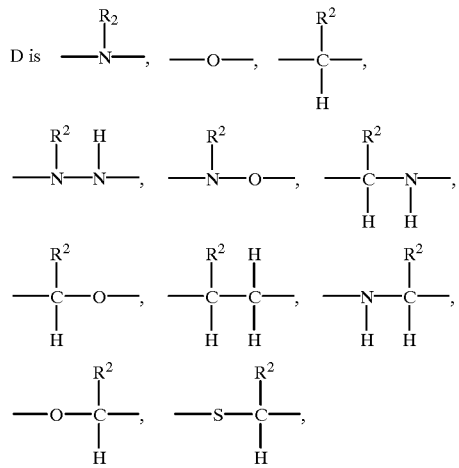

or absent;

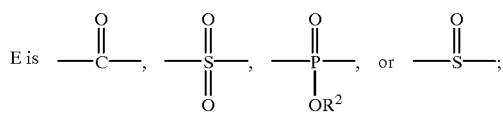

E is

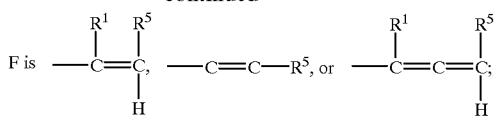

F is

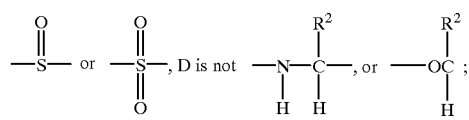

provided that when E is

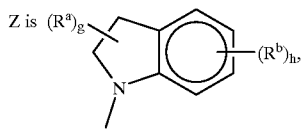, D is not

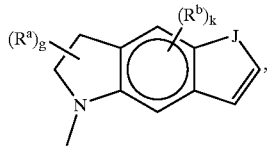

Z is

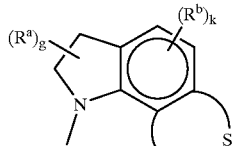

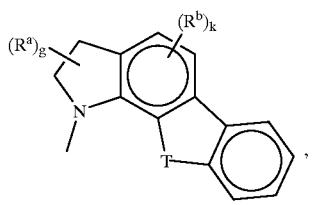

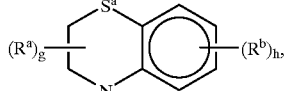

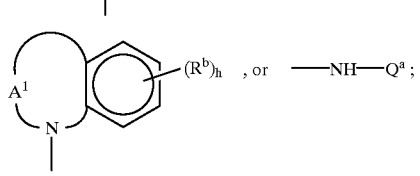

, or —NH—Qᵃ;

each $R^a$ is independently hydroxy, amino, N-mono- or N,N-di-(C₁–C₄) alkylamino, sulfo, or (C₁–C₄)alkoxy (provided that such groups are not attached to a ring carbon which is adjacent to an oxy, thio, or —N—), or $R^a$ is independently carboxy, hydroxy(C₁–C₄)alkyl, (C₁–C₄) alkoxy(C₁–C₄) alkyl, amino(C₁–C₄)alkyl, mono-N- or di-N,N-(C₁–C₄)alkylamino(C₁–C₄)alkyl, morpholino (C₁–C₄)alkyl, 4-(C₁–C₄)alkyl-piperazin-1-yl(C₁–C₄) alkyl, carboxy(C₁–C₄)alkyl, (C₁–C₄)alkoxycarbonyl, sulfo(C₁–C₄)alkyl, or (C₁–C₄)alkyl;

each $R^b$ is independently mono-, di-, or trifluoromethyl, halo, nitro, hydroxy, amino, axido, isothiocyano, (C₁–C₄) alkyl, phenyl, thienyl, (C₁–C₄)alkoxy, benzyloxy, phenoxy, $(C_2-C_6)$alkenyl, $(C_2-C_6)$alkynyl, $(C_1-C_4)$ alkylenedioxy, cyano, benzoylamino, trifluoromethylcarbonylamino, $(C_1-C_4)$alkanoylamino, $(C_1-C_4)$alkanoyl, N-mono- or N,N-di-$(C_1-C_4)$ alkylamino, $(C_1-C_4)$alkylsulfonylamino, trifluoromethylsulfonylamino, $(C_1-C_4)$alkylthio, $(C_1-C_4)$ alkylsulfinyl or $(C_1-C_4)$alkylsulfonyl, pyrrol-1-yl, piperidin-1-yl or pyrrolidin-1-yl, said phenyl, benzyloxy, phenoxy, and benzoylamino optionally mono-substituted with halo, nitro, trifluoromethyl, hydroxy, or $(C_1-C_4)$ alkyl and said $(C_1-C_4)$alkylenedioxy is linked at both ends to adjacent carbons on the benzene moiety, or $R^b$ is —$Z^aR^{77}$;

J is —$CH_2$—, thio, —N(H)—, or oxy;

g is 0, 1, or 2;

h is 0 to 4;

k is 0, 1, or 2;

S completes a 5- or 6-membered aromatic or partially saturated ring that can contain an oxygen or sulfur atom;

T is —$CH_2$, —N(H)—, thio, or oxy;

$S^a$ is —$CH_2$—, oxy, or thio;

$A^1$ completes a 7- to 9-membered mono-unsaturated mono-aza ring;

$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, $(C_1-C_4)$ alkyl, $(C_1-C_4)$alkoxy, $(C_1-C_4)$alkylamino, di-[$(C_1-C_4)$ alkyl]amino, and $(C_2-C_4)$alkanoylamino;

$R^1$ is hydrogen, halogen, or $C_1-C_6$ alkyl;

$R^2$, $R^3$, and $R^4$ are independently hydrogen, $C_1-C_6$ alkyl, —$(CH_2)_n$—N-piperidinyl, —$(CH_2)_n$—N-piperazinyl, —$(CH_2)_n$—$N_1$-piperazinyl[$N_4$-$(C_1-C_6)$alkyl], —$(CH_2)_n$—N-pyrrolidyl, —$(CH_2)_n$-pyridinyl, —$(CH_2)_n$—N-imidazoyl, —$(CH_2)_n$-imidazoyl, —$(CH_2)_n$—N-morpholino, —$(CH_2)_n$—N-thiomorpholino, —$(CH_2)_n$—N-hexahydroazepine or substituted $C_1-C_6$ alkyl, wherein the substituents are selected from —OH, —$NH_2$, or

A and B are
independently hydrogen, $C_1-C_6$ alkyl, —$(CH_2)_nOH$, —$(CH_2)_n$—N-piperidinyl, —$(CH_2)_n$—N-piperazinyl, —$(CH_2)_n$—$N_1$-piperazinyl[$N_4$-$(C_1-C_6)$alkyl], —$(CH_2)_n$—N-pyrrolidyl, —$(CH_2)_n$—N-pyridyl, —$(CH_2)_n$-imidazoyl, or —$(CH_2)_n$—N-imidazoyl;

$E^1$, $E^2$, or $E^3$ are independently hydrogen, halogen, $C_1-C_6$ alkyl, $C_3-C_8$ cycloalkyl, $C_1-C_6$ alkoxy, $C_3-C_8$ cycloalkoxy, nitro, $C_1-C_6$ perfluoroalkyl, hydroxy, $C_1-C_6$ acyloxy, —$NH_2$, —$NH(C_1-C_6$ alkyl), —$N(C_1-C_6$ alkyl)$_2$, —$NH(C_3-C_8$ cycloalkyl), —$N(C_3-C_8$ cycloalkyl)$_2$, hydroxymethyl, $C_1-C_6$ acyl, cyano, azido, $C_1-C_6$ thioalkyl, $C_1-C_6$ sulfinylalkyl, $C_1-C_6$ sulfonylalkyl, $C_3-C_8$ thiocycloalkyl, $C_3-C_8$ sulfinylcycloalkyl, $C_3-C_8$ sulfonylcycloalkyl, mercapto, $C_1-C_6$ alkoxycarbonyl, $C_3-C_8$ cycloalkoxycarbonyl, $C_2-C_4$ alkenyl, $C_4-C_8$ cycloalkenyl, or $C_2-C_4$ alkynyl;

$Z^a$ is a bond, —$CH_2$—, —S—, $SO_2$, —NH—, —O—, —$OCH_2$—, —S—$CH_2$—, —$SO_2$—, or —$CH_2CH_2$—;

$R^{77}$ is phenyl, substituted phenyl, or a 5- to 10-membered optionally substituted heterocyclic aromatic ring;

$R^5$ is hydrogen, halogen, $C_1-C_6$ perfluoroalkyl, 1,1-difluoro $(C_1-C_6)$alkyl, $C_1-C_6$ alkyl, —$(CH_2)_n$—N-piperidinyl, —$(CH_2)_n$-piperazinyl, —$(CH_2)_n$-piperazinyl[$N_4$-$(C_1-C_6)$ alkyl], —$(CH_2)_n$—N-pyrrolidyl, —$(CH_2)_n$-pyridinyl, —$(CH_2)_n$—N-imidazoyl, —$(CH_2)_n$—N-morpholino, —$(CH_2)_n$—N-thiomorpholino,

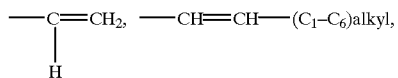

—$(CH_2)_n$—N-hexahydroazepine, —$(CH_2)_nNH_2$, —$(CH_2)_nNH(C_1-C_6alkyl)$ —$(CH_2)_nN(C_1-C_6alkyl)_2$, -1-oxo$(C_1-C_6)$alkyl, carboxy, $(C_1-C_6)$alkyloxycarbonyl, N-$(C_1-C_6)$alkylcarbamoyl, phenyl or substituted phenyl, wherein the substituted phenyl can have from one to three substituents independently selected from $E^1$, $E^2$, $E^3$ or a monocyclic heteroaryl group, and each $C_1-C_6$ alkyl group above in $R^5$ can be substituted with —OH, —$NH_2$ or —NAB, where A and B are as defined above or $C_1-C_6$ alkyl; and n is 1 to 4, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "cycloalkyl" means a cyclic hydrocarbon. Examples of cycloalkyl groups include cyclopropyl, cyclobutyl, cyclopentyl, and cyclohexyl.

The term "cycloalkoxy" means a cycloalkyl group attached to an oxygen atom.

The term "perfluoroalkyl" means an alkyl group in which all the hydrogen atoms have been replaced by fluorine atoms.

The term "acyl" means a group derived from an organic acid by removal of the hydroxy group (—OH).

The term "acyloxy" means an acyl group attached to an oxygen atom.

The term "thioalkyl" means an alkyl group attached to a sulfur atom.

The term "sulfinylalkyl" means a sulfinyl group attached to an alkyl group.

The term "sulfonylalkyl" means a sulfonyl group attached to an alkyl group.

The term "thiocycloalkyl" means a cycloalkyl group attached to a sulfur atom.

The term "sulfinylcycloalkyl" means a sulfinyl group attached to a cycloalkyl group.

The term "sulfonylcycloalkyl" means a sulfonyl group attached to a cycloalkyl group.

The term "mercapto" means a —SH group.

The term "alkoxycarbonyl" means an alkoxy group attached to a carbonyl group.

The term "cycloalkoxycarbonyl" means a cycloalkyoxy group attached to a carbonyl group.

The term "cycloalkenyl" means a cyclic hydrocarbon containing one or more carbon-carbon double bond.

The term "alkynyl" means a hydrocarbon having one or more carbon-carbon triple bond.

The term "monocyclic heteroaryl" mean a heterocyclic aryl compound having only one ring structure. The cyclic compound is aromatic and contains one or more heteroatom. Examples of heteroatoms include, but are not limited to, nitrogen, oxygen, sulfur, and phosphorus. Examples of monocyclic heteroaryl groups include, but are not limited to, pyridyl, thienyl, and imidazoyl.

The symbol "—" represents a covalent bond.

The compounds of Formulas I or II are irreversible inhibitors of tyrosine kinases, particularly EGF tyrosine kinase. A therapeutically effective amount of the compounds of Formula I or II can be administered to a patient having cancer or a patient having restenosis or at risk of having restenosis or a patient having psoriasis, atherosclerosis, or endometriosis. Those skilled in the art are readily able to identify patients having cancer, restenosis, psoriasis, atherosclerosis, or endometriosis, and patients who are at risk of developing restenosis. The term "patient" means animals such as dogs, cats, cows, sheep, and also includes humans.

The compounds of the present invention can be administered to humans and animals either orally, rectally, parenterally (intravenously, intramuscularly or subcutaneously), intracisternally, intravaginally, intraperitoneally, intravesically, locally (powders, ointments, or drops), or as a buccal or nasal spray. The compounds can be administered alone or as part of a pharmaceutically acceptable composition that includes pharmaceutically acceptable excipients. It is noted that more than one compound of Formula I or II can be administered either concurrently or sequentially.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethylene-glycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine and the like (see, for example, S. M. Berge, et al., "Pharmaceutical Salts," *J Pharm Sci,* 1977;66:1–19 which is incorporated herein by reference).

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

It is intended that the compounds of Formula I, II, or III be either synthetically produced or biologically produced.

The following examples illustrate particular embodiments of the invention and are not intended to limit the specification, including the claims, in any manner.

GENERAL SYNTHETIC SCHEMES

Amine-Linked Alkylating Michael Acceptor Sidechains

The amine is acylated either by an acid in the presence of a coupling agent such as EDAC, or by an acid chloride. The amine in turn can be made by reduction of the corresponding nitro compound, displacement of a halogen by an amine or ammonia equivalent, or in the case of pyrido[4,3-d] pyrimidines by direct incorporation during the synthesis. 2-Haloalkylsulfonyl halides form vinyl sulfonamides when treated with the aryl amine and excess tertiary amine base.

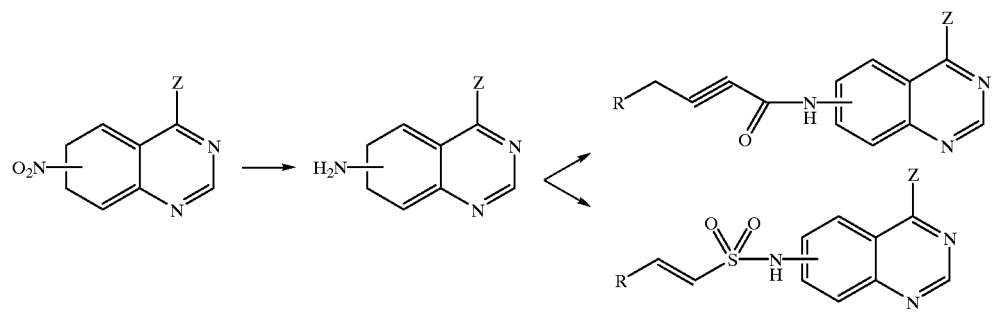

-continued

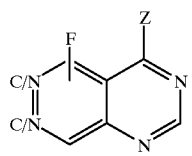 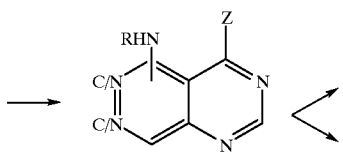 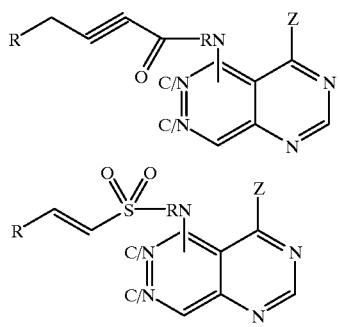

C/N means either a carbon or nitrogen atom is present at that location. —means a bond or no bond.

Oxygen-Linked Alkylating Michael Acceptor Sidechains

The hydroxyl group is acylated either by an acid in the presence of a coupling agent such as EDAC, or by an acid chloride. The hydroxyl compound can in turn can be made by cleavage of the corresponding methyl ether. 3-Methylthioalkanoic acid or their acid chlorides can be used to acylate the oxygen followed by S-alkylation or oxidation and basic or thermal elimination.

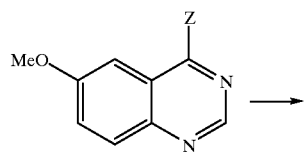

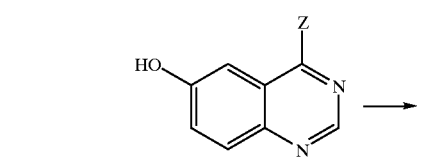

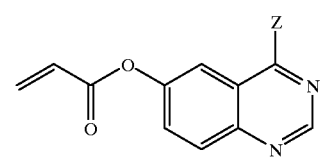

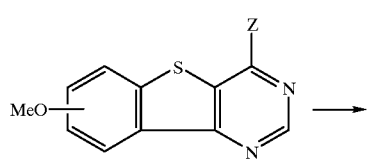

-continued

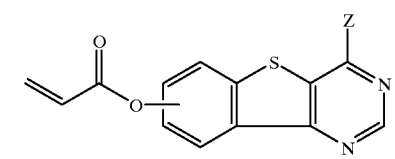

Ar and R denote an aryl group and R denotes an organic group as exemplified herein.

Carbon-Linked Alkylating Michael Acceptor Sidechains

A Stille or Suzuki coupling can be used to couple the sidechain to an appropriately substituted quinazoline/pyridopyrimidine/pyrimidinopyrimidine/tricycle. These in turn can be made as aryl halides by methods known in the art, or as aryl triflates by triflation of the hydroxyl compounds described above, as aryl stannanes by reaction of the abovementioned triflates with hex a methyl distannane, or as arylboronic acids by conversion of aryl iodides to arylorgano-metallics, followed by treatment with borate esters and hydrolysis. Alternatively, aryl iodides can be converted to the arylzinc species and coupled with activated halides.

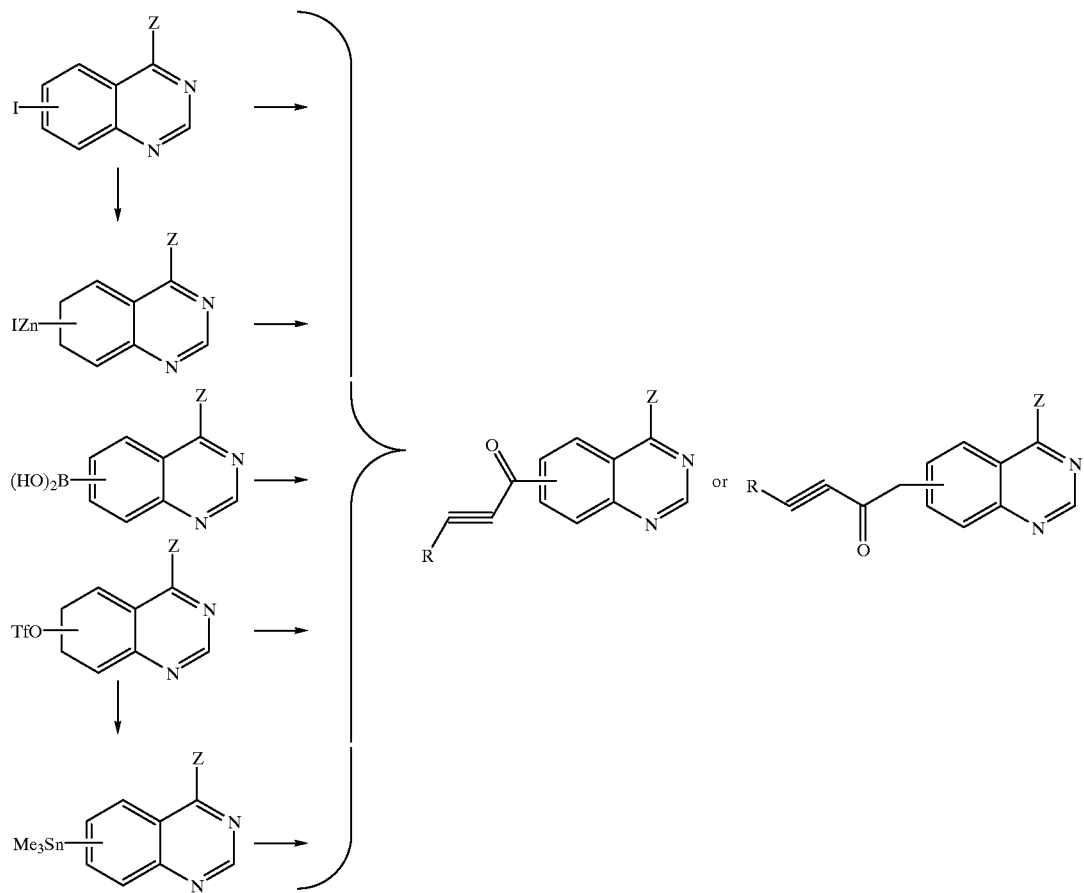

Sulfur-Linked Alkylating Michael Acceptor Sidechains

Activated halides in pyridopyrimidines and pyrimidinopyrimidines can be displaced by suitable 2-hydroxythiolates, and these in turn can be oxidized to sulfones, and then water eliminated by treatment with mesyl chloride and several equivalents of a base. For quinazo lines, and claimed tricycles, either an activated halogen especially fluorine can be used in the sequence just described for pyridopyrimidines, or an aryl iodide precursor can be metalated, quenched with sulfur or a suitable sulfur electrophilic progenitor and then the resultant aryl thiol used to open a terminal epoxide, giving a 2-hydroxy thioether which can be converted onto a vinyl sulfone by oxidation and water elimination as described above.

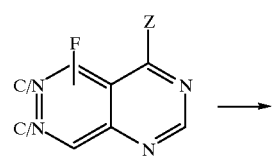

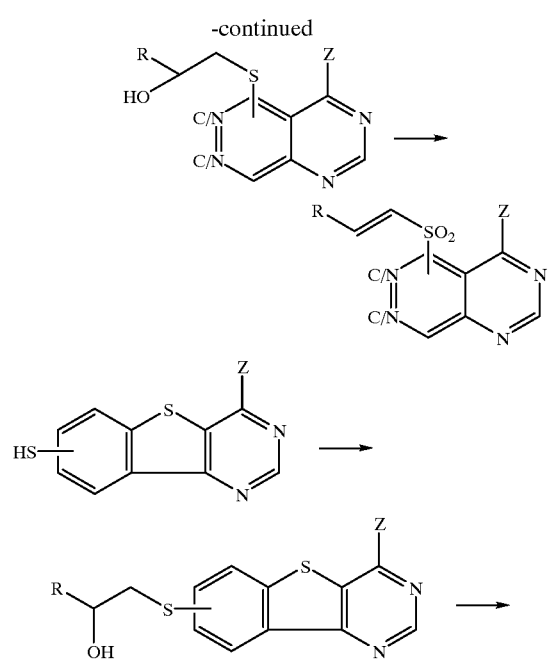

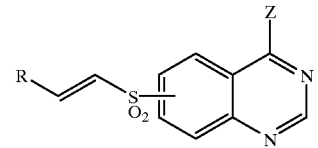

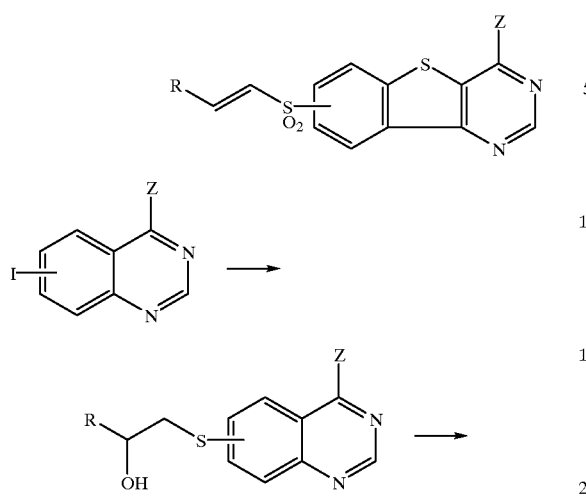

Hydrazino-Linked Alkylating Michael Acceptor Sidechains

Activated halides in pyridopyrimidines and pyrimidinopyrimidines and appropriately substituted quinazolines can be displaced by a (N-alkyl) hydrazine. Alternatively, an amino-derivative of the desired ring nucleus can be diazotized, and then reduced to the hydrazine. The distal nitrogen of the hydrazine can then be acylated, sulfonylated or phosphorylated, by methods well-known to one skilled in the art.

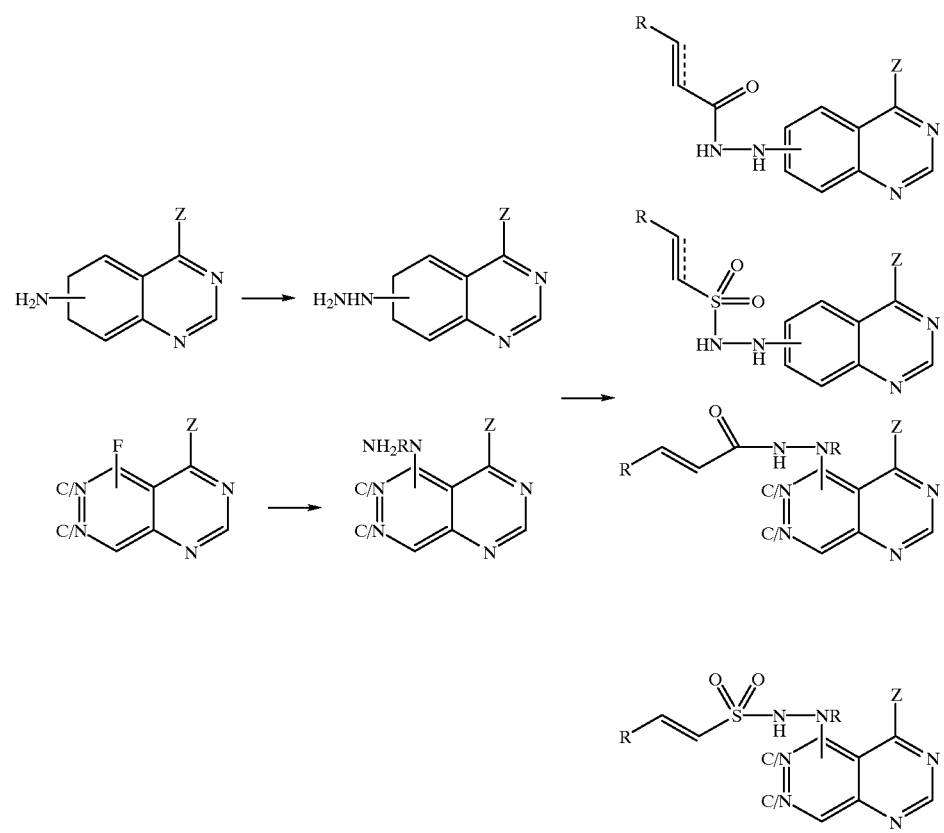

Hydroxylamino-O-Linked Alkylating Michael Acceptor Sidechains

Activated halides in pyridopyrimidines and pyrimidinopyrimidines and appropriately substituted quinazolines can be displaced by a suitably O-protected (N-alkyl) hydroxylamine. Alternatively, a nitro-derivative of the desired ring nucleus can be synthesized, and then reduced to the hydroxylamine under appropriate mildly reducing conditions. The oxygen of the hydroxylamine can then be acylated, sulfonylated or phosphorylated, by methods well-known to one skilled in the art.

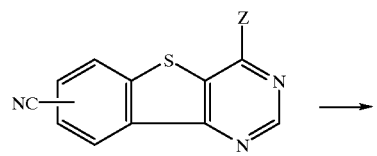

-continued

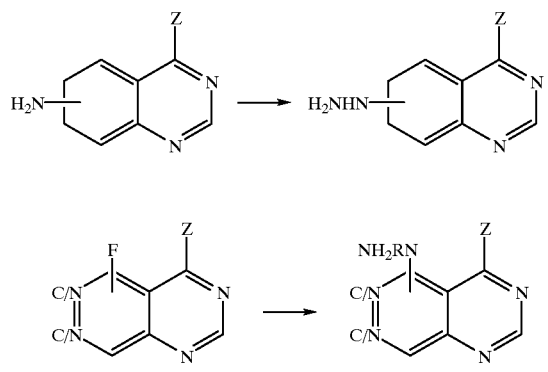

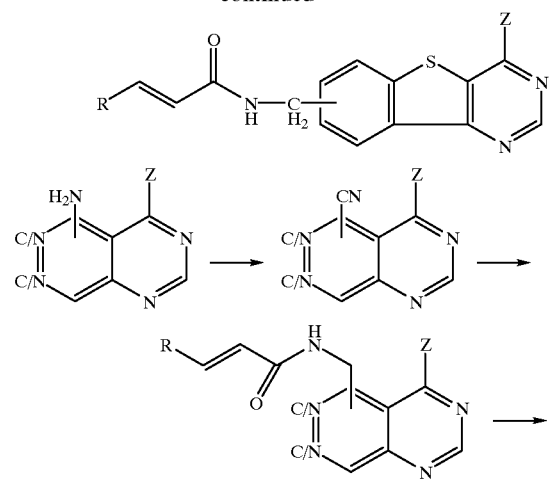

Methyleneamino-N-Linked Alkylating Michael Acceptor Sidechains

Activated halides in pyridopyrimidines and pyrimidinopyrimidines and appropriately substituted quinazolines can be displaced by cyanide, preferably in the presence of copper or nickel salt catalysis. Alternatively, an amino-derivative of the desired ring nucleus can be diazotized, and then converted to the nitrile as described above. In some cases, the nitrile functionality can be incorporated into the heterocycle earlier in the synthesis, either as itself, or via a carboxylic acid or aldehyde, both of which can readily be turned into nitrile compounds by one skilled in the art. Reduction of the nitrile to a methyleneamine is followed by nitrogen acylation, sulfonylation or phosphorylation, by methods well-known to one skilled in the art.

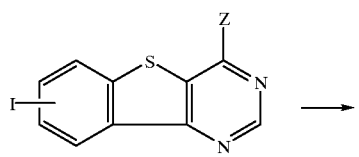

-continued

Methyleneoxy-O-Linked Alkylating Michael Acceptor Sidechains

Hydroxymethyl compounds can be incorporated into appropriate heterocycles in many ways obvious to one skilled in the art. For example, iodoquinazolines may be carbonylated in a Heck reaction, and then reduced with NaBH₄ to the desired precursor. Aminopyridopyrimidines may be diazotized, converted to the nitrile, partially reduced to an imine, hydrolysed, and the resultant aldehyde reduced to hydroxymethyl. The oxygen of the hydroxymethyl can then be acylated, sulfonylated or phosphorylated, by methods well-known to one skilled in the art.

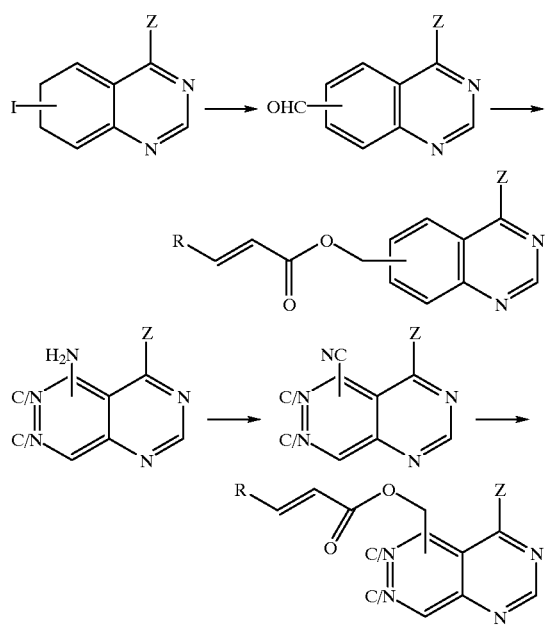

Ethano-Linked Alkylating Michael Acceptor Sidechains

Michael addition of a cuprate, derived via an organozincate from an iodoquinazoline, to a divinylketone, or appropriately mono-masked derivative, followed by unmasking of the second unsaturated functionality, if required, will give compounds of the desired type. Aldehydes derived from pyridopyrimidines or pyrimidopyrimidnes as described above can be homologated to the desired compounds by a wide variety of techniques such as the one illustrated, by one skilled in the art.

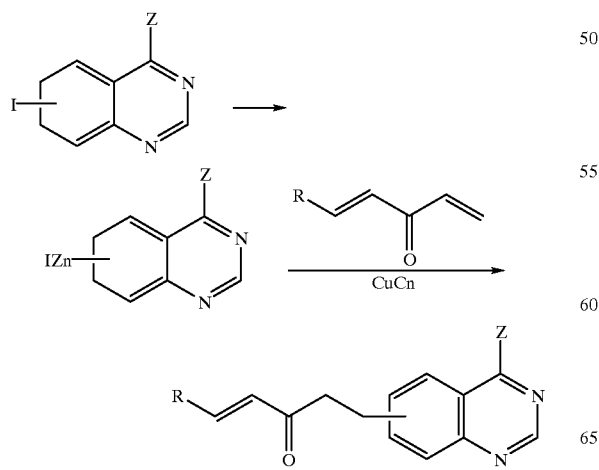

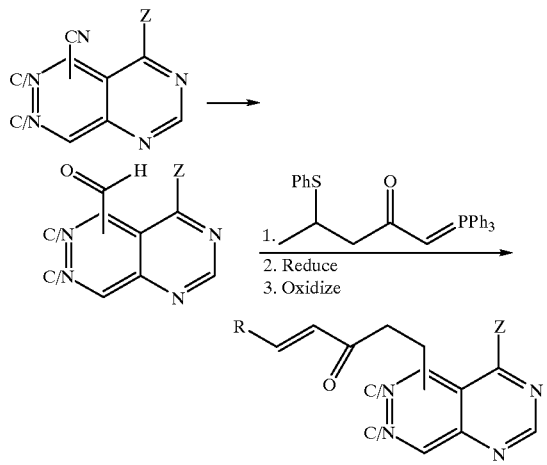

Aminomethyl-C-Linked Alkylating Michael Acceptor Sidechains

Amino-heterocycles of the type described throughout this application can be alkylated by various double bond-masked equivalents of 1-bromobut-3-en-2-one, followed by unmasking of the unsaturation by methods known to one skilled in the art.

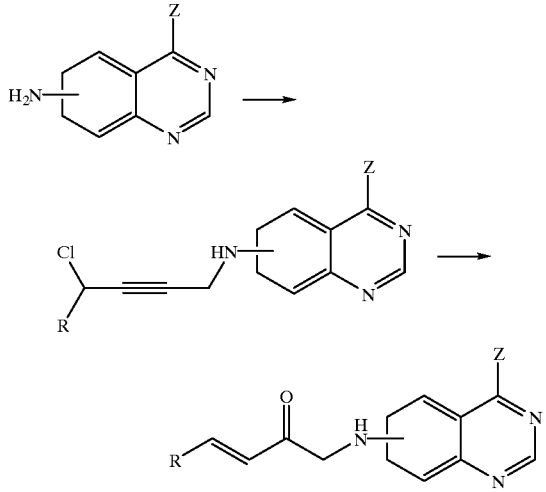

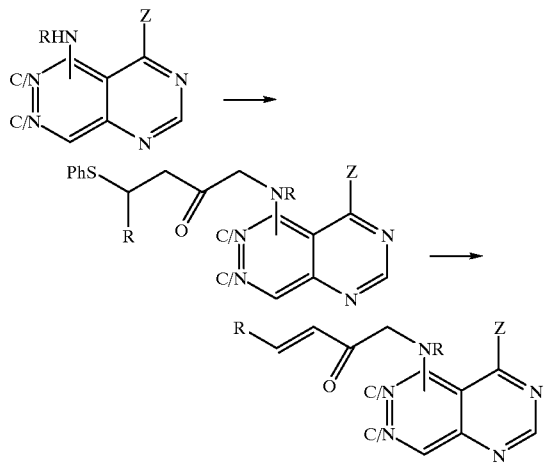

Hydroxymethyl-C-Linked Alkylating Michael Acceptor Sidechains

Hydroxy-heterocycles made as described previously from methoxy-heterocycles can be alkylated by various double bond-masked equivalents of 1-bromobut-3-en-2-one, followed by unmasking of the unsaturation by methods known to one skilled in the art. Alternatively, alkylation of the phenol can be accomplished with chloroacetic acid, followed by conversion to an acyl chloride and Stille coupling of that acyl halide with an appropriate alkenyl stannane.

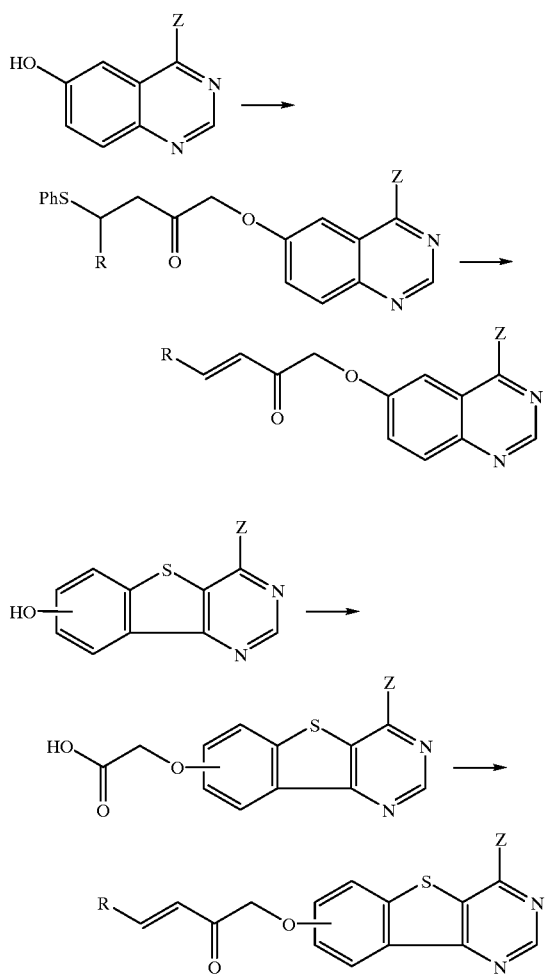

Thiomethyl-C-Linked Alkylating Michael Acceptor Sidechains

Appropriate mercapto-heterocycles, made by displacement of activated halides on the heteroaromatic ring, can be alkylated by various double bond-masked equivalents of 1-bromobut-3-en-2-one, followed by unmasking of the unsaturation by methods known to one skilled in the art. Alternatively, alkylation of the thiol can be accomplished with chloroacetic acid, followed by conversion to an acyl chloride and Stille coupling of that acyl halide with an appropriate alkenyl stannane.

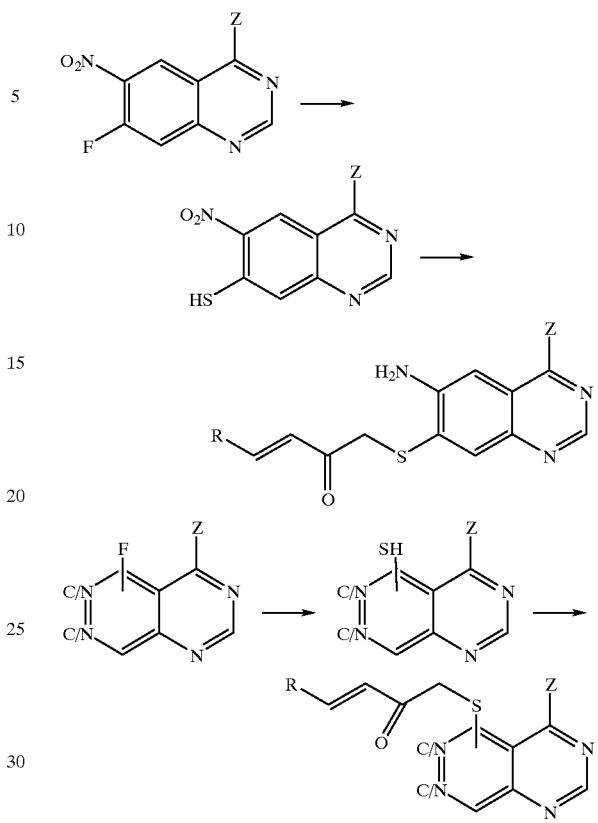

EXAMPLE 1

N-[4-(6-Bromo-2,3-dihydroindol-1-yl)quinazolin-6-yl] acrylamide

Step (a) 6-Nitro-4-(1-(6-bromo-indolinyl))-quinazoline

A suspension of 6-bromo-indoline (490 mg, 2.47 mmol) (Miyake Y., Kikugawa Y., *J. Het. Chem.*, 1983;20:349), 4-chloro-6-nitro-quinazoline (660 mg, 2.47 mmol), and N,N-dimethylaniline (0.63 mL, 4.9 mmol) in 15 mL of isopropyl alcohol was heated under reflux for 1 hour. The suspension was concentrated to give a solid, which was shaken with a mixture of ethyl acetate and saturated aqueous sodium bicarbonate. The solid was collected by filtration and recrystallized from a boiling mixture of ethanol (100 mL) and dimethylformamide (25 mL) to give the product as a yellow solid (290 mg, 32%), mp 249–251° C.

Anal. Calcd. for $C_{16}H_{11}Br_1N_4O_2$: C, 51.77; H, 2.99; N, 15.09. Found: C, 51.58; H, 2.91; N, 15.01.

MS (APCI): Calcd. for M+1,371.0; Found, 371.0

Step (b) 6-Amino-4-(1-(6-bromo-indolinyl))-quinazoline

To a suspension of 6-nitro-4-(1-(6-bromo-indolinyl))-quinazoline (240 mg, 6.5 mmol) and acetic acid (1.04 mL, 18 mmol) in $H_2O$ (75 mL) and ethanol (100 mL), heated under reflux, was added iron powder (washed with 1N HCl, then $H_2O$, and dried; 180 mg, 3.23 mmol). After 30 minutes of heating, more iron powder (320 mg, 5.73 mmol) was added, and heating was continued for another 30 minutes. The reaction was filtered while hot and the solids washed with ethanol. To the filtrate and washings was added concentrated $NH_4OH$ (10 mL), and a small amount of solid was removed by filtration. The fitrate was concentrated, and the resulting residue was purified by flash silica gel chromatography dichloromethane/methanol, 10:1) to give a yellow foam.

MS (APCI): Calcd. for $C_{16}H_{13}Br_1N_4$: M+1,341.0; Found, 341.1

The NMR spectrum showed the presence of an acetate species. This was removed by dissolving the solid in diethylether, and washing the solution consecutively with $H_2O$, saturated aqueous $NaHCO_3$, and brine. The solution was dried ($MgSO_4$) and concentrated to give the product as a brown solid (220 mg, 100%).

Step (c)

To a suspension of 6-amino-4-(1-(6-bromo-indolinyl))-quinazoline (200 mg, 0.6 mmol) and N-ethyl-N'-(3-N,N-dimethylaminopropylcarbodiimide hydrochloride) (450 mg, 2.3 mmol) in dimethylformamide (1 mL) and tetrahydrofuran (3 mL), cooled in an ice-bath and under nitrogen, was added acrylic acid (0.16 mL, 2.3 mmol), followed by diisopropylethylamine (0.40 mL, 2.3 mmol). The ice-bath was removed, and the suspension was stirred at room temperature for 18 hours. The resulting solution was poured into cold $H_2O$, and the suspension was extracted with dicholoromethane (4×25 mL). The extracts were dried ($MgSO_4$), concentrated, and purified by flash silica gel chromatography (dichloromethane/methanol, 9:1) to give the product as a light yellow solid (110 mg, 41%), mp 214–216° C. This material contained 0.3 mol of dimethylformamide (substantiated by NMR) and 0.3 mol $H_2O$ by C,H,N analysis.

Anal. Calcd. for $C_{19}H_{15}Br_1N_4O_1\cdot0.3DMF\cdot0.3H_2O$: C, 56.56; H, 4.22; N, 14.25. Found: C, 56.37; H, 4.14; N, 14.01.

MS (APCI): Calcd. for M+1, 395.0; Found, 395.1

BIOLOGICAL METHODS

Tissue Culture

A431 human epidermoid carcinoma cells were obtained from the American Type Culture Collection, Rockville, Md. and maintained as monolayers in dMEM (Dulbecco's modified eagle medium)/F12, 50:50 (Gibco/BRL) containing 10% fetal bovine serum. For growth inhibition assays, dilutions of the designated compound in 10 $\mu$L were placed in 24-well Linbro plates (1.7×1.6 cm, flat bottom) followed by the addition of cells ($2\times10^4$) in 2 mL of media. The plates were incubated for 72 hours at 37° C. in a humidified atmosphere containing 5% $CO_2$ in air. Cell growth was determined by cell count with a Coulter Model AM electronic cell counter (Coulter Electronics, Inc., Hialeah, Fla.).

Purification of Epidermal Growth Factor Receptor Tyrosine Kinase

Human EGF receptor tyrosine kinase was isolated from A431 human epidermoid carcinoma cells by the following method. Cells were grown in roller bottles in dMEM/F12 media (Gibco/BRL) containing 10% fetal calf serum. Approximately $10^9$ cells were lysed in 2 volumes of buffer containing 20 mM N-[2-hydroxyethyl]piperazine-N'-[2-ethane sulfonic acid](Hepes), pH 7.4, 5 mM ethylene glycol-bis($\beta$-aminoethyl ether) N,N,N',N'-tetraacetic acid (EGTA), 1% Triton X-100, 10% glycerol, 0.1 mM sodium orthovanadate, 5 mM sodium fluoride, 4 mM pyrophosphate, 4 mM benzamide, 1 mM dithiothreitol (DTT), 80 $\mu$g/mL aprotinin, 40 $\mu$g/mL leupeptin, and 1 mM phenylmethyl sulfonyl fluoride (PMSF). After centrifugation at 25,000×g for 10 minutes, the supernatant was applied to a fast Q sepharose column (Pharrnacia Biotech., Inc., Piscataway, N.J.) and eluted with a linear gradient from 0.1 M NaCl to 0.4 M NaCl in 50 mM Hepes, 10% glycerol, pH 7.4. Enzyme active fractions were pooled, divided into aliquots, and stored at –100° C. Fibroblast growth factor receptor (FGFR), platelet-derived growth factor (PDGF), insulin, and c-src tyrosine kinases were obtained by methods well-known in the art. For example, see Fry et al., "Strategies For The Discovery Of Novel Tyrosine Kinase Inhibitors With Anticancer Activity, *Anticancer Drug Design*, 1994;9:331–351.

Tyrosine Kinase Assays

Enzyme assays for $IC_{50}$ determinations were performed in 96-well filter plates (Millipore MADVN6550, Millipore, Bedford, Mass.). The total volume was 0.1 mL containing 20 mM Hepes, pH 7.4, 50 $\mu$M sodium vanadate, 40 mM magnesium chloride, 10 $\mu$M adenosine triphosphate (ATP) containing 0.5 $\mu$Ci of [$^{32}$P]ATP, 20 $\mu$g of poly Glutamic acid/tyrosine (Sigma Chemical Co., St. Louis, Mo.), 10 ng of EGF receptor tyrosine kinase and appropriate dilutions of inhibitor. All components except the ATP are added to the well and the plate incubated with shaking for 10 minutes at 25° C. The reaction is started by adding [$^{32}$P]ATP, and the plate is incubated at 25° C. for 10 minutes. The reaction is terminated by addition of 0.1 mL of 20% trichloroacetic acid (TCA). The plate is kept at 4° C. for at least 15 minutes to allow the substrate to precipitate. The wells are then washed 5 times with 0.2 mL of 10% TCA and $^{32}$P incorporation determined with a Wallac beta plate counter (Wallac, Inc., Gaithersburg, Pa.). Assays using intracellular kinase domains of PDGF, FGF, and insulin receptors, as well as those for c-src, were performed as described for the EGF receptor except that 10 mM Manganese chloride was included in the reaction.

Western Blotting Procedure

Extracts were made by lysing the monolayers in 0.2 mL of boiling Laemlli buffer (2% sodium dodecyl sulfate, 5% beta-mercaptoethanol, 10% glycerol and 50 mM tris [hydroxymethyl]aminomethane (Tris), pH 6.8), and the lysates were heated to 100° C. for 5 minutes. Proteins in the lysate were separated by polyacrylamide gel electrophoresis and electrophoretically transferred to nitrocellulose. The membrane was washed once in 10 mM Tris, pH 7.2, 150 mM NaCl, 0.01% Azide (TNA), and blocked overnight in TNA containing 5% bovine serum albumin and 1% ovalbumin. The membrane was blotted for 2 hours with antiphosphotyrosine antibody (UBI, 1 $\mu$g/mL in blocking buffer) and then washed twice in TNA, once in TNA containing 0.05% Tween-20 detergent and 0.05% nonidet P-40 detergent and twice in TNA. The membranes were then incubated for 2 hours in blocking buffer containing 0.1 $\mu$Ci/mL of [$^{125}$I] protein A and then washed again as above. After the blots were dry, they were loaded into a film cassette and exposed to X-AR X-ray film (Eastman Kodak Co., Rochester, N.Y.) for 1 to 7 days. Band intensities were determined with a Molecular Dynamics laser densitometer.

Autophosphorylation Assay

A431 human epidermoid carcinoma cells were grown in 6-well plates to about 80% confluency and then incubated in serum-free media for 18 hours. Duplicate sets of cells were treated with a range of concentrations of the designated compound to be tested as an inhibitor for 15 minutes. The cells were then stimulated with 100 ng/mL of EGF for 5 minutes and extracts made as described under the Western Blotting Procedure.

Irreversibility Test Protocol

A431 human epidermoid carcinoma cells were grown in 6-well plates to about 80% confluency and then incubated in serum-free media for 18 hours. Duplicate sets of cells were treated with 2 $\mu$M of designated compound to be tested as an irreversible inhibitor for either 1 or 2 hours. One set of cells was then stimulated with 100 ng/mL of EGF for 5 minutes and extracts made as described under the western blotting procedure. The other set of cells were washed free of the compound with warmed serum-free media, incubated for 2 hours, washed again, incubated another 2 hours, washed again, and then incubated a further 4 hours. This set of cells was then stimulated with EGF and extracts made similar to the first set of cells.

| Example Number | IC$_{50}$ (nM) EGFr (isolated enzyme assay) | IC$_{50}$ (nM) A431 Cell Autophosphorylation Assay | Irreversibility Test |
|---|---|---|---|
| 1 | 0.4 | 9.9 | yes, irreversible |

What is claimed is:
1. A compound having the Formula I

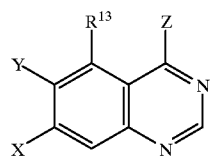

wherein X is —D—E—F and Y is —SR$^4$, halogen, —OR$^4$, —NHR$^3$ or hydrogen, or X is —SR$^4$, halogen, —OR$^4$, —NHR$^3$ or hydrogen, and Y is —D—E—F;

D is 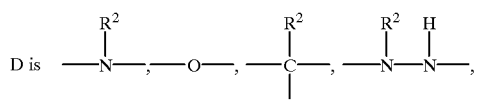

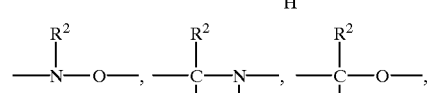

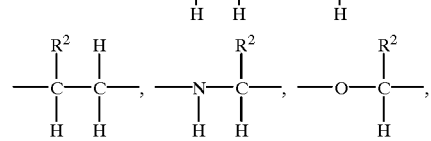

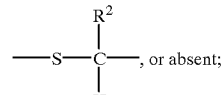

E is 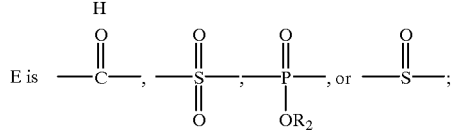

F is 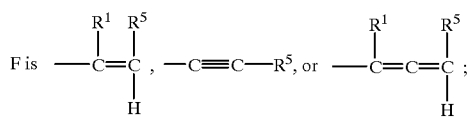

provided that when E is

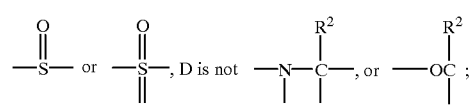

Z is 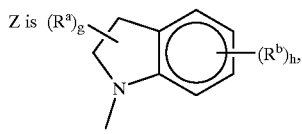

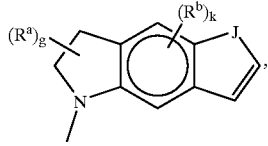

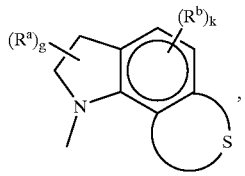

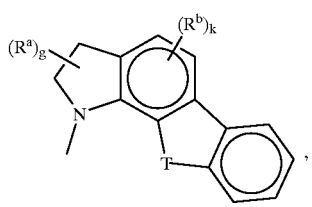

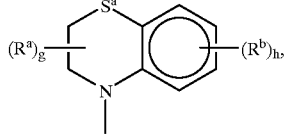

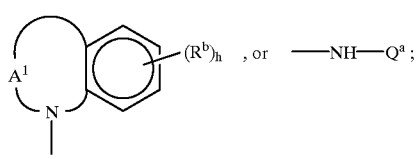

each R$^a$ is independently hydroxy, amino, N-mono- or N,N-di-(C$_1$–C$_4$) alkylamino, sulfo, or (C$_1$–C$_4$)alkoxy (provided that such groups are not attached to a ring carbon which is adjacent to an oxy, thio, or —N—), or R$^a$ is independently carboxy, hydroxy(C$_1$–C$_4$)alkyl, (C$_1$–C$_4$)alkoxy(C$_1$–C$_4$) alkyl, amino(C$_1$–C$_4$)alkyl, mono-N- or di-N,N-(C$_1$–C$_4$) alkylamino(C$_1$–C$_4$)alkyl, morpholino(C$_1$–C$_4$)alkyl, 4-(C$_1$–C$_4$)alkyl-piperazin-1-yl(C$_1$–C$_4$)alkyl, carboxy(C$_1$–C$_4$)alkyl, (C$_1$–C$_4$) alkoxycarbonyl, sulfo(C$_1$–C$_4$)alkyl or (C$_1$–C$_4$)alkyl;

each R$^b$ is independently mono-, di-, or trifluoromethyl, halo, nitro, hydroxy, amino, axido, isothiocyano, (C$_1$–C$_4$)alkyl, phenyl, thienyl, (C$_1$–C$_4$)alkoxy, benzyloxy, phenoxy, (C$_2$–C$_6$)alkenyl, (C$_2$–C$_6$)alkynyl, (C$_1$–C$_4$)alkylenedioxy, cyano, benzoylamino, trifluoromethylcarbonylamino, (C$_1$–C$_4$)alkanoylamino, (C$_1$–C$_4$)alkanoyl, N-mono- or N,N-di-(C$_1$–C$_4$) alkylamino, (C$_1$–C$_4$)alkylsulfonylamino, trifluoromethylsulfonylamino, (C$_1$–C$_4$)alkylthio, (C$_1$–C$_4$)alkylsulfinyl or (C$_1$–C$_4$)alkylsulfonyl, pyrrol-1-yl, piperidin-1-yl or pyrrolidin-1-yl, said phenyl, benzyloxy, phenoxy, and benzoylamino optionally monosubstituted with halo, nitro, trifluoromethyl, hydroxy, or ($C_1$–$C_4$)alkyl and said ($C_1$–$C_4$) alkylenedioxy is linked at both ends to adjacent carbons on the benzene moiety, or $R^b$ is —$Z^a R^{77}$;

J is —$CH_2$—, thio, —N(H)—, or oxy;

g is 0, 1, or 2;

h is 0 to 4;

k is 0, 1, or 2;

S completes a 5- or 6-membered aromatic or partially saturated ring that can contain an oxygen or sulfur atom;

T is —$CH_2$, —N(H)—, thio, or oxy;

$S^a$ is —$CH_2$—, oxy, or thio;

$A^1$ completes a 7- to 9-membered mono-unsaturated mono-aza ring;

$Q^a$ is a 9- or 10-membered bicyclic heterocyclic moiety, or a hydrogenated derivative thereof, containing one or two nitrogen heteroatoms and optionally containing a further heteroatom selected from nitrogen, oxygen and sulfur, or $Q^a$ is a 9- or 10-membered bicyclic aryl moiety, or a hydrogenated derivative thereof, which heterocyclic or aryl moiety, or hydrogenated derivatives thereof, may optionally bear one or two substituents selected from halogen, hydroxy, oxo, amino, nitro, carbamoyl, ($C_1$–$C_4$)alkyl, ($C_1$–$C_4$)alkoxy, ($C_1$–$C_4$) alkylamino, di-[($C_1$–$C_4$)alkyl]amino, and ($C_2$–$C_4$) alkanoylamino;

$R^1$ is hydrogen, halogen, or $C_1$–$C_6$ alkyl;

$R^2$, $R^3$, and $R^4$ are independently hydrogen, $C_1$–$C_6$ alkyl, —($CH_2$)$_n$—N-piperidinyl, —($CH_2$)$_n$—N-piperazinyl, —($CH_2$)$_n$—$N_1$-piperazinyl[$N_4$-($C_1$–$C_6$)alkyl], —($CH_2$)$_n$—N-pyrrolidyl, —($CH_2$)$_n$-pyridinyl, —($CH_2$)$_n$—N-imidazoyl, —($CH_2$)$_n$-imidazoyl, —($CH_2$)$_n$—N-morpholino, —($CH_2$)$_n$—N-thiomorpholino, —($CH_2$)$_n$—N-hexahydroazepine or substituted $C_1$–$C_6$ alkyl, wherein the substituents are selected from —OH, $NH_2$, or

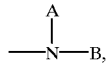

A and B are
independently hydrogen, $C_1$–$C_6$ alkyl, —($CH_2$)$_n$OH, —($CH_2$)$_n$—N-piperidinyl, —($CH_2$)$_n$—N-piperazinyl, —($CH_2$)$_n$—$N_1$-piperazinyl[$N_4$-($C_1$–$C_6$)alkyl], —($CH_2$)$_n$—N-pyrrolidyl, —($CH_2$)$_n$—N-pyridyl, —($CH_2$)$_n$-imidazoyl, or —($CH_2$)$_n$—N-imidazoyl;

$Z^1$, $Z^2$, or $Z^3$ are independently hydrogen, halogen, $C_1$–$C_6$ alkyl, $C_3$–$C_8$ cycloalkyl, $C_1$–$C_6$ alkoxy, $C_3$–$C_8$ cycloalkoxy, nitro, $C_1$–$C_6$ perfluoroalkyl, hydroxy, $C_1$–$C_6$ acyloxy, —$NH_2$, —NH($C_1$–$C_6$ alkyl), —N($C_1$–$C_6$ alkyl)$_2$, —NH($C_3$–$C_8$ cycloalkyl), —N($C_3$–$C_8$ cycloalkyl)$_2$, hydroxymethyl, $C_1$–$C_6$ acyl, cyano, azido, $C_1$–$C_6$ thioalkyl, $C_1$–$C_6$ sulfinylalkyl, $C_1$–$C_6$ sulfonylalkyl, $C_3$–$C_8$ thiocycloalkyl, $C_3$–$C_8$ sulfinylcycloalkyl, $C_3$–$C_8$ sulfonylcycloalkyl, mercapto, $C_1$–$C_6$ alkoxycarbonyl, $C_3$–$C_8$ cycloalkoxycarbonyl, $C_2$–$C_4$ alkenyl, $C_4$–$C_8$ cycloalkenyl, or $C_2$–$C_4$ alkynyl;

$Z^a$ is a bond, —$CH_2$—, —S—, $SO_2$, —NH—, —O—, —$OCH_2$—, —S—$CH_2$—, —$SO_2$—, or —$CH_2CH_2$—;

$R^{77}$ is phenyl, substituted phenyl, or a 5- to 10-membered optionally $R^3$ is hydrogen or halogen substituted heterocyclic aromatic ring;

$R^5$ is hydrogen, halogen, $C_1$–$C_6$ perfluoroalkyl, 1,1-difluoro($C_1$–$C_6$)alkyl, $C_1$–$C_6$ alkyl, —($CH_2$)$_n$—N-piperidinyl, —($CH_2$)$_n$-piperazinyl, —($CH_2$)$_n$-piperazinyl[$N_4$-($C_1$–$C_6$)alkyl], —($CH_2$)$_n$—N-pyrrolidyl, —($CH_2$)$_n$-pyridinyl, —($CH_2$)$_n$—N-imidazoyl —($CH_2$)$_n$—N-morpholino, —($CH_2$)$_n$—N-thiomorpholino,

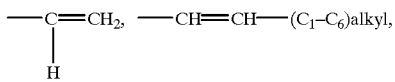

—($CH_2$)$_n$—N-hexahydroazepine, —($CH_2$)$_n$$NH_2$, —($CH_2$)$_n$NH ($C_1$–$C_6$alkyl), —($CH_2$)$_n$N($C_1$–$C_6$alkyl)$_2$, -1-oxo($C_1$–$C_6$)alkyl, carboxy, ($C_1$–$C_6$) alkyloxycarbonyl, N-($C_1$–$C_6$)alkylcarbamoyl, phenyl or substituted phenyl, wherein the substituted phenyl can have from one to three substituents independently selected from $Z^1$, $Z^2$, $Z^3$ or a monocyclic heteroaryl group, and each $C_1$–$C_6$ alkyl group can be substituted with —OH, —$NH_2$ or —NAB, where A and B are as defined above; and n is 1 to 4, and the pharmaceutically acceptable salts, esters, amides, and prodrugs thereof.

2. A compound of claim 1 wherein

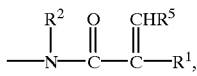

and Y is hydrogen, or X is hydrogen, and Y is

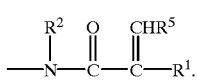

3. A compound of claim 1 wherein Y is —D—E—F and —D—E—F is

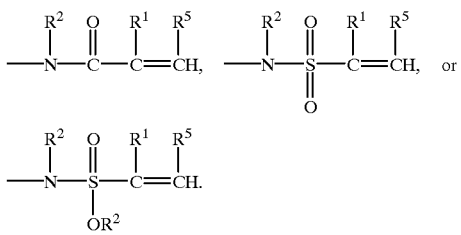

4. A compound of claim 1 wherein X is —D—E—F and —D—E—F is

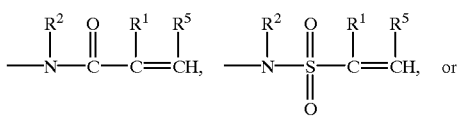

-continued

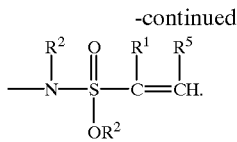

5. A compound of claim 3 wherein $R^2$ is hydrogen.

6. A compound of claim 4 wherein $R^2$ is hydrogen.

7. A compound of claim 3 wherein $R^2$ is $-(CH_2)_n$-morpholino.

8. A compound of claim 4 wherein $R^2$ is $-(CH_2)_n$-morpholino.

9. A compound of claim 3 wherein $R^5$ is carboxy, $(C_1-C_6)$ alkyloxycarbonyl or $C_1-C_6$ alkyl.

10. A compound of claim 1 wherein Y is —D—E—F, and X is $-O-(CH_2)_n$-morpholino.

11. A compound of claim 1 wherein Y is —D—E—F, and X is $-O-(CH_2)_n-N_1$-piperazinyl$[N_4-(C_1-C_6)$alkyl$]$.

12. A compound of claim 1 wherein Y is —D—E—F and X is $-O-(CH_2)_n$-imidazoyl.

13. A pharmaceutically acceptable composition that comprises a compound of claim 1.

14. A method of treating cancer, the method comprising administering to a patient having cancer a therapeutically effective amount of a compound of claim 1.

15. A method of treating or preventing restenosis, the method comprising administering to a patient having restenosis or at risk of having restenosis a therapeutically effective amount of a compound of claim 1.

16. A method of irreversibly inhibiting tyrosine kinases, the method comprising administering to a patient a tyrosine kinase inhibition a tyrosine kinase inhibiting amount of a compound of claim 1.

17. A method of treating psoriasis, the method comprising administering to a patient having psoriasis a therapeutically effective amount of a compound of claim 1.

18. A method of treating atherosclerosis, the method comprising administering to a patient having atherosclerosis a therapeutically effective amount of a compound of claim 1.

19. A method of treating endometriosis, the method comprising administering to a patient having endometriosis a therapeutically effective amount of a compound of claim 1.

20. A compound according to claim 1 wherein X is —D—E—F and F is

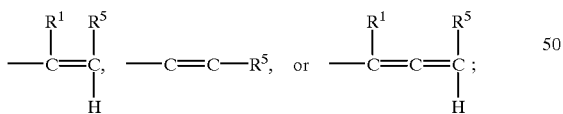

and $R^5$ is 1,1-difluoro$(C_1-C_6)$alkyl, $C_1-C_6$alkyl, $-(CH_2)_n$ —N-piperidinyl, $-(CH_2)_n$-piperazinyl, $-(CH_2)_n$-piperazinyl$[N_4-(C_1-C_6)$alkyl$]$, $-(CH_2)_n$—N-pyrrolidyl, $-(CH_2)_n$-pyridinyl, $-(CH_2)_n$—N-imidazoyl, $-(CH_2)_n$—N-morpholino, $-(CH_2)_n$—N-thiomorpholino, $-CH=CH-(C_1-C_6)$alkyl, $-(CH_2)_n$—N-hexahydroazepine, $-(CH_2)_nNH(C_1-C_6$ alkyl), $-(CH_2)_nN(C_1-C_6$ alkyl$)_2$, -1-oxo$(C_1-C_6)$alkyl, carboxy, $(C_1-C_6)$alkyloxycarbonyl, N-$(C_1-C_6)$alkylcarbamoyl, and each $C_1-C_1$ alkyl group of 1,1-difluoro$(C_1-C_6)$alkyl, $C_1-C_6$ alkyl, $-CH=CH-(C_1-C_6)$alkyl, -1-oxo$(C_1-C_6)$ alkyl, $(C_1-C_6)$alkyloxycarbonyl, or —N—$(C_1-C_6)$ alkylcarbamoyl is substituted with —OH, —NH$_2$, or —NAB, where A and B are as defined above; or Y is —D—E—F and F is

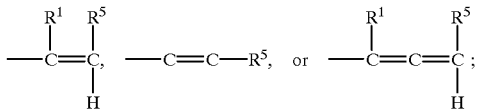

and $R^5$ is 1,1-difluoro$(C_1-C_6)$alkyl, $C_1-C_6$alkyl, $-(CH_2)_n$ —N-piperidinyl, $-(CH_2)_n$-piperazinyl, $-(CH_2)_n$-piperazinyl$[N_4-(C_1-C_6)$alkyl$]$, $-(CH_2)_n$—N-pyrrolidyl, $-(CH_2)_n$-pyridinyl, $-(CH_2)_n$—N-imidazoyl, $-(CH_2)_n$—N-morpholino, $-(CH_2)_n$—N-thiomorpholino, $-CH=CH-(C_1-C_6)$alkyl, $-(CH_2)_n$ —N-hexahydroazepine, $-(CH_2)_nNH_2$, $-(CH_2)_nNH(C_1-C_6$ alkyl), $-(CH_2)_nN(C_1-C_6$ alkyl$)_2$, -1-oxo$(C_1-C_6)$alkyl, carboxy, $(C_1-C_6)$ alkyloxycarbonyl, N-$(C_1-C_6)$alkylcarbamoyl, and each $C_1-C_1$ alkyl group of 1,1-difluoro$(C_1-C_6)$alkyl, $C_1-C_6$ alkyl, $-CH=CH-(C_1-C_6)$alkyl, -1-oxo$(C_1-C_6)$ alkyl, $(C_1-C_6)$alkyloxycarbonyl, or —N—$(C_1-C_6)$ alkylcarbamoyl is substituted with —OH, —NH$_2$, or —NAB, where A and B are as defined above.

21. A compound according to claim 1 wherein X is —D—E—F;

Y is —SR$^4$, —OR$^4$, or —NHR$^3$;

and $R^3$ and $R^4$ are $-(CH_2)_n$—N-piperidinyl, $-(CH_2)_n$—N-piperazinyl, $-(CH_2)_n-N_1$-piperazinyl$[N_4-(C_1-C_6)$alkyl$]$, $-(CH_2)_n$—N-pyrrolidyl, $-(CH_2)_n$-pyridinyl, $-(CH_2)_n$—N-imidazoyl, $-(CH_2)_n$-imidazoyl, $-(CH_2)_n$—N-morpholino, $-(CH_2)_n$—N-thiomorpholino, $-(CH_2)_n$—N-hexahydroazepine or substituted $C_1-C_6$alkyl, wherein the substituents are selected from —OH, —NH$_2$, or

A and B are
independently hydrogen, $C_1-C_6$ alkyl, $-(CH_2)_nOH$, $-(CH_2)_n$—N-piperidinyl, $-(CH_2)_n$—N-piperazinyl, $-(CH_2)_n-N_1$-piperazinyl$[N_4-(C_1-C_6)$alkyl$]$, $-(CH_2)_n$—N-pyrrolidyl, $-(CH_2)_n$—N-pyridyl, $-(CH_2)_n$-imidazoyl, or $-(CH_2)_n$—N-imidazoyl; or Y is —D—E—F;

X is —SR$^4$, —OR$^4$, or —NHR$^3$;

and $R^3$ and $R^4$ are $-(CH_2)_n$—N-piperidinyl, -$(CH_2)_n$—N-piperazinyl, $-(CH_2)_n-N_1$-piperazinyl$[N_4-(C_1-C_6)$alkyl$]$, $-(CH_2)_n$—N-pyrrolidyl, $-(CH_2)_n$-pyridinyl, $-(CH_2)_n$—N-imidazoyl, $-(CH_2)_n$-imidazoyl, $-(CH_2)_n$—N-morpholino, $-(CH_2)_n$—N-thiomorpholino, $-(CH_2)_n$—N-hexahydroazepine or substituted $C_1-C_6$ alkyl, wherein the substituents are selected from —OH, —NH$_2$, or

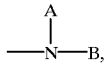

A and B are
independently hydrogen, $C_1-C_6$ alkyl, $-(CH_2)_nOH$, $-(CH_2)_n$—N-piperidinyl, $-(CH_2)_n$—N-piperazinyl, —(CH$_2$)$_n$—N$_1$-piperazinyl[N$_4$-(C$_1$–C$_6$)alkyl], —(CH$_2$)$_n$—N-pyrrolidyl, —(CH$_2$)$_n$—N-pyridyl, —(CH$_2$)$_n$-imidazoyl, or —(CH$_2$)$_n$—N-imidazoyl.

22. The compounds:

N-[4-(6-Bromo-2,3-dihydroindol-1-yl)quinazolin-6-yl] acrylamide;

N-[4-(6-Chloro-2,3-dihydroindol-1-yl)quinazolin-6-yl] acrylamide;

N-[4-(7-Chloro-3,4-dihydro-2H-quinolin-1-yl) quinazolin-6-yl]acrylamide;

N-[4-(6-Chloro-2,3-dihydroindol-1-yl)quinazolin-7-yl] acrylamide;

N-[4-(7-Chloro-3,4-dihydro-2H-quinolin-1-yl) quinazolin-7-yl]acrylamide;

N-[4-(6-Chloro-2,3-dihydroindol-1-yl)quinazolin-6-yl] propynamide;

N-[4-(7-Trifluoromethyl-3,4-dihydro-2H-quinolin-1-yl) quinazolin-6-yl]propynamide;

N-[4-(6-Chloro-2,3-dihydroindol-1-yl)quinazolin-7-yl] propynamide;

N-[4-(7-Trifluoromethyl-3,4-dihydro-2H-quinolin-1-yl) quinazolin-7-yl]propynamide;

N-[4-(4-6-Chloro-2,3-dihydroindol-1-yl)quinazolin-6-yl] but-2-ynamide;

N-[4-(6-Bromo-5-fluoro-2,3-dihydroindol-1-yl) quinazolin-6-yl]but-2-ynamide;

N-[4-(6-Chloro-2,3-dihydroindol-1-yl)quinazolin-6-yl] buta-2,3-dienamide;

N-[4-(6-Bromo-5-fluoro-2,3-dihydroindol-1-yl) quinazolin-6-yl]buta-2,3-dienamide;

N-[4-(6-Chloro-2,3-dihydroindol-1-yl)quinazolin-6-yl] but-2-enamide;

N-[4-(6-Ethynyl-2,3-dihydroindol-1-yl)quinazolin-6-yl] but-2-enamide;

N-[4-(6-Chloro-2,3-dihydroindol-1-yl)quinazolin-6-yl]-4,4,4-trifluorobut-2-enamide;

N-[4-(6-Nitro-2,3-dihydroindol-1-yl)quinazolin-6-yl]-4,4,4-trifluorobut-2-enamide;

N-[4-(6-Chloro-2,3-dihydroindol-1-yl)quinazolin-6-yl]-3-chloroacryl-amide;

N-[4-(6-Nitro-2,3-dihydroindol-1-yl)quinazolin-6-yl]-3-chloroacrylamide;

6-(S-Vinylsulfonamido)-4-(6-chloro-2,3-dihydroindol-1-yl)quinazoline;

6-(S-Vinylsulfonamido)-4-(6-pyrrol-1-yl-2,3-dihydroindol-1-yl)quinazoline;

N-[7-[3-(4-Morpholino)propoxy]-4-(6-chloro-2,3-dihydroindol-1-yl)quinazolin-6-yl]acrylamide;

N-[4-(6-Pyrrol-1-yl-2,3-dihydroindol-1-yl)-7-[4-(N,N-dimethylamino)butoxy]quinazolin-6-yl]acrylamide N-[7-[4-(N,N-dimethylamino)butoxy]-4-(6-chloro-2,3-dihydroindol-1-yl)quinazolin-6-yl]acrylamide;

N-[4-(Octahydroindol-1-yl)-7-[3-(4-morpholino) propoxy]-quinazolin-6-yl]acrylamide;

N-[4-(6-Chloro-2,3-dihydroindol-1-yl)quinazolin-6-yl]-4-oxopent-2-enamide;

N-[4-(Octahydroindol-1-yl)quinazolin-6-yl]-4-oxopent-2-enamide;

N-[4-(6-Chloro-2,3-dihydroindol-1-yl)quinazolin-6-yl]-4-hydroxy-4-oxobut-2-enamide;

N-[4-(6,7-Dihydro-5H-[1,3]dioxolo[4,5-f]indol-5-yl) quinazolin-6-yl]-4-hydroxy-4-oxobut-2-enamide;

N-[4-(6-Chloro-2,3-dihydroindol-1-yl)quinazolin-6-yl]-4-ethoxy-4-oxobut-2-enamide;

N-[4-(6,7-Dihydro-5H-[1,3]dioxolo[4,5-f]indol-5-yl) quinazolin-6-yl]-4-ethoxy-4-oxobut-2-enamide;

N-[4-(6-Chloro-2,3-dihydroindol-1-yl)quinazolin-6-yl]-4-(3-(N,N-dimethylamino)propoxy)-4-oxobut-2-enamide;

N-[4-(6-Methyl-2,3-dihydroindol-1-yl)quinazolin-6-yl]-4-(3-(N,N-dimethylamino)propoxy)-4-oxobut-2-enamide;

N-[4-(6-Chloro-2,3-dihydroindol-1-yl)quinazolin-6-yl]-4-(3-(N,N-dimethylamino)propylamino)-4-oxobut-2-enamide;

N-[4-(6-Methyl-2,3-dihydroindol-1-yl)quinazolin-6-yl]-4-(3-(N,N-dimethylamino)propylamino)-4-oxobut-2-enamide;

N-[4-(6-Chloro-2,3-dihydroindol-1-yl)quinazolin-6-yl]-4-(3-(4-morpholino)propoxy)-4-oxobut-2-enamide;

N-[4-(6-Azido-2,3-dihydroindol-1-yl)quinazolin-6-yl]-4-(3-(4-morpholino)propoxy)-4-oxobut-2-enamide;

N-[4-(6-Chloro-2,3-dihydroindol-1-yl)quinazolin-6-yl]-4-(3-(4-morpholino)propylamino)-4-oxobut-2-enamide;

N-[4-(6-Azido-2,3-dihydroindol-1-yl)quinazolin-6-yl]-4-(3-(4-morpholino)propylamino)-4-oxobut-2-enamide;

4,4-Difluoro-8-(morpholin-4-yl)oct-2-enoic acid [4-(6-chloro-2,3-dihydroindol-1-yl)quinazolin-6-yl]amide;

4,4-Difluoro-8-(morpholin-4-yl)oct-2-enoic acid [4-(5-benzyloxy-2,3-dihydroindol-1-yl)quinazolin-6-yl] amide;

Pent-2-enedioic acid 1{[4-(5-benzyloxy-2,3-dihydroindol-1-yl)quinazolin-6-yl]amide}5-[(3-morpholin-4-ylpropyl)amide];

Pent-2-enedioic acid 1{[4-(6-chloro-2,3-dihydroindol-1-yl)quinazolin-6-yl]amide}5-[(3-morpholin-4-ylpropyl) amide];

N-[4-(6-Chloro-2,3-dihydroindol-1-yl)quinazolin-6-yl]-4-(3-(morpholin-4-yl)propylthio)but-2-enamide;

N-[4-(5-Methoxy-2,3-dihydroindol-1-yl)quinazolin-6-yl]-4-(3-(morpholin-4-yl)propylthio)but-2-enamide;

7-Morpholin-4-ylhept-2-ynoic acid [4-(6-chloro-2,3-dihydroindol-1-yl)quinazolin-6-yl]amide;

7-Morpholin-4-ylhept-2-ynoic acid [4-(5-methoxy-2,3-dihydroindol-1-yl)quinazolin-6-yl]amide;

4-Morpholin-4-ylbut-2-ynoic acid [4-(6-chloro-2,3-dihydroindol-1-yl)quinazolin-6-yl]amide;

4-Morpholin-4-ylbut-2-ynoic acid [4-(2,3,4,5-tetrahydro-1H-benzoazepin-1-yl)quinazolin-6-yl]amide;

N-[4-(6-Chloro-2,3-dihydroindol-1-yl)pyrido[3,4-d] pyrimid-6-yl]acrylamide;

N-[4-(2,3,4,5-Tetrahydro-1H-benzoazepin-1-yl)pyrido[3,4-d]-pyrimid-6-yl]acrylamide;

N-[4-(6-Chloro-2,3-dihydroindol-1-yl)pyrido[4,3-d] pyrimid-7-yl]acrylamide;

N-[4-(5-Hydroxy-2,3-dihydroindol-1-yl)pyrido[4,3-d] pyrimid-7-yl]propynamide;

N-[4-(6-Chloro-2,3-dihydroindol-1-yl)pyrido[3,4-d] pyrimid-6-yl]propynamide;

N-[4-(5-Hydroxy-2,3-dihydroindol-1-yl)pyrido[3,4-d] pyrimid-6-yl]propynamide;

N-[4-(6-Chloro-2,3-dihydroindol-1-yl)pyrido[4,3-d] pyrimid-7-yl]propynamide;

N-[4-(5-Amino-2,3-dihydroindol-1-yl)pyrido[4,3-d]pyrimid-7-yl]propynamide;

N-[4-(6-Chloro-2,3-dihydroindol-1-yl)pyrido[3,4-d]pyrimid-6-yl]but-2-ynamide;

N-[4-(5-Amino-2,3-dihydroindol-1-yl)pyrido[3,4-d]pyrimid-6-yl]but-2-ynamide;

N-[4-(6-Chloro-2,3-dihydroindol-1-yl)pyrido[3,4-d]pyrimid-6-yl]buta-2,3-dienamide;

N-[4-(1,2,3,4,5,6-Hexahydrobenzo[b]azocin-1-yl)pyrido[3,4-d]-pyrimid-6-yl]buta-2,3-dienamide;

N-[4-(6-Chloro-2,3-dihydroindol-1-yl)pyrido[3,4-d]pyrimid-6-yl]but-2-enamide;

N-[4-(1,2,3,4,5,6-Hexahydrobenzo[b]azocin-1-yl)pyrido[3,4-d]-pyrimid-6-yl]but-2-enamide;

N-[4-(6-Chloro-2,3-dihydroindol-1-yl)pyrido[3,4-d]pyrimid-6-yl]-4,4,4-trifluorobut-2-enamide;

N-[4-(6-Fluoro-7-methyl-2,3-dihydroindol-1-yl)pyrido[3,4-d]-pyrimid-6-yl]-4,4,4-trifluorobut-2-enamide;

N-[4-(6-Chloro-2,3-dihydroindol-1-yl)pyrido[3,4-d]pyrimid-6-yl]-3-chloroacrylamide;

N-[4-(6-Fluoro-7-methyl-2,3-dihydroindol-1-yl)pyrido[3,4-d]-pyrimid-6-yl]-3-chloroacrylamide;

6-(S-Vinylsulfonamido)-4-(6-chloro-2,3-dihydroindol-1-yl)-pyrido[3,4-d]pyrimidine;

6-(S-Vinylsulfonamido)-4-(2,3,6,7,8,9-hexahydro-1H-benzo[g]indol-1-yl)pyrido[3,4-d]pyrimidine;

N-[4-(6-Chloro-2,3-dihydroindol-1-yl)pyrido[3,4-d]pyrimid-6-yl]-4-oxopent-2-enamide;

N-[4-(2,3,6,7,8,9-Hexahydro-1H-benzo[g]indol-1-yl)pyrido[3,4d]-pyrimid-6-yl]-4-oxopent-2-enamide;

N-[4-(6-Chloro-2,3-dihydroindol-1-yl)pyrido[3,4-d]pyrimid-6-yl]-4-hydroxy-4-oxobut-2-enamide;

N-[4-(6-Ethynyl-2,3-dihydroindol-1-yl)pyrido[3,4-d]pyrimid-6-yl]-4-hydroxy-4-oxobut-2-enamide;

N-[4-(6-Chloro-2,3-dihydroindol-1-yl)pyrido[3,4-d]pyrimid-6-yl]-4-ethoxy-4-oxobut-2-enamide;

N-[4-(6-Ethynyl-2,3-dihydroindol-1-yl)pyrido[3,4-d]pyrimid-6-yl]-4-ethoxy-4-oxobut-2-enamide;

N-[4-(6-Chloro-2,3-dihydroindol-1-yl)pyrido[3,4-d]pyrimid-6-yl]-4-(3-(N,N-dimethylamino)propoxy)-4-oxobut-2-enamide;

N-[4-(6-Ethynyl-2,3-dihydroindol-1-yl)pyrido[3,4-d]pyrimid-6-yl]-4-(3-(N,N-dimethylamino)propoxy)-4-oxobut-2-enamide;

N-[4-(6-Chloro-2,3-dihydroindol-1-yl)pyrido[3,4-d]pyrimid-6-yl]-4-(3-(N,N-dimethylamino)propylamino)-4-oxobut-2-enamide;

N-[4-(6-Ethynyl-2,3-dihydroindol-1-yl)pyrido[3,4-d]pyrimid-6-yl]-4-(3-(N,N-dimethylamino)propylamino)-4-oxobut-2-enamide;

N-[4-(6-Chloro-2,3-dihydroindol-1-yl)pyrido[3,4-d]pyrimid-6-yl]-4-(3-(4-morpholino)propoxy)-4-oxobut-2-enamide;

N-[4-(6-Ethynyl-2,3-dihydroindol-1-yl)pyrido[3,4-d]pyrimid-6-yl]-4-(3-(4-morpholino)propoxy)-4-oxobut-2-enamide;

N-[4-(6-Chloro-2,3-dihydroindol-1-yl)pyrido[3,4-d]pyrimid-6-yl]-4-(3-(4-morpholino)propylamino)-4-oxobut-2-enamide;

N-[4-(6-Ethynyl-2,3-dihydroindol-1-yl)pyrido[3,4-d]pyrimid-6-yl]-4-(3-(4-morpholino)propylamino)-4-oxobut-2-enamide;

4,4-Difluoro-8-(morpholin-4-yl)oct-2-enoic acid [4-(6-chloro-2,3-dihydroindol-1-yl)pyrido[3,4-d]pyrimid-6-yl]amide;

4,4-Difluoro-8-(morpholin-4-yl)oct-2-enoic acid [4-(6-Ethynyl-2,3-dihydroindol-1-yl)pyrido[3,4-d]pyrimid-6-yl]amide;

Pent2-enedioic acid 1{[4-(2,3-dihydropyrrolo[2,3-f]indol-7-yl)pyrido[3,4-d]pyrimid-6-yl]amide}5-[(3-morpholin-4-ylpropyl)amide];

Pent-2-enedioic acid 1{[4-(6-chloro-2,3-dihydroindol-1-yl)pyrido[3,4-d]pyrimid-6-yl]amide}5-[(3-morpholin-4-ylpropyl)amide];

N-[4-(6-Chloro-2,3-dihydroindol-1-yl)pyrido[3,4-d]pyrimid-6-yl]-4-(3-(morpholin-4-yl)propylthio)but-2-enamide;

N-[4-(2,3-Dihydropyrrolo[2,3-f]indol-7-yl)pyrido[3,4-d]pyrimid-6-yl]-4-(3-(morpholin-4-yl)propylthio)but-2-enamide;

7-Morpholin-4-ylhept-2-ynoic acid [4-(6-chloro-2,3-dihydroindol-1-yl)pyrido[3,4-d]pyrimid-6-yl]amide;

7-Morpholin-4-ylhept-2-ynoic acid [4-(2,3,5,6-tetrahydropyrrolo[2,3-f]indol-1-yl)pyrido[3,4-d]pyrimid-6-yl]amide;

4-Morpholin-4-ylbut-2-ynoic acid [4-(6-chloro-2,3-dihydroindol-1-yl)pyrido[3,4-d]pyrimid-6-yl]amide;

4-Morpholin-4-ylbut-2-ynoic acid [4-(2,3,5,6-tetrahydropyrrolo[2,3-f]indol-1-yl)pyrido[3,4-d]pyrimid-6-yl]amide;

N-[4-(6-Chloro-2,3-dihydroindol-1-yl)benzo[b]thieno[3,2-d]-pyrimid-6-yl]acrylamide;

N-[4-(6-Ethynyl-2,3-dihydroindol-1-yl) benzo[b]thieno[3,2-d]-pyrimid-6-yl]acrylamide;

[4-(6-Chloro-2,3-dihydroindol-1-yl)quinazolin-6-yl] acrylate;

[4-(2,3,5,6-Tetrahydropyrrolo[2,3-f]indol-1-yl)quinazolin-6-yl]acrylate;

[4-(6-Chloro-2,3-dihydroindol-1-yl)quinazolin-7-yl] acrylate;

[4-(6-Ethynyl-2,3-dihydroindol-1-yl)quinazolin-7-yl] acrylate;

[7-[3-(4-Morpholino)propoxy]-4-(6-chloro-2,3-dihydroindol-1-yl)quinazolin-6-yl]acrylate;

[4-(-(2,3-Dihydropyrrolo[2,3-f]indol-7-yl)-7-[4-(N,N-dimethylamino)butoxy]quinazolin-6-yl]acrylate;

[7-[4-(N,N-dimethylamino)butoxy]-4-(6-chloro-2,3-dihydroindol-1-yl)quinazolin-6-yl]acrylate;

[4-(6-Ethynyl-2,3-dihydroindol-1-yl)-7-[3-(4-morpholino)-propoxy]quinazolin-6-yl]acrylate;

N-(3-(4-Morpholino)propylamino)-4,O-[4-(6-chloro-2,3-dihydroindol-1-yl)quinazolin-6-yl]-4-oxobut-2-enamide;

N-(3-(4-Morpholino)propylamino)-4,O-[4-(2,3,4,5-tetrahydro-1H-benzoazepin-1-yl)quinazolin-6-yl]-4-oxobut-2-enamide;

4,4-Difluoro-8-(morpholin-4-yl)oct-2-enoic acid [4-(6-chloro-2,3-dihydroindol-1-yl)quinazolin-6-yl]ester;

4,4-Difluoro-8-(morpholin-4-yl)oct-2-enoic acid [4-(6-bromo-2,3-dihydroindol-1-yl)quinazolin-6-yl]ester;

Pent-2-enedioic acid 1{[4-(6-methyl-2,3-dihydroindol-1-yl)quinazolin-6-yl]ester}5-[(3-morpholin-4-ylpropyl)amide];

Pent-2-enedioic acid 1{[4-(6-chloro-2,3-dihydroindol-1-yl)quinazolin-6-yl]ester}5-[(3-morpholin-4-ylpropyl)amide];

[4-(6-Chloro-2,3-dihydroindol-1-yl)quinazolin-6-yl]-4-(3-(morpholin-4-yl)propylthio)but-2-enoate;
[4-(6-Fluoro-2,3-dihydroindol-1-yl)quinazolin-6-yl]-4-(3-(morpholin-4-yl)propylthio)but-2-enoate;
7-Morpholin-4-ylhept-2-ynoic acid [4-(6-chloro-2,3-dihydroindol-1-yl)quinazolin-6-yl]ester;
7-Morpholin-4-ylhept-2-ynoic acid [4-(6-chloro-7-fluoro-2,3-dihydroindol-1-yl)quinazolin-6-yl]ester;
4-Morpholin-4-ylbut-2-ynoic acid [4-(6-chloro-2,3-dihydroindol-1-yl)quinazolin-6-yl]ester;
4-Morpholin-4-ylbut-2-ynoic acid [4-(6-ethynyl-2,3-dihydroindol-1-yl)quinazolin-6-yl]ester;
N-[4-(Quinol-2-ylamino)quinazolin-6-yl]acrylamide;
N-[4-(Indol-5-ylamino)quinazolin-6-yl]acrylamide;
N-[4-(Quinol-2-ylamino)quinazolin-7-yl]acrylamide;
N-[4-(Indol-5-ylamino)quinazolin-7-yl]acrylamide;
N-[4-(Quinol-3-ylamino)quinazolin-6-yl]propynamide;
N-[4-(Indol-5-ylamino)quinazolin-6-yl]propynamide;
N-[4-(Quinol-3-ylamino)quinazolin-7-yl]propynamide;
N-[4-(Indol-5-ylamino)quinazolin-7-yl]propynamide;
N-[4-(Quinol-5-ylamino)quinazolin-6-yl]but-2-ynamide;
N-[4-(Indol-5-ylamino)quinazolin-6-yl]but-2-ynamide;
N-[4-(Quinol-5-ylamino)quinazolin-6-yl]buta-2,3-dienamide;
N-[4-(Indol-5-ylamino)quinazolin-6-yl]buta-2,3-dienamide;
N-[4-(Quinol-6-ylamino)quinazolin-6-yl]but-2-enamide;
N-[4-(Indol-5-ylamino)quinazolin-6-yl]but-2-enamide;
N-[4-(Quinol-6-ylamino)quinazolin-6-yl]-4,4,4-trifluorobut-2-enamide;
N-[4-(Indol-5-ylamino)quinazolin-6-yl]-4,4,4-trifluorobut-2-enamide;
N-[4-(Quinol-7-ylamino)quinazolin-6-yl]-3-chloroacrylamide;
N-[4-(Indol-5-ylamino)quinazolin-6-yl]-3-chloroacrylamide;
6-(S-Vinylsulfonamido)-4-(quinol-7-ylamino)quinazoline;
6-(S-Vinylsulfonamido)-4-(indol-5-ylamino)quinazoline;
N-[7-[3-(4-Morpholino)propoxy]-4-(quinol-8-ylamino)quinazolin-6-yl]acrylamide;
N-[4-(Indol-5-ylamino)-7-[4-(N,N-dimethylamino)butoxy]-quinazolin-6-yl]acrylamide;
N-[7-[4-(N,N-dimethylamino)butoxy]-4-(quinol-8-ylamino)-quinazolin-6-yl]acrylamide;
N-[4-(Indol-5-ylamino)-7-[3-(4-morpholino)propoxy]quinazolin-6-yl]acrylamide;
N-[4-(Isoquinol-1-ylamino)quinazolin-6-yl]-4-oxopent-2-enamide;
N-[4-(Indol-5-ylamino)quinazolin-6-yl]-4-oxopent-2-enamide;
N-[4-(Isoquinol-1-ylamino)quinazolin-6-yl]-4-hydroxy-4-oxobut-2-enamide;
N-[4-(Indol-5-ylamino)quinazolin-6-yl]-4-hydroxy-4-oxobut-2-enamide;
N-[4-(Isoquinol-5-ylamino)quinazolin-6-yl]-4-ethoxy-4-oxobut-2-enamide;
N-[4-(Indol-5-ylamino)quinazolin-6-yl]-4-ethoxy-4-oxobut-2-enamide;
N-[4-(Isoquinol-5-ylamino)quinazolin-6-yl]-4-(3-(N,N-dimethylamino)propoxy)-4-oxobut-2-enamide;
N-[4-(Indol-5-ylamino)quinazolin-6-yl]-4-(3-(N,N-dimethylamino)-propoxy)-4-oxobut-2-enamide;
N-[4-(Indol-4-ylamino)quinazolin-6-yl]-4-(3-(N,N-dimethylamino)propylamino)-4-oxobut-2-enamide;
N-[4-(Indol-5-ylamino)quinazolin-6-yl]-4-(3-(N,N-dimethylamino)propylamino)-4-oxobut-2-enamide;
N-[4-(Indol-4-ylamino)quinazolin-6-yl]-4-(3-(4-morpholino)propoxy)-4-oxobut-2-enamide;
N-[4-(Indol-5-ylamino)quinazolin-6-yl]-4-(3-(4-morpholino)propoxy)-4-oxobut-2-enamide;
N-[4-(Indol-6-ylamino)quinazolin-6-yl]-4-(3-(4-morpholino)propylamino)-4-oxobut-2-enamide;
N-[4-(Indol-5-ylamino)quinazolin-6-yl]-4-(3-(4-morpholino)propylamino)-4-oxobut-2-enamide;
4,4-Difluoro-8-(morpholin-4-yl)oct-2-enoic acid [4-(indol-6-ylamino)quinazolin-6-yl]amide;
4,4-Difluoro-8-(morpholin-4-yl)oct-2-enoic acid [4-(indol-5-ylamino)quinazolin-6-yl]amide;
Pent-2-enedioic acid 1{[4-(indol-5-ylamino)quinazolin-6-yl]amide}5-[(3-morpholin-4-ylpropyl)amide];
Pent-2-enedioic acid 1{[4-(1H-indazol-6-ylamino)quinazolin-6-yl]amide}5-[(3-morpholin-4-ylpropyl)amide];
N-[4-(1H-Indazol-6-ylamino)quinazolin-6-yl]-4-(3-(morpholin-4-yl)propylthio)but-2-enamide;
N-[4-(Indol-5-ylamino)quinazolin-6-yl]-4-(3-(morpholin-4-yl)propylthio)but-2-enamide;
7-Morpholin-4-ylhept-2-ynoic acid [4-(1H-indazol-5-ylamino)quinazolin-6-yl]amide;
7-Morpholin-4-ylhept-2-ynoic acid [4-(indol-5-ylamino)quinazolin-6-yl]amide;
4-Morpholin-4-ylbut-2-ynoic acid [4-(1H-indazol-5-ylamino)quinazolin-6-yl]amide;
4-Morpholin-4-ylbut-2-ynoic acid [4-(4-benzyloxyphenylamino)quinazolin-6-yl]amide;
N-[4-(1H-Indazol-4-ylamino)pyrido[3,4-d]pyrimid-6-yl]acrylamide;
N-[4-(Indol-5-ylamino)pyrido[3,4-d]pyrimid-6-yl]acrylamide;
N-[4-(1H-Indazol-4-ylamino)pyrido[4,3-d]pyrimid-7-yl]acrylamide;
N-[4-(Indol-5-ylamino)pyrido[4,3-d]pyrimid-7-yl]propynamide;
N-[4-(1H-Indazol-4-ylamino)pyrido[3,4-d]pyrimid-6-yl]propynamide;
N-[4-(Indol-5-ylamino)pyrido[3,4-d]pyrimid-6-yl]propynamide;
N-[4-(1H-Benzotriazol-5-ylamino)pyrido[4,3-d]pyrimid-7-yl]propynamide;
N-[4-(Indol-5-ylamino)pyrido[4,3-d]pyrimid-7-yl]propynamide;
N-[4-(1H-Benzotriazol-5-ylamino)pyrido[3,4-d]pyrimid-6-yl]but-2-ynamide;
N-[4-(Indol-5-ylamino)pyrido[3,4-d]pyrimid-6-yl]but-2-ynamide;
N-[4-(1H-Benzotriazol-5-ylamino)pyrido[3,4-d]pyrimid-6-yl]buta-2,3-dienamide;
N-[4-(Indol-5-ylamino)pyrido[3,4-d]pyrimid-6-yl]buta-2,3-dienamide;
N-[4-(1H-Benzotriazol-7-ylamino)pyrido[3,4-d]pyrimid-6-yl]but-2-enamide;
N-[4-(Indol-5-ylamino)pyrido[3,4-d]pyrimid-6-yl]but-2-enamide;

N-[4-(1H-Benzotriazol-7-ylamino)pyrido[3,4-d]pyrimid-6-yl]-4,4,4-trifluorobut-2-enamide;

N-[4-(Indol-5-ylamino)pyrido[3,4-d]pyrimid-6-yl]-4,4,4-trifluorobut-2-enamide;

N-[4-(1H-Benzotriazol-7-ylamino)pyrido[3,4-d]pyrimid-6-yl]-3-chloroacrylamide;

N-[4-(Indol-5-ylamino)pyrido[3,4-d]pyrimid-6-yl]-3-chloroacrylamide;

6-(S-Vinylsulfonamido)-4-(benzothiazol-5-ylamino)pyrido[3,4-d]-pyrimidine;

6-(S-Vinylsulfonamido)-4-(indol-5-ylamino)pyrido[3,4-d]-pyrimidine;

N-[4-(Benzothiazol-5-ylamino)pyrido[3,4-d]pyrimid-6-yl]-4-oxopent-2-enamide;

N-[4-(Indol-5-ylamino)pyrido[3,4-d]pyrimid-6-yl]-4-oxopent-2-enamide;

N-[4-(Benzothiazol-6-ylamino)pyrido[3,4-d]pyrimid-6-yl]-4-hydroxy-4-oxobut-2-enamide;

N-[4-(Indol-5-ylamino)pyrido[3,4-d]pyrimid-6-yl]-4-hydroxy-4-oxobut-2-enamide;

N-[4-(Benzothiazol-6-ylamino)pyrido[3,4-d]pyrimid-6-yl]-4-ethoxy-4-oxobut-2-enamide;

N-[4-(Indol-5-ylamino)pyrido[3,4-d]pyrimid-6-yl]-4-ethoxy-4-oxobut-2-enamide;

N-[4-(Indan-4-ylamino)pyrido[3,4-d]pyrimid-6-yl]-4-(3-(N,N-dimethylamino)propoxy)-4-oxobut-2-enamide;

N-[4-(Indol-5-ylamino)pyrido[3,4-d]pyrimid-6-yl]-4-(3-(N,N-dimethylamino)propoxy)-4-oxobut-2-enamide;

N-[4-(Indan-4-ylamino)pyrido[3,4-d]pyrimid-6-yl]-4-(3-(N,N-dimethylamino)propylamino)-4-oxobut-2-enamide;

N-[4-(Indol-5-ylamino)pyrido[3,4-d]pyrimid-6-yl]-4-(3-(N,N-dimethylamino)propylamino)-4-oxobut-2-enamide;

N-[4-(Indan-5-ylamino)pyrido[3,4-d]pyrimid-6-yl]-4-(3-(4-morpholino)propoxy)-4-oxobut-2-enamide;

N-[4-(Indol-5-ylamino)pyrido[3,4-d]pyrimid-6-yl]-4-(3-(4-morpholino)propoxy)-4-oxobut-2-enamide;

N-[4-(Indan-5-ylamino)pyrido[3,4-d]pyrimid-6-yl]-4-(3-(4-morpholino)propylamino)-4-oxobut-2-enamide;

N-[4-(Indol-5-ylamino)pyrido[3,4-d]pyrimid-6-yl]-4-(3-(4-morpholino)propylamino)-4-oxobut-2-enamide;

4,4-Difluoro-8-(morpholin-4-yl)oct-2-enoic acid [4-(1,2,3,4-tetrahydronaphth-1-ylamino)pyrido[3,4-d]pyrimid-6-yl]amide;

4,4-Difluoro-8-(morpholin-4-yl)oct-2-enoic acid [4-(indol-5-ylamino)pyrido[3,4-d]pyrimid-6-yl]amide;

Pent-2-enedioic acid 1{[4-(indol-5-ylamino)pyrido[3,4-d]pyrimid-6-yl]amide}5-[(3-morpholin-4-ylpropyl)amide];

Pent-2-enedioic acid 1{[4-(1,2,3,4-tetrahydronaphth-1-ylamino)pyrido[3,4-d]pyrimid-6-yl]amide}5-[(3-morpholin-4-ylpropyl)amide];

N-[4-(1,2,3,4-Tetrahydronaphth-2-ylamino)pyrido[3,4-d]pyrimid-6-yl]-4-(3-(morpholin-4-yl)propylthio)but-2-enamide;

N-[4-(Indol-5-ylamino)pyrido[3,4-d]pyrimid-6-yl]-4-(3-(morpholin-4-yl)propylthio)but-2-enamide;

7-Morpholin-4-ylhept-2-ynoic acid [4-(1,2,3,4-tetrahydronaphth-2-ylamino)pyrido[3,4-d]pyrimid-6-yl]amide;

7-Morpholin-4-ylhept-2-ynoic acid [4-(indol-5-ylamino)pyrido[3,4-d]pyrimid-6-yl]amide;

4-Morpholin-4-ylbut-2-ynoic acid [4-(benzo[c][2,1,3]thiadiazol-4-ylamino)pyrido[3,4-d]pyrimid-6-yl]amide;

4-Morpholin-4-ylbut-2-ynoic acid [4-(indol-5-ylamino)pyrido[3,4-d]pyrimid-6-yl]amide;

N-[4-(Benzo[c][2,1,3]thiadiazol-4-ylamino)benzo[b]thieno[3,2-d]-pyrimid-6-yl]acrylamide;

N-[4-(Indol-5-ylamino)benzo[b]thieno[3,2-d]pyrimid-6-yl]acrylamide;

[4-(Benzimidazol-5-ylamino)quinazolin-6-yl]acrylate;

[4-(Indol-5-ylamino)quinazolin-6-yl]acrylate;

[4-(Benzimidazol-5-ylamino)quinazolin-7-yl]acrylate;

[4-(Indol-5-ylamino)quinazolin-7-yl]acrylate;

[7-[3-(4-Morpholino)propoxy]-4-(benzimidazol-5-ylamino)quinazolin-6-yl]acrylate;

[4-(Indol-5-ylamino)-7-[4-(N,N-dimethylamino)butoxy]quinazolin-6-yl]acrylate;

[7-[4-(N,N-dimethylamino)butoxy]-4-(6-methoxyquinol-8-ylamino)quinazolin-6-yl]acrylate;

[4-(Indol-5-ylamino)-7-[3-(4-morpholino)propoxy]quinazolin-6-yl]acrylate;

N-(3-(4-Morpholino)propylamino)-4,O-[4-(6-methoxyquinol-8-ylamino)quinazolin-6-yl]-4-oxobut-2-enamide;

N-(3-(4-Morpholino)propylamino)-4,O-[4-(indol-5-ylamino)quinazolin-6-yl]-4-oxobut-2-enamide;

4,4-Difluoro-8-(morpholin-4-yl)oct-2-enoic acid [4-(1-methylindol-5-ylamino)quinazolin-6-yl]ester;

4,4-Difluoro-8-(morpholin-4-yl)oct-2-enoic acid [4-(indol-5-ylamino)quinazolin-6-yl]ester;

Pent-2-enedioic acid 1{[4-(indol-5-ylamino)quinazolin-6-yl]ester}5-[(3-morpholin-4-ylpropyl)amide];

Pent-2-enedioic acid 1{[4-(1-methylindol-5-ylamino)quinazolin-6-yl]ester}5-[(3-morpholin-4-ylpropyl)amide];

[4-(2-Methylindol-5-ylamino)quinazolin-6-yl]-4-(3-(morpholin-4-yl)propylthio)but-2-enoate;

[4-(Indol-5-ylamino)quinazolin-6-yl]-4-(3-(morpholin-4-yl)propylthio)but-2-enoate;

7-Morpholin-4-ylhept-2-ynoic acid [4-(3-cyanoindol-5-ylamino)quinazolin-6-yl]ester;

7-Morpholin-4-ylhept-2-ynoic acid [4-(indol-5-ylamino)quinazolin-6-yl]ester;

4-Morpholin-4-ylbut-2-ynoic acid [4-(benzothien-5-ylamino)quinazolin-6-yl]ester;

4-Morpholin-4-ylbut-2-ynoic acid [4-(indol-5-ylamino)quinazolin-6-yl]ester;

N-[4-(1-Benzylindol-5-ylamino)quinazolin-6-yl]acrylamide;

N-[4-(2-Benzylbenzimidazol-5-ylamino)quinazolin-6-yl]acrylamide;

N-[4-(1-Benzylindol-5-ylamino)quinazolin-7-yl]acrylamide;

N-[4-(2-Benzylbenzimidazol-5-ylamino)quinazolin-7-yl]acrylamide;

N-[4-(2-Benzylbenzindazol-5-ylamino)quinazolin-6-yl]propynamide;

N-[4-(1-Benzylbenzindazol-5-ylamino)quinazolin-6-yl] propynamide;

N-[4-(2-Benzylbenzindazol-5-ylamino)quinazolin-7-yl] propynamide;

N-[4-(2-Benzylbenzindazol-5-ylamino)quinazolin-7-yl] propynamide;

N-[4-(1-Phenylsulfonylindol-5-ylamino)quinazolin-6-yl] but-2-ynamide;

N-[4-(1-Phenylsulfonylindol-5-ylamino)quinazolin-6-yl] buta-2,3-dienamide;

N-[4-(1-Benzylindol-5-ylamino)quinazolin-6-yl]but-2-enamide;

N-[4-(2-Benzylbenzindazol-5-ylamino)quinazolin-6-yl]-4,4,4-trifluorobut-2-enamide;

N-[4-(1-Benzylindol-5-ylamino)quinazolin-6-yl]-4,4,4-trifluorobut-2-enamide;

N-[4-(1-Benzylindol-6-ylamino)quinazolin-6-yl]-3-chloroacrylamide;

6-(S-Vinylsulfonamido)-4-(2-benzylbenzindazol-5-ylamino)quinazoline;

N-[7-[3-(4-Morpholino)propoxy]-4-(2-benzylbenzindazol-5-ylamino)quinazolin-6-yl] acrylamide;

N-[4-(1-Benzylindol-6-ylamino)-7-[4-(N,N-dimethylamino)butoxy]quinazolin-6-yl]acrylamide;

N-[4-(2-Phenylbenzimidazol-5-ylamino)-7-[3-(4-morpholino)propoxy]quinazolin-6-yl]acrylamide;

N-[4-(2-Phenylbenzimidazol-5-ylamino)quinazolin-6-yl]-4-oxopent-2-enamide;

N-[4-(3-Benzylbenzimidazol-5-ylamino)quinazolin-6-yl]-4-hydroxy-4-oxobut-2-enamide;

N-[4-(3-Benzylbenzimidazol-5-ylamino)quinazolin-6-yl]-4-ethoxy-4-oxobut-2-enamide;

N-[4-(2-Benzylbenzindazol-5-ylamino)quinazolin-6-yl]-4-(3-(N,N-dimethylamino)propoxy)-4-oxobut-2-enamide;

N-[4-(2-Benzylbenzindazol-5-ylamino)quinazolin-6-yl]-4-(3-(N,N-dimethylamino)propylamino)-4-oxobut-2-enamide;

N-[4-(1-Benzylbenzimidazol-5-ylamino)quinazolin-6-yl]-4-(3-(N,N-dimethylamino)propylamino)-4-oxobut-2-enamide;

N-[4-(1-Benzylbenzimidazol-5-ylamino)quinazolin-6-yl]-4-(3-(4-morpholino)propoxy)-4-oxobut-2-enamide;

N-[4-(2-Benzylbenzindazol-5-ylamino)quinazolin-6-yl]-4-(3-(4-morpholino)propoxy)-4-oxobut-2-enamide;

N-[4-(42-Benzylbenzindazol-5-ylamino)quinazolin-6-yl]-4-(3-(4-morpholino)propylamino)-4-oxobut-2-enamide;

N-[4-(2-Benzylbenzotriazol-5-ylamino)quinazolin-6-yl]-4-(3-(4-morpholino)propylamino)-4-oxobut-2-enamide;

4,4-Difluoro-8-(morpholin-4-yl)oct-2-enoic acid [4-(2-benzylbenzotriazol-5-ylamino)quinazolin-6-yl]amide;

4,4-Difluoro-8-(morpholin-4-yl)oct-2-enoic acid [4-(2-benzylbenzindazol-5-ylamino)quinazolin-6-yl]amide;

Pent-2-enedioic acid 1{[4-(2-benzylbenzindazol-5-ylamino)quinazolin-6-yl]amide}5-[(3-morpholin-4-ylpropyl)amide];

Pent-2-enedioic acid 1{[4-(2-benzylbenzindazol-5-ylamino)quinazolin-6-yl]amide}5-[(3-morpholin-4-ylpropyl)amide];

N-[4-(1-Benzylbenzotriazol-5-ylamino)quinazolin-6-yl]-4-(3-(morpholin-4-yl)propylthio)but-2-enamide;

N-[4-(2-Benzylbenzindazol-5-ylamino)quinazolin-6-yl]-4-(3-(morpholin-4-yl)propylthio)but-2-enamide;

7-Morpholin-4-ylhept-2-ynoic acid [4-(1-Benzylbenzotriazol-5-ylamino)quinazolin-6-yl]amide;

4-Morpholin-4-ylbut-2-ynoic acid [4-(3-benzylbenzotriazol-5-ylamino)quinazolin-6-yl]amide;

4-Morpholin-4-ylbut-2-ynoic acid [4-(2-benzylbenzindazol-5-ylamino)quinazolin-6-yl]amide;

N-[4-(2-Benzylbenzindazol-5-ylamino)pyrido[3,4-d]pyrimid-6-yl]acrylamide;

N-[4-(3-Benzylbenzotriazol-5-ylamino)pyrido[3,4-d]pyrimid-6-yl]acrylamide;

N-[4-(2-{Pyrid-2-yl}benzotriazol-5-ylamino)pyrido[3,4-d]pyrimid-6-yl]propynamide;

N-[4-(2-Benzylbenzindazol-5-ylamino)pyrido[3,4-d]pyrimid-6-yl]propynamide;

N-[4-(2-{Pyrid-2-yl}benzotriazol-5-ylamino)pyrido[3,4-d]pyrimid-6-yl]but-2-ynamide;

N-[4-(2-Benzylbenzindazol-5-ylamino)pyrido[3,4-d]pyrimid-6-yl]buta-2,3-dienamide;

N-[4-(2-Phenethylbenzindazol-5-ylamino)pyrido[3,4-d]pyrimid-6-yl]but-2-enamide;

N-[4-(2-Phenethylbenzindazol-5-ylamino)pyrido[3,4-d]pyrimid-6-yl]-4,4,4-trifluorobut-2-enamide;

N-[4-(2-Benzylbenzindazol-5-ylamino)pyrido[3,4-d]pyrimid-6-yl]-4,4,4-trifluorobut-2-enamide;

N-[4-(1-Phenethylbenzindazol-5-ylamino)pyrido[3,4-d]pyrimid-6-yl]-3-chloroacrylamide;

6-(S-Vinylsulfonamido)-4-(1-phenethylbenzindazol-5-ylamino)pyrido[3,4-d]pyrimidine;

6-(S-Vinylsulfonamido)-4-(2-benzylbenzindazol-5-ylamino)pyrido[3,4-d]pyrimidine;

N-[4-(2-Benzylbenzindazol-5-ylamino)pyrido[3,4-d]pyrimid-6-yl]-4-hydroxy-4-oxobut-2-enamide;

N-[4-(2-Benzylbenzindazol-5-ylamino)pyrido[3,4-d]pyrimid-6-yl]-4-(3-(N,N-dimethylamino)propylamino)-4-oxobut-2-enamide;

N-[4-(2-Benzyloxyindol-5-ylamino)pyrido[3,4-d]pyrimid-6-yl]-4-(3-(4-morpholino)propoxy)-4-oxobut-2-enamide;

N-[4-(2-Benzylbenzindazol-5-ylamino)pyrido[3,4-d]pyrimid-6-yl]-4-(3-(4-morpholino)propoxy)-4-oxobut-2-enamide;

N-[4-(2-Benzylbenzindazol-5-ylamino)pyrido[3,4-d]pyrimid-6-yl]-4-(3-(4-morpholino)propylamino)-4-oxobut-2-enamide;

N-[4-(2-Benzyloxyindol-5-ylamino)pyrido[3,4-d]pyrimid-6-yl]-4-(3-(4-morpholino)propylamino)-4-oxobut-2-enamide;

4,4-Difluoro-8-(morpholin-4-yl)oct-2-enoic acid [4-(2-benzyloxybenzimidazol-5-ylamino)pyrido[3,4-d]pyrimid-6-yl]amide;

4,4-Difluoro-8-(morpholin-4-yl)oct-2-enoic acid [4-(2-benzylbenzindazol-5-ylamino)pyrido[3,4-d]pyrimid-6-yl]amide;

Pent-2-enedioic acid 1{[4-(2-benzylbenzindazol-5-ylamino)pyrido[3,4-d]pyrimid-6-yl]amide}5-[(3-morpholin-4-ylpropyl)amide];

Pent-2-enedioic acid 1{[4-(2-benzylsulfonylbenzimidazol-5-ylamino)pyrido[3,4-d]pyrimid-6-yl]amide}5-[(3-morpholin-4-ylpropyl)amide];

N-[4-(4-benzyloxybenzimidazol-5-ylamino)pyrido[3,4-d]pyrimid-6-yl]-4-(3-(morpholin-4-yl)propylthio)but-2-enamide;

N-[4-(2-Benzylbenzindazol-5-ylamino)pyrido[3,4-d]pyrimid-6-yl]-4-(3-(morpholin-4-yl)propylthio)but-2-enamide;

7-Morpholin-4-ylhept-2-ynoic acid [4-(2-benzylbenzindazol-5-ylamino)pyrido[3,4-d]pyrimid-6-yl]amide;

7-Morpholin-4-ylhept-2-ynoic acid [4-(2-benzylsulfonylbenzimidazol-5-ylamino)pyrido[3,4-d]pyrimid-6-yl]amide;

N-[4-(2-Benzylbenzindazol-5-ylamino)benzo[b]thieno[3,2-d]-pyrimid-6-yl]acrylamide;

N-[4-(1-Benzylbenzindazol-5-ylamino)benzo[b]thieno[3,2-d]-pyrimid-6-yl]acrylamide;

[4-(2-Benzylbenzindazol-5-ylamino)quinazolin-6-yl]acrylate;

N-(3-(4-Morpholino)propylamino)-4,O-[4-(2-benzylbenzindazol-5-ylamino)quinazolin-6-yl]-4-oxobut-2-enamide;

4,4-Difluoro-8-(morpholin-4-yl)oct-2-enoic acid [4-(2-benzylbenzindazol-5-ylamino)quinazolin-6-yl]ester;

Pent-2-enedioic acid 1{[4-(2-benzylbenzindazol-5-ylamino)quinazolin-6-yl]ester}5-[(3-morpholin-4-ylpropyl)amide];

[4-(2-Benzylbenzindazol-5-ylamino)quinazolin-6-yl]-4-(3-(morpholin-4-yl)propylthio)but-2-enoate; and 7-Morpholin-4-ylhept-2-ynoic acid [4-(2-benzylbenzindazol-5-ylamino)quinazolin-6-yl]ester.

\* \* \* \* \*

UNITED STATES PATENT AND TRADEMARK OFFICE
CERTIFICATE OF CORRECTION

PATENT NO. : 6,153,617  
DATED : November 28, 2000  
INVENTOR(S) : Bridges, A.J.

Page 1 of 3

It is certified that error appears in the above-identified patent and that said Letters Patent is hereby corrected as shown below:

Column 57,
Line 67, after "optionally" insert -- substituted heterocyclic aromatic ring; --.

Column 58,
Delete lines 1 and 2, "$R^3$ is hydrogen or halogen substituted heterocyclic aromatic ring;".
Before line 4, "$R^5$ is hydrogen, halogen, $C_1$-$C_6$ perfluoroalkyl, 1,1-", insert -- $R^{13}$ is hydrogen or halogen; --
Line 31, after "wherein", insert -- X is --.
Line 55, delete

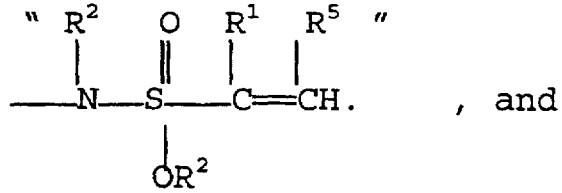, and insert instead -- 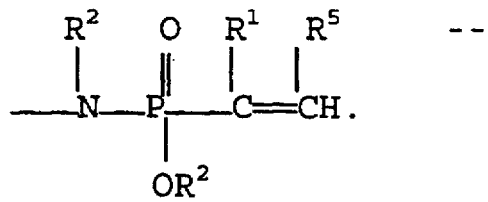 --

Column 59,
Line 4, delete 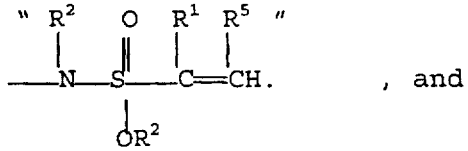, and insert instead -- 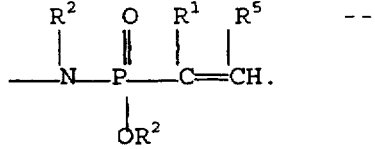 --

UNITED STATES PATENT AND TRADEMARK OFFICE
CERTIFICATE OF CORRECTION

PATENT NO.  : 6,153,617  
DATED       : November 28, 2000  
INVENTOR(S) : Bridges, A.J.

Page 2 of 3

It is certified that error appears in the above-identified patent and that said Letters Patent is hereby corrected as shown below:

Column 59,
Line 32, after "patient" delete "a" and insert
instead -- needing --.
Line 51, delete "-C=C-R$^5$," and insert instead -- -C $\equiv$ C-R$^5$, --.
Line 64, after "each" delete "C$_1$-C$_1$ alkyl" and
insert instead -- C$_1$-C$_6$ alkyl --.

Column 60,
Line 7, delete "-C=C-R$^5$," and insert instead -- -C $\equiv$ C-R$^5$, --.
Line 21, before "group" delete "C$_1$-C$_1$ alkyl" and
insert instead -- C$_1$-C$_6$ alkyl --.

Column 62,
Delete line 53, "N-[4-(6-chloro-2,3-dihydroindol1-yl)pyrido[3,4-d]", to line 67, "pyrimid-7-yl]propynamide;".

Column 63,
Delete line 1, "N-[4-(5-Amino-2,3-dihyroindol-l-yl)pyrido[4,3-d]", to line 67, "oxobut-2-enamide;".

Column 64,
Delete line 1, "4,4-Difluoro-8-(morpholin-4-yl)oct-2-enoic acid [4-(6-", to line 34, "[3,2-d]-pyrimid-6yl]acrylamide;".

Column 66,
Delete line 38, "N-[4-(1H-Indazol-4-ylamino)pyrido[3,4-d]pyrimid-6-yl]", to line 67, "enamide;".

Column 67,
Delete line 1, "N-[4-(1H-Benzotriazol-7-ylamino)pyrido[3, 4-d]pyrimid-", to line 67, "pyrido[3, 4-d]pyrimid-6-yl]amide;".

Column 68,
Delete line 1, "4-Morpholin-4-ylbut-2-ynoic acid [4- (benzo [c] [2, 1, 3] ", to line 11, "yl] acrylamide; " .

Column 70,
Delete line 12, "N-[4-(2-benzylbenzindazol-5-ylamino)pyrido[3,4,-d]", to line 67, "amide];".

UNITED STATES PATENT AND TRADEMARK OFFICE
CERTIFICATE OF CORRECTION

PATENT NO.   : 6,153,617
DATED        : November 28, 2000
INVENTOR(S)  : Bridges, A.J.

It is certified that error appears in the above-identified patent and that said Letters Patent is hereby corrected as shown below:

<u>Column 71</u>,
Delete line 1, "N-[4-(4-benzyloxybenzimidazol-5-ylamino)pyrido[3, 4-", to line 17, "2-d]-pyrimid-6-yl]acrylamide;"

Signed and Sealed this

Eighth Day of January, 2002

Attest:

Attesting Officer

JAMES E. ROGAN
*Director of the United States Patent and Trademark Office*